United States Patent [19]
Lin et al.

[11] Patent Number: 5,843,675
[45] Date of Patent: Dec. 1, 1998

[54] TNF RECEPTOR DEATH DOMAIN LIGAND PROTEINS AND INHIBITORS OF LIGAND BINDING

[75] Inventors: Lih-Ling Lin, Concord; Jennifer Chen, Chestnut Hill; Andrea R. Schievella, Winchester; James Graham, Somerville, all of Mass.

[73] Assignee: Genetics Institute, Inc., Cambridge, Mass.

[21] Appl. No.: 602,228

[22] Filed: Feb. 15, 1996

Related U.S. Application Data

[63] Continuation-in-part of Ser. No. 533,901, Sep. 26, 1995, which is a continuation-in-part of Ser. No. 494,440, Jun. 19, 1995, which is a continuation-in-part of Ser. No. 327,514, Oct. 19, 1994, abandoned.

[51] Int. Cl.$^6$ .................. G01N 33/53; C07K 14/705; C12N 15/12

[52] U.S. Cl. .................. 435/7.1; 435/691; 530/350; 536/73.5

[58] Field of Search .................. 435/69.1, 6, 7.1, 435/7.2, 69.7; 530/350

[56] References Cited

U.S. PATENT DOCUMENTS

| | | | |
|---|---|---|---|
| 5,464,938 | 11/1995 | Smith et al. | 530/350 |
| 5,506,340 | 4/1996 | Heavener | 530/324 |
| 5,563,039 | 10/1996 | Goeddel et al. | 435/7.1 |

FOREIGN PATENT DOCUMENTS

| | | |
|---|---|---|
| A-46127/93 | 9/1993 | Australia . |
| 585 939 | 9/1984 | European Pat. Off. . |
| WO 92/03470 | 3/1992 | WIPO . |
| WO 92/03471 | 3/1992 | WIPO . |
| WO 92/14834 | 9/1992 | WIPO . |
| WO 94/01548 | 1/1994 | WIPO . |
| WO 94/10207 | 5/1994 | WIPO . |
| WO 95/31544 | 11/1995 | WIPO . |
| WO 95/33051 | 12/1995 | WIPO . |
| WO 96/25941 | 8/1996 | WIPO . |

OTHER PUBLICATIONS

Luban and Goff, 1995, *Curr. Opin. Biotech.* 6: 59–64.
Waye et al., Protein Engineering 8:90 (1995).
Rothe et al., Cell 78:681–692 (1994).
Song et al., The Journal of Biological Chemistry 269:22492–22495 (1994).
Tartaglia et al., Cell 74:845–853 (1993).
Boldin et al., The Journal of Biological Chemistry 270(1):387–391 (1995).
Hsu et al., Cell 81:495–504 (1995).
Boldin et al., FEBS Letters 367:39–44 (1995).
Schall et al., Cell 61:361–370 (1990).
Tartaglia et al., Cell 74:845–853 (1993).
Shimasaki et al., J. Biol. Chem. 266:10646–10653 (1991).
Saragovi et al., Bio/Technology 10:773–778 (1992).
McDowell et al., J. Amer. Chem. Soc. 114:9245–9253 (1992).
Kaufman et al., Nucleic Acids Res. 19:4485–4490 (1991).
Kaufman et al., Methods in Enzymology 185:537–566 (1990).
Gyuris et al., Cell 75:791–803 (1993).
Gietz et al., Nucleic Acids Res. 20:1425 (1992).

*Primary Examiner*—John Ulm
*Attorney, Agent, or Firm*—Suzanne A. Sprunger; Scott A. Brown

[57] ABSTRACT

Novel TNF receptor death domain ("TNF-R1-DD") ligand proteins are disclosed. Polynucleotides encoding the TNF-R1-DD ligand protein are also disclosed, along with vectors, host cells, and methods of making the TNF-R1-DD ligand protein. Pharmaceutical compositions containing the TNF-R1-DD ligand protein, methods of treating inflammatory conditions, and methods of inhibiting TNF-R death domain binding are also disclosed. Methods of identifying inhibitors of TNF-R death domain binding and inhibitors identified by such methods are also disclosed.

16 Claims, 8 Drawing Sheets

TNF RECEPTOR DEATH DOMAIN LIGAND PROTEINS AND INHIBITORS OF LIGAND BINDING

This application is a continuation-in-part of application Ser. No. 08/533,901, filed Sep. 26, 1995, which was a continuation-in-part of application Ser. No. 08/494,440, filed Jun. 19, 1995, which was a continuation-in-part of application Ser. No. 08/327,514, filed Oct. 19, 1994, now abandoned.

BACKGROUND OF THE INVENTION

The present invention relates to the field of anti-inflammatory substances and other substances which act by inhibiting binding to the intracellular domain of a tumor necrosis factor receptor (hereinafter "TNF-R"), such as, for example, the P55 type (or TNF-R1) TNF receptor. More particularly, the present invention is directed to novel ligands which bind to the TNF-R intracellular domain and to inhibition or modulation of signal transduction by this receptor.

Tumor necrosis factor (herein "TNF") is a cytokine which produces a wide range of cellular activities. TNF causes an inflammatory response, which can be beneficial, such as in mounting an immune response to a pathogen, or when overexpressed can lead to other detrimental effects of inflammation.

The cellular effects of TNF are initiated by the binding of TNF to its receptors (TNF-Rs) on the surface of target cells. The isolation of polynucleotides encoding TNF-Rs and variant forms of such receptors has been described in European patent publication Nos. EP 308,378, EP 393,438, EP 433,900, EP 526,905 and EP 568,925; in PCT patent publication Nos. WO91/03553 and WO93/19777; and by Schall et al., Cell 61:361–370 (1990) (disclosing the P55 type TNF receptor). Processes for purification of TNF-Rs have also been disclosed in U.S. Pat. No. 5,296,592.

Native TNF-Rs are characterized by distinct extracellular, transmembrane and intracellular domains. The primary purpose of the extracellular domain is to present a binding site for TNF on the outside of the cell. When TNF is bound to the binding site, a "signal" is transmitted to the inside of the cell through the transmembrane and intracellular domains, indicating that binding has occurred. Transmission or "transduction" of the signal to the inside of the cell occurs by a change in conformation of the transmembrane and/or intracellular domains of the receptor. This signal is "received" by the binding of proteins and other molecules to the intracellular domain of the receptor, resulting in the effects seen upon TNF stimulation. Two distinct TNF receptors of ~55 kd ("TNF-R1") and ~75 kd ("TNF-R2") have been identified. Numerous studies with anti-TNF receptor antibodies have demonstrated that TNF-R1 is the receptor which signals the majority of the pleiotropic activities of TNF. Recently, the domain required for signaling cytotoxicity and other TNF-mediated responses has been mapped to the ~80 amino acid near the C-terminus of TNF-R1. This domain is therefore termed the "death domain" (hereinafter referred to as "TNF-R death domain" and "TNF-R1-DD") (see, Tartaglia et al., Cell 74:845–853 (1993)).

While TNF binding by TNF-Rs results in beneficial cellular effects, it is often desirable to prevent or deter TNF binding from causing other detrimental cellular effects. Although substantial effort has been expended investigating inhibition of TNF binding to the extracellular domain of TNF-Rs, examination of binding of proteins and other molecules to the intracellular domain of TNF-Rs has received much less attention.

However, ligands which bind to the TNF-R intracellular domain have yet to be identified. It would be desirable to identify and isolate such ligands to examine their effects upon TNF-R signal transduction and their use as therapeutic agents for treatment of TNF-induced conditions. Furthermore, identification of such ligands would provide a means for screening for inhibitors of TNF-R/intracellular ligand binding, which will also be useful as anti-inflammatory agents.

SUMMARY OF THE INVENTION

Applicants have for the first time identified novel TNF-R1-DD ligand proteins and have isolated polynucleotides encoding such ligands. Applicants have also identified a known protein which may also bind to the death domain of TNF-R.

In one embodiment, the present invention provides a composition comprising an isolated polynucleotide encoding a protein having TNF-R1-DD ligand protein activity. In preferred embodiments, the polynucleotide is selected from the group consisting of:

(a) a polynucleotide comprising the nucleotide sequence of SEQ ID NO:1 from nucleotide 2 to nucleotide 1231;

(b) a polynucleotide comprising a fragment of the nucleotide sequence of SEQ ID NO:1;

(c) a polynucleotide encoding an TNF-R1-DD ligand protein comprising the amino acid sequence of SEQ ID NO:2;

(d) a polynucleotide encoding an TNF-R1-DD ligand protein comprising a fragment of the amino acid sequence of SEQ ID NO:2;

(e) a polynucleotide comprising the nucleotide sequence of SEQ ID NO:3 from nucleotide 2 to nucleotide 415;

(f) a polynucleotide comprising a fragment of the nucleotide sequence of SEQ ID NO:3;

(g) a polynucleotide encoding an TNF-R1-DD ligand protein comprising the amino acid sequence of SEQ ID NO:4;

(h) a polynucleotide encoding an TNF-R1-DD ligand protein comprising a fragment of the amino acid sequence of SEQ ID NO:4;

(i) a polynucleotide comprising the nucleotide sequence of SEQ ID NO:9 from nucleotide 2 to nucleotide 931;

(j) a polynucleotide comprising a fragment of the nucleotide sequence of SEQ ID NO:9;

(k) a polynucleotide encoding an TNF-R1-DD ligand protein comprising the amino acid sequence of SEQ ID NO:10;

(l) a polynucleotide encoding an TNF-R1-DD ligand protein comprising a fragment of the amino acid sequence of SEQ ID NO:10;

(m) a polynucleotide comprising the nucleotide sequence of SEQ ID NO:11 from nucleotide 2 to nucleotide 1822;

(n) a polynucleotide comprising a fragment of the nucleotide sequence of SEQ ID NO:11;

(o) a polynucleotide encoding an TNF-R1-DD ligand protein comprising the amino acid sequence of SEQ ID NO:12;

(p) a polynucleotide encoding an TNF-R1-DD ligand protein comprising a fragment of the amino acid sequence of SEQ ID NO:12;

(q) a polynucleotide comprising the nucleotide sequence of SEQ ID NO:13 from nucleotide 3 to nucleotide 2846;

(r) a polynucleotide comprising a fragment of the nucleotide sequence of SEQ ID NO:13, which encodes a protein having TNF-R1-DD ligand protein activity;

(s) a polynucleotide encoding an TNF-R1-DD ligand protein comprising the amino acid sequence of SEQ ID NO:14;

(t) a polynucleotide encoding an TNF-R1-DD ligand protein comprising a fragment of the amino acid sequence of SEQ ID NO:14 and having TNF-R1-DD ligand protein activity;

(u) a polynucleotide comprising the nucleotide sequence of SEQ ID NO:15 from nucleotide 326 to nucleotide 5092;

(v) a polynucleotide comprising a fragment of the nucleotide sequence of SEQ ID NO:15;

(w) a polynucleotide encoding an TNF-R1-DD ligand protein comprising the amino acid sequence of SEQ ID NO:16;

(x) a polynucleotide encoding an TNF-R1-DD ligand protein comprising a fragment of the amino acid sequence of SEQ ID NO:16; and (y) a polynucleotide capable of hybridizing under stringent conditions to any one of the polynucleotides specified in (a)–(x).

In certain preferred embodiments, the polynucleotide is operably linked to an expression control sequence. The invention also provides a host cell, including bacterial, yeast, insect and mammalian cells, transformed with such polynucleotide compositions.

Processes are also provided for producing an TNF-R1-DD ligand protein, which comprises:

(a) growing a culture of the host cell transformed with such polynucleotide compositions in a suitable culture medium; and (b) purifying the TNF-R1-DD ligand protein from the culture.

The ligand protein produced according to such methods is also provided by the present invention.

Compositions comprising a protein having TNF-R1-DD ligand protein activity are also disclosed. In preferred embodiments the protein comprises an amino acid sequence selected from the group consisting of:

(a) the amino acid sequence of SEQ ID NO:2;

(b) fragments of the amino acid sequence of SEQ ID NO:2;

(c) the amino acid sequence of SEQ ID NO:4;

(d) fragments of the amino acid sequence of SEQ ID NO:4;

(e) the amino acid sequence of SEQ ID NO:6;

(f) fragments of the amino acid sequence of SEQ ID NO:6;

(g) the amino acid sequence of SEQ ID NO:10;

(h) fragments of the amino acid sequence of SEQ ID NO:10;

(i) the amino acid sequence of SEQ ID NO:12;

(j) fragments of the amino acid sequence of SEQ ID NO:12;

(k) the amino acid sequence of SEQ ID NO:14;

(l) fragments of the amino acid sequence of SEQ ID NO:14;

(m) the amino acid sequence of SEQ ID NO:16; and (n) fragments of the amino acid sequence of SEQ ID NO:16;

the protein being substantially free from other mammalian proteins. Such compositions may further comprise a pharmaceutically acceptable carrier.

Compositions comprising an antibody which specifically reacts with such TNF-R1-DD ligand protein are also provided by the present invention.

Methods are also provided for identifying an inhibitor of TNF-R death domain binding which comprise:

(a) combining an TNF-R death domain protein with an TNF-R1-DD ligand protein, said combination forming a first binding mixture;

(b) measuring the amount of binding between the TNF-R death domain protein and the TNF-R1-DD ligand protein in the first binding mixture;

(c) combining a compound with the TNF-R death domain protein and an TNF-R1-DD ligand protein to form a second binding mixture;

(d) measuring the amount of binding in the second binding mixture; and (e) comparing the amount of binding in the first binding mixture with the amount of binding in the second binding mixture;

wherein the compound is capable of inhibiting TNF-R death domain binding when a decrease in the amount of binding of the second binding mixture occurs. In certain preferred embodiments the TNF-R1-DD ligand protein used in such method comprises an amino acid sequence selected from the group consisting of:

(a) the amino acid sequence of SEQ ID NO:2;

(b) fragments of the amino acid sequence of SEQ ID NO:2;

(c) the amino acid sequence of SEQ ID NO:4;

(d) fragments of the amino acid sequence of SEQ ID NO:4;

(e) the amino acid sequence of SEQ ID NO:6;

(f) fragments of the amino acid sequence of SEQ ID NO:6;

(g) the amino acid sequence of SEQ ID NO:8;

(h) fragments of the amino acid sequence of SEQ ID NO:8

(i) the amino acid sequence of SEQ ID NO:10;

(j) fragments of the amino acid sequence of SEQ ID NO:10;

(k) the amino acid sequence of SEQ ID NO:12;

(l) fragments of the amino acid sequence of SEQ ID NO:12;

(m) the amino acid sequence of SEQ ID NO:14;

(n) fragments of the amino acid sequence of SEQ ID NO:14;

(o) the amino acid sequence of SEQ ID NO:16; and (p) fragments of the amino acid sequence of SEQ ID NO:16.

Compositions comprising inhibitors identified according to such method are also provided. Such compositions may include pharmaceutically acceptable carriers.

Methods are also provided for preventing or ameliorating an inflammatory condition which comprises administering a therapeutically effective amount of a composition comprising a protein having TNF-R1-DD ligand protein activity and a pharmaceutically acceptable carrier.

Other embodiments provide methods of inhibiting TNF-R death domain binding comprising administering a therapeutically effective amount of a composition comprising a protein having TNF-R1-DD ligand protein activity and a pharmaceutically acceptable carrier.

Methods are also provided for preventing or ameliorating an inflammatory condition which comprises administering to a mammalian subject a therapeutically effective amount of a composition comprising a pharmaceutically acceptable carrier and a protein selected from the group consisting of insulin-like growth factor binding protein-5 ("IGFBP-5"), and fragments thereof having TNF-R1-DD ligand protein activity. Such proteins may also be administered for inhibiting TNF-R death domain binding.

Methods of preventing or ameliorating an inflammatory condition or of inhibiting TNF-R death domain binding are provided, which comprise administering to a mammalian subject a therapeutically effective amount of inhibitors of TNF-R death domain binding, are also provided.

Methods of identifying an inhibitor of TNF-R death domain binding are also provided by the present invention which comprise:

(a) transforming a cell with a first polynucleotide encoding an TNF-R death domain protein, a second polynucleotide encoding an TNF-R1-DD ligand protein, and at least one reporter gene, wherein the expression of the reporter gene is regulated by the binding of the TNF-R1-DD ligand protein encoded by the second polynucleotide to the TNF-R death domain protein encoded by the first polynucleotide;

(b) growing the cell in the presence of and in the absence of a compound; and (c) comparing the degree of expression of the reporter gene in the presence of and in the absence of the compound; wherein the compound is capable of inhibiting TNF-R death domain binding when a decrease in the degree of expression of the reporter gene occurs. In preferred embodiments, the cell is a yeast cell and the second polynucleotide is selected from the group consisting of:

(a) a polynucleotide comprising the nucleotide sequence of SEQ ID NO:1 from nucleotide 2 to nucleotide 1231;

(b) a polynucleotide comprising a fragment of the nucleotide sequence of SEQ ID NO:1, which encodes a protein having TNF-R1-DD ligand protein activity;

(c) a polynucleotide encoding an TNF-R1-DD ligand protein comprising the amino acid sequence of SEQ ID NO:2;

(d) a polynucleotide encoding an TNF-R1-DD ligand protein comprising a fragment of the amino acid sequence of SEQ ID NO:2 and having TNF-R1-DD ligand protein activity;

(e) a polynucleotide comprising the nucleotide sequence of SEQ ID NO:3 from nucleotide 2 to nucleotide 415;

(f) a polynucleotide comprising a fragment of the nucleotide sequence of SEQ ID NO:3, which encodes a protein having TNF-R1-DD ligand protein activity;

(g) a polynucleotide encoding an TNF-R1-DD ligand protein comprising the amino acid sequence of SEQ ID NO:4;

(h) a polynucleotide encoding an TNF-R1-DD ligand protein comprising a fragment of the amino acid sequence of SEQ ID NO:4 and having TNF-R1-DD ligand protein activity;

(i) a polynucleotide comprising the nucleotide sequence of SEQ ID NO:5 from nucleotide 2 to nucleotide 559;

(j) a polynucleotide comprising a fragment of the nucleotide sequence of SEQ ID NO:5, which encodes a protein having TNF-R1-DD ligand protein activity;

(k) a polynucleotide encoding an TNF-R1-DD ligand protein comprising the amino acid sequence of SEQ ID NO:6;

(l) a polynucleotide encoding an TNF-R1-DD ligand protein comprising a fragment of the amino acid sequence of SEQ ID NO:6 and having TNF-R1-DD ligand protein activity;

(m) a polynucleotide comprising the nucleotide sequence of SEQ ID NO:7 from nucleotide 57 to nucleotide 875;

(n) a polynucleotide comprising a fragment of the nucleotide sequence of SEQ ID NO:7, which encodes a protein having TNF-R1-DD ligand protein activity;

(o) a polynucleotide encoding an TNF-R1-DD ligand protein comprising the amino acid sequence of SEQ ID NO:8;

(p) a polynucleotide encoding an TNF-R1-DD ligand protein comprising a fragment of the amino acid sequence of SEQ ID NO:8 and having TNF-R1-DD ligand protein activity;

(q) a polynucleotide comprising the nucleotide sequence of SEQ ID NO:9 from nucleotide 2 to nucleotide 931;

(r) a polynucleotide comprising a fragment of the nucleotide sequence of SEQ ID NO:9;

(s) a polynucleotide encoding an TNF-R1-DD ligand protein comprising the amino acid sequence of SEQ ID NO:10;

(t) a polynucleotide encoding an TNF-R1-DD ligand protein comprising a fragment of the amino acid sequence of SEQ ID NO:10;

(u) a polynucleotide comprising the nucleotide sequence of SEQ ID NO:11 from nucleotide 2 to nucleotide 1822;

(v) a polynucleotide comprising a fragment of the nucleotide sequence of SEQ ID NO:11;

(w) a polynucleotide encoding an TNF-R1-DD ligand protein comprising the amino acid sequence of SEQ ID NO:12;

(x) a polynucleotide encoding an TNF-R1-DD ligand protein comprising a fragment of the amino acid sequence of SEQ ID NO:12;

(y) a polynucleotide comprising the nucleotide sequence of SEQ ID NO:13 from nucleotide 3 to nucleotide 2846;

(z) a polynucleotide comprising a fragment of the nucleotide sequence of SEQ ID NO:13, which encodes a protein having TNF-R1-DD ligand protein activity;

(aa) a polynucleotide encoding an TNF-R1-DD ligand protein comprising the amino acid sequence of SEQ ID NO:14;

(bb) a polynucleotide encoding an TNF-R1-DD ligand protein comprising a fragment of the amino acid sequence of SEQ ID NO:14 and having TNF-R1-DD ligand protein activity;

(cc) a polynucleotide comprising the nucleotide sequence of SEQ ID NO:15 from nucleotide 326 to nucleotide 5092;

(dd) a polynucleotide comprising a fragment of the nucleotide sequence of SEQ ID NO:15, which encodes a protein having TNF-R1-DD ligand protein activity;

(ee) a polynucleotide encoding an TNF-R1-DD ligand protein comprising the amino acid sequence of SEQ ID NO:16;

(ff) a polynucleotide encoding an TNF-R1-DD ligand protein comprising a fragment of the amino acid sequence of SEQ ID NO:16 and having TNF-R1-DD ligand protein activity; and (gg) a polynucleotide capable of hybridizing under stringent conditions to any one of the polynucleotides specified in (a)–(ff), which encodes a protein having TNF-R1-DD ligand protein activity.

DETAILED DESCRIPTION OF THE INVENTION

Figure 1:
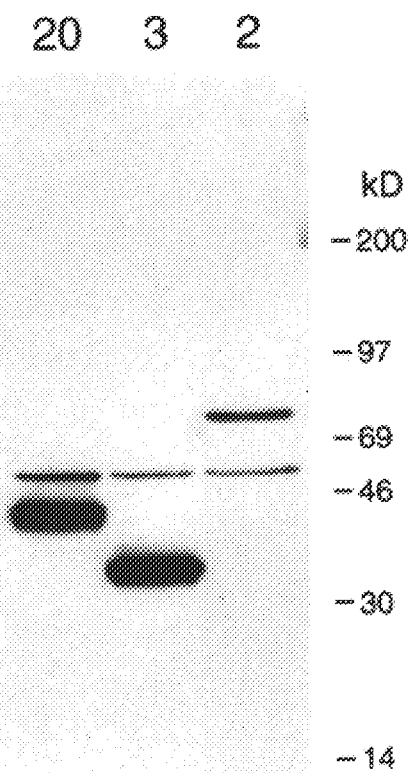
FIGS. 1 and 2 depict autoradiographs demonstrating the expression of TNF-R1-DD ligand proteins of the present invention.

The present inventors have for the first time identified and isolated novel polynucleotides which encode proteins which bind to the TNF-R death domain. As used herein "TNF-R" includes all receptors for tumor necrosis factor. The P55 type TNF-R is the preferred receptor for practicing the present invention.

The sequence of a polynucleotide encoding one such protein is set forth in SEQ ID NO:1 from nucleotides 2 to 1231. This polynucleotide has been identified as "clone 2DD" The amino acid sequence of the TNF-R1-DD ligand protein encoded by clone 2DD is set forth in SEQ ID NO:2. It is believed that clone 2DD is a partial cDNA clone of a longer full length coding sequence. However, as demonstrated herein the protein encoded by clone 2DD does bind the death domain of TNF-R (i.e., has "TNF-R1-DD ligand protein activity" as defined herein). Clone 2DD was deposited with the American Type Culture Collection on Oct. 13, 1994 and given the accession number ATCC 69706.

The protein encoded by clone 2DD is 410 amino acids in length. No identical or closely related sequences were found using BLASTN/BLASTX or FASTA searches. Therefore, clone 2DD encodes a novel protein.

The sequence of a polynucleotide encoding one such protein is set forth in SEQ ID NO:3 from nucleotides 2 to 415. This polynucleotide has been identified as "clone 3DD". The amino acid sequence of the TNF-R1-DD ligand protein encoded by clone 3DD is set forth in SEQ ID NO:4. It is believed that clone 3DD is a partial cDNA clone of a longer full length coding sequence. However, as demonstrated herein the protein encoded by clone 3DD does bind the death domain of TNF-R (i.e., has "TNF-R1-DD ligand protein activity" as defined herein). Clone 3DD was deposited with the American Type Culture Collection on Oct. 13, 1994 and given the accession number ATCC 69705.

The protein encoded by clone 3DD is 138 amino acids. No identical or closely related sequences were found using BLASTN/BLASTX or FASTA searches. Therefore, clone 3DD encodes a novel protein.

A full-length clone corresponding to clone 3DD was also isolated and identified as "clone 3TW". The nucleotide sequence of clone 3TW is reported as SEQ ID NO:13. Nucleotides 3 to 2846 of SEQ ID NO:13 encode a TNF-R1-DD ligand protein, the amino acid sequence of which is reported as SEQ ID NO:14. Amino acids 811 to 948 of SEQ ID NO:14 correspond to amino acids 1 to 138 of SEQ ID NO:4 (clone 3DD). Clone 3TW was deposited with the American Type Culture Collection on Sep. 26, 1995 and given the accession number ATCC 69904.

The sequence of a polynucleotide encoding another such protein is set forth in SEQ ID NO:5 from nucleotides 2 to 559. This polynucleotide has been identified as "clone 20DD." The amino acid sequence of the TNF-R1-DD ligand protein encoded by clone 20DD is set forth in SEQ ID NO:6. It is believed that clone 20DD is a partial cDNA clone of a longer full length coding sequence. However, as demonstrated herein the protein encoded by clone 20DD does bind the death domain of TNF-R (i.e., has "TNF-R1-DD ligand protein activity" as defined herein). Clone 20DD was deposited with the American Type Culture Collection on Oct. 13, 1994 and given the accession number ATCC 69704.

The protein encoded by clone 20DD is identical to amino acids 87 to 272 of insulin-like growth factor binding protein-5 ("IGFBP-5"), a sequence for which was disclosed in J. Biol. Chem. 266:10646–10653 (1991) by Shimasaki et al., which is incorporated herein by reference. The polynucleotide and amino acid sequences of IGFBP-5 are set forth in SEQ ID NO:7 and SEQ ID NO:8, respectively. Based upon the sequence identity between clone 20DD and IGFBP-5, IGFBP-5 and certain fragments thereof will exhibit TNF-R1-DD ligand binding activity (as defined herein).

The sequence of a polynucleotide encoding another such protein is set forth in SEQ ID NO:9 from nucleotides 2 to 931. This polynucleotide has been identified as "clone 1TU" The amino acid sequence of the TNF-R1-DD ligand protein encoded by clone 1TU is set forth in SEQ ID NO:10. It is believed that clone ITU is a partial cDNA clone of a longer full length coding sequence. However, as demonstrated herein the protein encoded by clone 1TU does bind the death domain of TNF-R (i.e., has "TNF-R1-DD ligand protein activity" as defined herein). Clone 1TU was deposited with the American Type Culture Collection on Jun. 7, 1995 and given the accession number ATCC 69848.

The protein encoded by clone 1TU is 310 amino acids in length. No identical or closely related sequences were found using BLASTN/BLASTX or FASTA searches. Therefore, clone 1TU encodes a novel protein.

The sequence of a polynucleotide encoding another such protein is set forth in SEQ ID NO:11 from nucleotides 2 to 1822. This polynucleotide has been identified as "clone 27TU" The amino acid sequence of the TNF-R1-DD ligand protein encoded by clone 27TU is set forth in SEQ ID NO:12. It is believed that clone 27TU is a partial cDNA clone of a longer full length coding sequence. However, as demonstrated herein the protein encoded by clone 27TU does bind the death domain of TNF-R (i.e., has "TNF-R1-DD ligand protein activity" as defined herein). Clone 27TU was deposited with the American Type Culture Collection on Jun. 7, 1995 and given the accession number ATCC 69846.

The protein encoded by clone 27TU is 607 amino acids in length. No identical or closely related sequences were found using BLASTN/BLASTX or FASTA searches. Therefore, clone 27TU encodes a novel protein. 27TU may be a longer version of clone 2DD. 2DD encodes the same amino acid sequence (SEQ ID NO:2) as amino acids 198–607 encoded by 27TU (SEQ ID NO:12). The nucleotide sequences of 2DD and 27TU are also identical within this region of identity.

An additional "clone 15TU" was isolated which encoded a portion of the 27TU sequence (approximately amino acids 289–607 of SEQ ID NO:12). Clone 15TU was deposited with the American Type Culture Collection on Jun. 7, 1995 and given the accession number ATCC 69847. 15TU comprises the same nucleotide sequence as 27TU over this region of amino acids.

A full-length clone corresponding to clone 27TU was also isolated and identified as "clone 57TU4A". The nucleotide sequence of clone 57TU4A is reported as SEQ ID NO:15. Nucleotides 336 to 5092 of SEQ ID NO:15 encode a TNF-R1-DD ligand protein, the amino acid sequence of which is reported as SEQ ID NO:146 Amino acids 982 to 1588 of SEQ ID NO:16 correspond to amino acids 1 to 607 of SEQ ID NO:12 (clone 27TU). Clone 57TU4A was deposited with the American Type Culture Collection on Feb. 13, 1996 and given the accession number ATCC 69988.

Polynucleotides hybridizing to the polynucleotides of the present invention under stringent conditions and highly stringent conditions are also part of the present invention. As used herein, "highly stringent conditions" include, for example, 0.2×SSC at 65° C.; and "stringent conditions" include, for example, 4×SSC at 65° C. or 50% formamide and 4×SSC at 42° C.

For the purposes of the present application, "TNF-R1-DD ligand protein" includes proteins which exhibit TNF-R1-DD ligand protein activity. For the purposes of the present application, a protein is defined as having "TNF-R1-DD ligand protein activity" when it binds to a protein derived from the TNF-R death domain. Activity can be measured by using any assay which will detect binding to an TNF-R death domain protein. Examples of such assays include without limitation the interaction trap assays and assays in which TNF-R death domain protein which is affixed to a surface in a manner conducive to observing binding, including without limitation those described in Examples 1 and 3. As used herein an "TNF-R death domain protein" includes the entire death domain or fragments thereof.

Fragments of the TNF-R1-DD ligand protein which are capable of interacting with the TNF-R death domain or which are capable of inhibiting TNF-R death domain binding (i.e., exhibit TNF-R1-DD ligand protein activity) are also encompassed by the present invention. Fragments of the TNF-R1-DD ligand protein may be in linear form or they may be cyclized using known methods, for example, as described in H. U. Saragovi, et al., Bio/Technology 10, 773–778 (1992) and in R. S. McDowell, et al., J. Amer. Chem. Soc. 114, 9245–9253 (1992), both of which are incorporated herein by reference. Such fragments may be fused to carrier molecules such as immunoglobulins for many purposes, including increasing the valency of TNF-R1-DD ligand protein binding sites. For example, fragments of the TNF-R1-DD ligand protein may be fused through "linker" sequences to the Fc portion of an immunoglobulin. For a bivalent form of the TNF-R1-DD ligand protein, such a fusion could be to the Fc portion of an IgG molecule. Other immunoglobulin isotypes may also be used to generate such fusions. For example, an TNF-R1-DD ligand protein—IgM fusion would generate a decavalent form of the TNF-R1-DD ligand protein of the invention.

The isolated polynucleotide of the invention may be operably linked to an expression control sequence such as the pMT2 or pED expression vectors disclosed in Kaufman et al., Nucleic Acids Res. 19, 4485–4490 (1991), in order to produce the TNF-R1-DD ligand protein recombinantly. Many suitable expression control sequences are known in the art. General methods of expressing recombinant proteins are also known and are exemplified in R. Kaufman, Methods in Enzymology 185, 537–566 (1990). As defined herein "operably linked" means that the isolated polynucleotide of the invention and the expression control sequence are situated within a vector or cell in such a way that the TNF-R1-DD ligand protein is expressed by a host cell which has been transformed (transfected) with the ligated polynucleotide/expression control sequence.

A number of types of cells may act as suitable host cells for expression of the TNF-R1-DD ligand protein. Host cells include, for example, monkey COS cells, Chinese Hamster Ovary (CHO) cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

The TNF-R1-DD ligand protein may also be produced by operably linking the isolated polynucleotide of the invention to suitable control sequences in one or more insect expression vectors, and employing an insect expression system. Materials and methods for baculovirus/insect cell expression systems are commercially available in kit form from, e.g., Invitrogen, San Diego, Calif., U.S.A. (the MaxBac® kit), and such methods are well known in the art, as described in Summers and Smith, Texas Agricultural Experiment Station Bulletin No. 1555 (1987), incorporated herein by reference.

Alternatively, it may be possible to produce the TNF-R1-DD ligand protein in lower eukaryotes such as yeast or in prokaryotes such as bacteria. Potentially suitable yeast strains include Saccharomyces cerevisiae, Schizosaccharomyces pombe, Kluyveromyces strains, Candida, or any yeast strain capable of expressing heterologous proteins. Potentially suitable bacterial strains include Escherichia coli, Bacillus subtilis, Salmonella typhimurium, or any bacterial strain capable of expressing heterologous proteins. If the TNF-R1-DD ligand protein is made in yeast or bacteria, it may be necessary to modify the protein produced therein, for example by phosphorylation or glycosylation of the appropriate sites, in order to obtain the functional TNF-R1-DD ligand protein. Such covalent attachments may be accomplished using known chemical or enzymatic methods.

The TNF-R1-DD ligand protein of the invention may also be expressed as a product of transgenic animals, e.g., as a component of the milk of transgenic cows, goats, pigs, or sheep which are characterized by somatic or germ cells containing a nucleotide sequence encoding the TNF-R1-DD ligand protein.

The TNF-R1-DD ligand protein of the invention may be prepared by culturing transformed host cells under culture conditions suitable to express the recombinant protein. The resulting expressed protein may then be purified from such culture (i.e., from culture medium or cell extracts) using known purification processes, such as gel filtration and ion exchange chromatography. The purification of the TNF-R1-DD ligand protein may also include an affinity column containing the TNF-R death domain or other TNF-R death domain protein; one or more column steps over such affinity resins as concanavalin A-agarose, heparin-toyopearl® or Cibacrom blue 3GA Sepharose®; one or more steps involving hydrophobic interaction chromatography using such resins as phenyl ether, butyl ether, or propyl ether; or immunoaffinity chromatography.

Alternatively, the TNF-R1-DD ligand protein of the invention may also be expressed in a form which will facilitate purification. For example, it may be expressed as a fusion protein, such as those of maltose binding protein (MBP) or glutathione-S-transferase (GST). Kits for expression and purification of such fusion proteins are commercially available from New England BioLab (Beverly, Mass.) and Pharmacia (Piscataway, N.J.), respectively. The TNF-R ligand protein can also be tagged with an epitope and subsequently purified by using a specific antibody directed to such epitope. One such epitope ("Flag") is commercially available from Kodak (New Haven, Conn.).

Finally, one or more reverse-phase high performance liquid chromatography (RP-HPLC) steps employing hydrophobic RP-HPLC media, e.g., silica gel having pendant methyl or other aliphatic groups, can be employed to further purify the TNF-R1-DD ligand protein. Some or all of the foregoing purification steps, in various combinations, can also be employed to provide a substantially homogeneous isolated recombinant protein. The TNF-R1-DD ligand protein thus purified is substantially free of other mammalian proteins and is defined in accordance with the present invention as an "isolated TNF-R1-DD ligand protein."

TNF-R1-DD ligand proteins may also be produced by known conventional chemical synthesis. Methods for constructing the proteins of the present invention by synthetic means are known to those skilled in the art. The synthetically-constructed protein sequences, by virtue of sharing primary, secondary or tertiary structural and/or conformational characteristics with TNF-R1-DD ligand proteins may possess biological properties in common therewith, including TNF-R1-DD ligand protein activity. Thus, they may be employed as biologically active or immunological substitutes for natural, purified TNF-R1-DD ligand proteins in screening of therapeutic compounds and in immunological processes for the development of antibodies.

The TNF-R1-DD ligand proteins provided herein also include proteins characterized by amino acid sequences similar to those of purified TNF-R1-DD ligand proteins but into which modification are naturally provided or deliberately engineered. For example, modifications in the peptide or DNA sequences can be made by those skilled in the art using known techniques. Modifications of interest in the TNF-R1-DD ligand protein sequences may include the replacement, insertion or deletion of a selected amino acid residue in the coding sequence. For example, one or more of the cysteine residues may be deleted or replaced with another amino acid to alter the conformation of the molecule. Mutagenic techniques for such replacement, insertion or deletion are well known to those skilled in the art (see, e.g., U.S. Pat. No. 4,518,584).

Other fragments and derivatives of the sequences of TNF-R1-DD ligand proteins which would be expected to retain TNF-R1-DD ligand protein activity in whole or in part and may thus be useful for screening or other immunological methodologies may also be easily made by those skilled in the art given the disclosures herein. Such modifications are believed to be encompassed by the present invention.

TNF-R1-DD ligand protein of the invention may also be used to screen for agents which are capable of inhibiting or blocking binding of an TNF-R1-DD ligand protein to the death domain of TNF-R, and thus may act as inhibitors of TNF-R death domain binding and/or TNF activity. Binding assays using a desired binding protein, immobilized or not, are well known in the art and may be used for this purpose using the TNF-R1-DD ligand protein of the invention. Examples 1 and 3 describe examples of such assays. Appropriate screening assays may be cell-based or cell-free. Alternatively, purified protein based screening assays may be used to identify such agents. For example, TNF-R1-DD ligand protein may be immobilized in purified form on a carrier and binding to purified TNF-R death domain may be measured in the presence and in the absence of potential inhibiting agents. A suitable binding assay may alternatively employ purified TNF-R death domain immobilized on a carrier, with a soluble form of a TNF-R1-DD ligand protein of the invention. Any TNF-R1-DD ligand protein may be used in the screening assays described above.

In such a screening assay, a first binding mixture is formed by combining TNF-R death domain protein and TNF-R1-DD ligand protein, and the amount of binding in the first binding mixture ($B_0$) is measured. A second binding mixture is also formed by combining TNF-R death domain protein, TNF-R1-DD ligand protein, and the compound or agent to be screened, and the amount of binding in the second binding mixture (B) is measured. The amounts of binding in the first and second binding mixtures are compared, for example, by performing a $B/B_0$ calculation. A compound or agent is considered to be capable of inhibiting TNF-R death domain binding if a decrease in binding in the second binding mixture as compared to the first binding mixture is observed. The formulation and optimization of binding mixtures is within the level of skill in the art. Such binding mixtures may also contain buffers and salts necessary to enhance or to optimize binding, and additional control assays may be included in the screening assay of the invention.

Alternatively, appropriate screening assays may be cell based. For example, the binding or interaction between an TNF-R ligand protein and the TNF-R death domain can be measured in yeast as described below in Examples 1 and 3.

Compounds found to reduce, preferably by at least about 10%, more preferably greater than about 50% or more, the binding activity of TNF-R1-DD ligand protein to TNF-R death domain may thus be identified and then secondarily screened in other binding assays, including in vivo assays. By these means compounds having inhibitory activity for TNF-R death domain binding which may be suitable as anti-inflammatory agents may be identified.

Isolated TNF-R1-DD ligand protein may be useful in treating, preventing or ameliorating inflammatory conditions and other conditions, such as cachexia, autoimmune disease, graft versus host reaction, osteoporosis, colitis, myelogenous leukemia, diabetes, wasting, and atherosclerosis. Isolated TNF-R1-DD ligand protein may be used itself as an inhibitor of TNF-R death domain binding or to design inhibitors of TNF-R death domain binding. Inhibitors of binding of TNF-R1-DD ligand protein to the TNF-R death domain ("TNF-R intracellular binding inhibitors") are also useful for treating such conditions.

The present invention encompasses both pharmaceutical compositions and therapeutic methods of treatment or use which employ isolated TNF-R1-DD ligand protein and/or binding inhibitors of TNF-R intracellular binding.

Isolated TNF-R1-DD ligand protein or binding inhibitors (from whatever source derived, including without limitation from recombinant and non-recombinant cell lines) may be used in a pharmaceutical composition when combined with a pharmaceutically acceptable carrier. Such a composition may also contain (in addition to TNF-R1-DD ligand protein or binding inhibitor and a carrier) diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. The pharmaceutical composition of the invention may also contain cytokines, lymphokines, or other hematopoietic factors such as M-CSF, GM-CSF, TNF, IL-2, IL-3, IL-4, IL-5, IL-6, IL-7, IL-8, IL-9, G-CSF, Meg-CSF, stem cell factor, and erythropoietin. The pharmaceutical composition may further contain other anti-inflammatory agents. Such additional factors and/or agents may be included in the pharmaceutical composition to produce a synergistic effect with isolated TNF-R1-DD ligand protein or binding inhibitor, or to minimize side effects caused by the isolated TNF-R1-DD ligand protein or binding inhibitor. Conversely, isolated TNF-R1-DD ligand protein or binding inhibitor may be included in formulations of the particular cytokine, lymphokine, other hematopoietic factor, thrombolytic or anti-thrombotic factor, or anti-inflammatory agent to minimize side effects of the cytokine, lymphokine, other hematopoietic factor, thrombolytic or anti-thrombotic factor, or anti-inflammatory agent.

The pharmaceutical composition of the invention may be in the form of a liposome in which isolated TNF-R1-DD ligand protein or binding inhibitor is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

As used herein, the term "therapeutically effective amount" means the total amount of each active component of the pharmaceutical composition or method that is sufficient to show a meaningful patient benefit, i.e., treatment, healing, prevention or amelioration of an inflammatory response or condition, or an increase in rate of treatment, healing, prevention or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

In practicing the method of treatment or use of the present invention, a therapeutically effective amount of isolated TNF-R1-DD ligand protein or binding inhibitor is administered to a mammal having a condition to be treated. Isolated TNF-R1-DD ligand protein or binding inhibitor may be administered in accordance with the method of the invention either alone or in combination with other therapies such as treatments employing cytokines, lymphokines or other hematopoietic factors. When co-administered with one or more cytokines, lymphokines or other hematopoietic factors, isolated TNF-R1-DD ligand protein or binding inhibitor may be administered either simultaneously with the cytokine(s), lymphokine(s), other hematopoietic factor(s), thrombolytic or anti-thrombotic factors, or sequentially. If administered sequentially, the attending physician will decide on the appropriate sequence of administering isolated TNF-R1-DD ligand protein or binding inhibitor in combination with cytokine(s), lymphokine(s), other hematopoietic factor(s), thrombolytic or anti-thrombotic factors.

Administration of isolated TNF-R1-DD ligand protein or binding inhibitor used in the pharmaceutical composition or to practice the method of the present invention can be carried out in a variety of conventional ways, such as oral ingestion, inhalation, or cutaneous, subcutaneous, or intravenous injection. Intravenous administration to the patient is preferred.

When a therapeutically effective amount of isolated TNF-R1-DD ligand protein or binding inhibitor is administered orally, isolated TNF-R1-DD ligand protein or binding inhibitor will be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% isolated TNF-R1-DD ligand protein or binding inhibitor, and preferably from about 25 to 90% isolated TNF-R1-DD ligand protein or binding inhibitor. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of isolated TNF-R1-DD ligand protein or binding inhibitor, and preferably from about 1 to 50% isolated TNF-R1-DD ligand protein or binding inhibitor.

When a therapeutically effective amount of isolated TNF-R1-DD ligand protein or binding inhibitor is administered by intravenous, cutaneous or subcutaneous injection, isolated TNF-R1-DD ligand protein or binding inhibitor will be in the form of a pyrogen-free, parenterally acceptable aqueous solution. The preparation of such parenterally acceptable protein solutions, having due regard to pH, isotonicity, stability, and the like, is within the skill in the art. A preferred pharmaceutical composition for intravenous, cutaneous, or subcutaneous injection should contain, in addition to isolated TNF-R1-DD ligand protein or binding inhibitor, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of isolated TNF-R1-DD ligand protein or binding inhibitor in the pharmaceutical composition of the present invention will depend upon the nature and severity of the condition being treated, and on the nature of prior treatments which the patient has undergone. Ultimately, the attending physician will decide the amount of isolated TNF-R1-DD ligand protein or binding inhibitor with which to treat each individual patient. Initially, the attending physician will administer low doses of isolated TNF-R1-DD ligand protein or binding inhibitor and observe the patient's response. Larger doses of isolated TNF-R1-DD ligand protein or binding inhibitor may be administered until the optimal therapeutic effect is obtained for the patient, and at that point the dosage is not increased further. It is contemplated that the various pharmaceutical compositions used to practice the method of the present invention should contain about 0.1 µg to about 100 mg of isolated TNF-R1-DD ligand protein or binding inhibitor per kg body weight.

The duration of intravenous therapy using the pharmaceutical composition of the present invention will vary, depending on the severity of the disease being treated and the condition and potential idiosyncratic response of each individual patient. It is contemplated that the duration of each application of the isolated TNF-R1-DD ligand protein or binding inhibitor will be in the range of 12 to 24 hours of continuous intravenous administration. Ultimately the attending physician will decide on the appropriate duration of intravenous therapy using the pharmaceutical composition of the present invention.

Isolated TNF-R1-DD ligand protein of the invention may also be used to immunize animals to obtain polyclonal and monoclonal antibodies which specifically react with the TNF-R1-DD ligand protein and which may inhibit TNF-R death domain binding. Such antibodies may be obtained using either the entire TNF-R1-DD ligand protein or fragments of TNF-R1-DD ligand protein as an immunogen. The peptide immunogens additionally may contain a cysteine residue at the carboxyl terminus, and are conjugated to a hapten such as keyhole limpet hemocyanin (KLH). Methods for synthesizing such peptides are known in the art, for example, as in R. P. Merrifield, J. Amer. Chem. Soc. 85, 2149–2154 (1963); J. L. Krstenansky, et al., FEBS Lett. 211, 10 (1987).

Monoclonal antibodies binding to TNF-R1-DD ligand protein or to complex carbohydrate moieties characteristic of the TNF-R1-DD ligand glycoprotein may be useful diagnostic agents for the immunodetection of TNF-R ligand protein.

Neutralizing monoclonal antibodies binding to TNF-R1-DD ligand protein or to complex carbohydrates characteristic of TNF-R1-DD ligand glycoprotein may also be useful therapeutics for both inflammatory conditions and also in the treatment of some forms of cancer where abnormal expression of TNF-R1-DD ligand protein is involved. These neutralizing monoclonal antibodies are capable of blocking the signaling function of the TNF-R1-DD ligand protein. By blocking the binding of TNF-R1-DD ligand protein, certain biological responses to TNF are either abolished or markedly reduced. In the case of cancerous cells or leukemic cells, neutralizing monoclonal antibodies against TNF-R1-DD ligand protein may be useful in detecting and preventing the metastatic spread of the cancerous cells, which may be mediated by the TNF-R1-DD ligand protein.

Due to the similarity of their sequences to the insulin growth factor binding protein ("IGFBP-5") and fragments thereof which bind to the TNF-R death domain are proteins having TNF-R1-DD ligand protein activity as defined herein. As a result, they are also useful in pharmaceutical compositions, for treating inflammatory conditions and for inhibiting TNF-R death domain binding as described above for TNF-R1-DD ligand proteins generally.

EXAMPLE 1

Cloning of TNF-R Death Domain Ligand Protein Encoding Polynucleotide

A yeast genetic selection method, the "interaction trap" [Gyuris et al, Cell 75:791–803, 1993, which is incorporated herein by reference], was used to screen WI38 cell cDNA libraries (preparation, see below) for proteins that interact with the death domain of the P55 type 1 TNF receptor (TNF-R1-DD). A polynucleotide encoding amino acids 326 to 413 of the P55 type TNF receptor, TNF-R1-DD, was obtained via the polymerase chain reaction (PCR) using a grafting method. This TNF-R1-DD DNA was then cloned into pEG202 by BamHI and SalI sites, generating the bait plasmid, pEG202-TNF-R1-DD. This plasmid contains the HIS3 selectable marker, and expression of the bait, the LexA-TNF-R1-DD fusion protein, is from the strong constitutive ADH1 promoter. To create the reporter strain carrying the bait protein, yeast strain EGY48, containing the reporter sequence LexAop-Leu2 in place of the chromosomal LEU2, was transformed with pEG202-TNF-R1-DD and pSH18–34 (Ura+), which carries another reporter sequence, LexAop-lacZ. For screening cDNAs encoding proteins that interact with TNF-R1-DD, the expression vector pJG4-5 (TRP1), containing the WI38 cell cDNA library (see below for the cDNA library construction), was transformed into the above strain (EGY48/pEG202-TNF-R1-DD/pSH18-34) according to the method described by Gietz et al., Nucleic Acids Res., 20:1425 (1992).

cDNA Library Construction

WI38 cell cDNA library: Double stranded cDNA was prepared from 3 ug of WI38 mRNA using reagents provided by the Superscript Choice System (Gibco/BRL, Gaithersberg, Md.) with the following substitutions: the first strand synthesis was primed using an oligo dT/XhoI primer/linker, and the dNTP mix was substituted with a mix containing methyl dCTP (Stratagene, LaJolla, Calif.). The cDNA was modified at both ends by addition of an EcoRI/NotI/SalI adapter linker and subsequently digested with XhoI. This produced cDNA molecules possessing an EcoRI/NotI/SalI overhang at the 5' end of the gene and an XhoI overhang at the 3' end. These fragments were then ligated into the yeast expression/fusion vector pJG4-5 (Gyuris et al., Cell, 75, 791–803, 1993), which contains at its amino terminus, the influenza virus HA1 epitope tag, the B42 acidic transcription activation domain, and the SV40 nuclear localization signal, all under the control of the galactose-dependent GAL1 promoter. The resulting plasmids were then electroporated into DH10B cells (Gibco/BRL). A total of $7.1\times10^6$ colonies were plated on LB plates containing 100 ug/ml of ampicillin. These *E. coli* were scraped, pooled, and a large scale plasmid prep was performed using the Wizard Maxi Prep kit (Promega, Madison, Wis.), yielding 3.2 mg of supercoiled plasmid DNA.

WI38 Cell cDNA Screening Results $1\times10^6$ transformants were obtained on glucose $Ura^-His^-Trp^-$ plates. These transformants were pooled and resuspended in a solution of 65% glycerol, 10 mM Tris-HCl (pH 7.5), 10 mM $MgCl_2$ and stored at −80° C. in 1 mL aliquots. For screening purposes, aliquots of these were diluted 10-fold into $Ura^-His^-Trp^-$ CM dropout gal/raff medium (containing 2% galactose, 1% raffinose), which induces the expresssion of the library encoded proteins, and incubated at 30° C. for 4 hours. $12\times10^6$ colony forming units (CFUs)

were then plated on standard 10 cm galactose X-Gal Ura⁻His⁻Trp⁻ Leu plates at a density of 2×10⁵ CFU/plate. After three days at 30° C., about 1,000 colonies were formed (Leu⁺) and of those, sixty-four colonies were LacZ⁺. In order to test if the Leu⁺/LacZ⁺ phenotype was due to the library-encoded protein, the galactose dependency of the phenotype was tested. Expression of the library-encoded proteins was turned off by growth on glucose Ura⁻His⁻Trp⁻ master plates and then retested for galactose-dependency on glucose Ura⁻His⁻Trp⁻Leu⁻, galactose Ura⁻His⁻Trp⁻Leu⁻, glucose X-Gal Ura⁻His⁻Trp⁻, and galactose X-Gal Ura⁻His⁻Trp⁻ plates. Of these, 32 colonies showed galactose-dependent growth on Leu⁻ plates and galactose-dependent blue color on X-Gal-containing medium (LacZ⁺ phenotype). Total yeast DNA was prepared from these colonies according to the method described previously (Hoffman and Winston, 1987). In order to analyze the cDNA sequences, PCR reactions were performed using the above yeast DNA as a template and oligo primers specific for the vector pJG4-5, flanking the cDNA insertion point. PCR products were purified (Qiagen PCR purification kit), subjected to restriction digest with the enzyme HaeIII, run on 1.8% agarose gels, and the restriction patterns compared. Similar and identical restriction patterns were grouped and representatives of each group were sequenced and compared to Genbank and other databases to identify any sequence homologies.

One clone of unique sequence ("2DD") and three clones with identical sequence ("3DD") were isolated and showed no signficant sequence homologies compared to Genbank and other databases. Additionally, four other clones ("20DD") with identical sequence to a portion of human insulin-like growth factor binding protein-5 (Shunichi Shimasaki et al., J. Biol. Chem. 266:10646–10653 (1991)) were isolated. The clones "2DD," "3DD" and "20DD" were chosen for further analysis. Library vector pJG4-5 containing these clones sequences were rescued from yeast by transforming the total yeast DNAs into the E. coli strain KC8 and selecting for growth on Trp-ampicillin plates. These putative TNFR1 interacting proteins were then tested further for specificity of interaction with the TNF-R1-DD by the reintroduction of JG4-5 clone into EGY48 derivatives containing a panel of different baits, including bicoid, the cytoplasmic domain of the IL-1 receptor, and TNF-R1-DD. The above clones were found to interact only with the TNF-R1-DD. The interaction between these clones and TNF-R1-DD was thus judged to be specific.

U937 cDNA Screening Results

A U937 cDNA library was also constructed and screened as described above. 1,020 Leu+ colonies were found and of those, 326 colonies were also LacZ+. 62 colonies of these Leu+/LacZ+ colonies showed a galactose-dependent phenotype. One of these clones, 1TU, encodes a novel sequence. Interestingly, two clones, 15TU and 27TU, encode related or identical sequences, except that 27TU contains about 864 additional nucleotides (or about 288 amino acids) at the 5' end. 15/27TU also encode a novel sequence.

EXAMPLE 2

Expression of the TNF-R1-DD Ligand Protein cDNAs encoding TNF-R intracellular ligand proteins were released from the pJG4-5 vector with the appropriate restriction enzymes. For example, EcoRI and XhoI or NotI and XhoI were used to release cDNA from clone 2DD and clone 20DD. Where the restriction sites were also present in the internal sequence of the cDNA, PCR was performed to obtain the cDNA. For example, the cDNA fragment encoding "clone 3DD" was obtained through PCR due to the presence of an internal XhoI site. These cDNAs were then cloned into various expression vectors. These included pGEX (Pharmacia) or pMAL (New England Biolabs) for expression as a GST (Glutathione-S-transferase) or MBP (maltose binding protein) fusion protein in E. coli, a pED-based vector for mammalian expression, and pVL or pBlueBacHis (Invitrogen) for baculovirus/insect expression. For the immunodetection of TNF-R intracellular ligand expression in mammalian cells, an epitope sequence, "Flag," was inserted into the translational start site of the pED vector, generating the pED-Flag vector. cDNAs were then inserted into the pED-Flag vector. Thus, the expression of cDNA from pED-Flag yields a protein with an amino terminal Met, followed by the "Flag" sequence, Asp-Tyr-Lys-Asp-Asp-Asp-Asp-Lys. Standard DEAE-Dextran or lipofectamine methods were used to transfect COS or CHO dukx cells. Immunodetection of Flag-tagged proteins was achieved using the M2 antibody (Kodak). Moreover, an immunoaffinity column using the M2 antibody, followed by elution with the "Flag" peptide, can be used for the rapid purification of the flag-tagged protein. Similarly, affinity purification of GST-, MBP- or His-tagged fusion proteins can be performed using glutathione, amylose, or nickel columns. Detailed purification protocols are provided by the manufacturers. For many fusion proteins, the TNF-R intracellular ligand can be released by the action of thrombin, factor Xa, or enterokinase cleavage. In the case where highly purified material is required, standard purification procedures, such as ion-exchange, hydrophobic, and gel filtration chromatography will be applied in addition to the affinity purification step.

Figure 2:
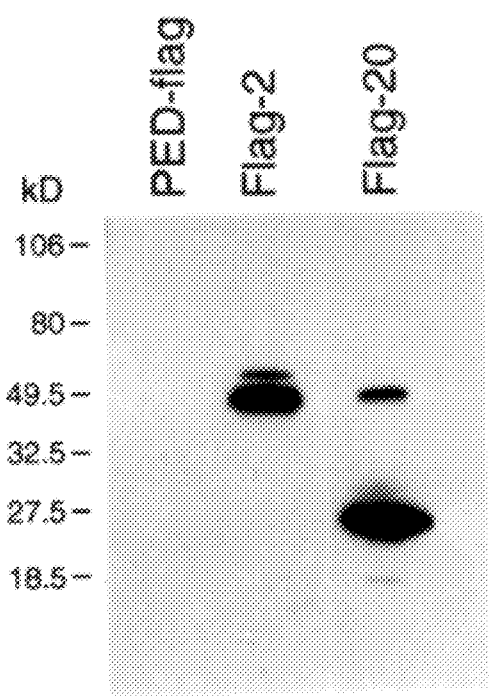

FIGS. 1 and 2 depict autoradiographs demonstrating the expression of TNF-R1-DD ligand proteins in yeast and mammalian cells. FIG. 1 shows the results of expression of isloated clones of the present invention in yeast. EGY48 was transformed with pJG4-5 containing clone 2DD, 3DD or 20DD. Cells were then grown overnight in the galactose/raffinose medium. Cell lysates were prepared and subject to 4–20% SDS gel electrophoresis, followed by Western blot analysis using anti-HA antibody (12CA5, Boehringer Mannheim, Indianapolis, Ind.). FIG. 2 shows the results of expression of Flag-2DD and Flag-20DD in COS cells. COS cells were transfected with either pED-Flag (Vector control), Flag-2DD or Flag-20DD plasmid by the lipofectamine method. Thirty μg of each cell lysate were prepared and subjected to 4–20% SDS gel electrophoresis, followed by Western blot analysis using M2 antibody (Kodak). The bands in the Flag-2DD and Flag-20DD lanes indicate significant expression of the respective TNF-R1-DD ligand proteins.

EXAMPLE 3

Assays of TNF-R Death Domain Binding

Two different methods were used to assay for TNF-R1-DD ligand protein activity. The first assay measures binding in the yeast strain in "interaction trap," the system used here to screen for TNF-R1-DD interacting proteins. In this system, the expression of reporter genes from both LexAop-Leu2 and LexAop-LacZ relies on the interaction between the bait protein, in this case TNF-R1DD, and the prey, the TNF-R intracellular ligand. Thus, one can measure the strength of the interaction by the level of Leu2 or LacZ expression. The most simple method is to measure the activity of the LacZ encoded protein, β-galactosidase. This activity can be judged by the degree of blueness on the X-Gal containing medium or filter. For the quantitative measurement of β-galactosidase activity, standard assays can be found in "Methods in Yeast Genetics" Cold Spring Harbor, New York, 1990 (by Rose, M. D., Winston, F., and Hieter, P.).

The second assay for measuring binding is a cell-free system. An example of a typical assay is described below. Purified GST-TNF-R1-DD fusion protein (2 ug) was mixed with amylose resins bound with a GST-TNF-R1-DD intracellular ligand for 2 hour at 4° C. The mixture was then centrifuged to separate bound (remained with the beads) and unbound (remained in the supernatant) GST-TNF-R1-DD. After extensive washing, the bound GST-TNF-R1-DD was eluted with maltose and detected by Western blot analysis using a GST antibody. The TNF-R1-DD or the intracellular ligand can also be immobilized on other solid supports, such as on plates or fluorobeads. The binding can then be measured using ELISA or SPA (scintillation proximity assay).

EXAMPLE 4

Characterization of TNF-R Death Domain Ligand Protein

Mapping the Interaction Site in TNF-R1

Many of the key amino acids for TNF-R signaling have been determined by site-directed mutagenesis (Tataglia et al., Cell 74:845–853 (1993). These amino acids are conserved between TNF-R and the Fas antigen, which is required for mediating cytotoxicity and other cellular responses. In order to test if the TNF-R intracellular proteins interact with these residues, the following mutations were constructed: F345A (substitution of phe at amino acid 345 to Ala), R347A, L351A, F345A/R347A/L351A, E369A, W378A and I408A. The ability of the mutant protein to interact with the intracellular ligand in the "interaction trap" system was tested.

Effect on the TNF-Mediated Response

The effect of the TNF-R intracellular ligands on the TNF-mediated response can be evaluated in cells overexpressing the ligands. A number of TNF-mediated responses, including transient or prolonged responses, can be measured. For example, TNF-induced kinase activity toward either MBP (myelin basic protein) or the N-terminus (amino acids 1–79) of c-jun can be measured in COS cells or CHO cells either transiently or stably overexpressing clone 2DD, 3DD or clone 20DD. The significance of these ligand proteins in TNF-mediated cytotoxicity and other cellular responses can be measured in L929 or U937 overexpressing cells. Alternatively, other functional assays, such as the induction of gene expression or $PGE_2$ production after prolonged incubation with TNF, can also be used to measure the TNF mediated response. Conversely, the significance of the TNF-R1-DD ligand proteins in TNF signaling can be established by lowering or eliminating the expression of the ligands. These experiments can be performed using antisense expression or transgenic mice.

Enzymatic or Functional Assays

The signal transduction events initiated by TNF binding to its receptor are still largely unknown. However, one major result of TNF binding is the stimulation of cellular serine/threonine kinase activity. In addition, TNF has been shown to stimulate the activity of PC-PLC, $PLA_2$, and sphingomyelinase. Therefore, some of the TNF-R1-DD ligand proteins may possess intrinsic enzymatic activity that is responsible for these activities. Therefore, enzymatic assays can be performed to test this possibility, particularly with those clones that encode proteins with sequence homology to known enzymes. In addition to enzymatic activity, based on the sequence homology to proteins with known function, other functional assays can also be measured.

EXAMPLE 5

Isolation of Full Length Clones

In many cases, cDNAs obtained from the interaction trap method each encode only a portion of the full length protein. For example, based on identity and sequence and the lack of the initiating methionine codon, clones 2DD, 3DD and 20DD apparently do not encode full length proteins. Therefore, it is desirable to isolate full length clones. The cDNAs obtained from the screening, such as clone 2DD, are used as probes, and the cDNA libraries described herein, or alternatively phage cDNA libraries, are screened to obtain full length clones in accordance with known methods (see for example, "Molecular Cloning, A Laboratory Manual", by Sambrook et al., 1989 Cold Spring Harbor).

EXAMPLE 6

Antibodies Specific for TNF-R Intracellular Ligand Protein

Antibodies specific for TNF-R intracellular ligand proteins can be produced using purified recombinant protein, as described in Example 2, as antigen. Both polyclonal and monoclonal antibodies will be produced using standard techniques, such as those described in "Antibodies, a Laboratory Manual" by Ed Harlow and David Lane (1988), Cold Spring Harbor Laboratory.

EXAMPLE 7

Characterization of Clones 1TU and 15/27TU

Specificity of Interaction

The specificity of clones 1TU, 15TU and 27TU was tested using a panel of baits. The ability of these clones to bind the TNF-R death domain was compared to their binding to the intracellular domain of the second TNF-R (TNF-R $p75_{IC}$), the entire intracellular domain of TNF-R (TNF-R $p55_{IC}$), the death domain of the fas antigen (which shares 28% identity with TNF-R-DD) ($Fas_{DD}$), the Drosophila transcription factor bicoid, and a region of the IL-1 receptor known to be critical for signalling (IL-$1R_{477-527}$). As shown in Table 1, none of these clones interacted with TNF-R $p75_{IC}$ or $Fas_{DD}$, and only 1TU interacted with bicoid. In contrast, both 1TU and 15TU bound the cytoplasmic domain of the p55 TNF-R, as well as residues 477–527 of the IL-1R. 27TU interacted relatively weakly with these sequences.

TABLE 1

| clone | TNF-$R_{DD}$ | TNF-R $P75_{IC}$ | TNF-R $p55_{IC}$ | $Fas_{DD}$ | bicoid | IL-1R (477–527) |
|---|---|---|---|---|---|---|
| 1TU | +++ | − | +++ | − | ++ | +++ |
| 15TU | +++ | ± | +++ | − | − | ++ |
| 27TU | +++ | − | + | − | − | + |

Interaction with Amino Acids Critical for Signalling

The ability of each clone to interact with four single-site mutations in the TNF-R death domain (each known to abolish signalling) was measured. As shown in Table 2, each of the clones interacted less strongly with the death domain mutants than with the wild type death domain, suggesting that these clones may bind critical residues in vivo.

TABLE 2

| clone | TNF-R$_{DD}$ | F345A | L351A | W378A | I408A |
|---|---|---|---|---|---|
| 1TU | +++ | + | ++ | ++ | + |
| 15TU | +++ | + | + | ++ | ++ |
| 27TU | +++ | + | + | ± | ++ |

Expression of 1TU, 15TU and 27TU

Figure 3A:
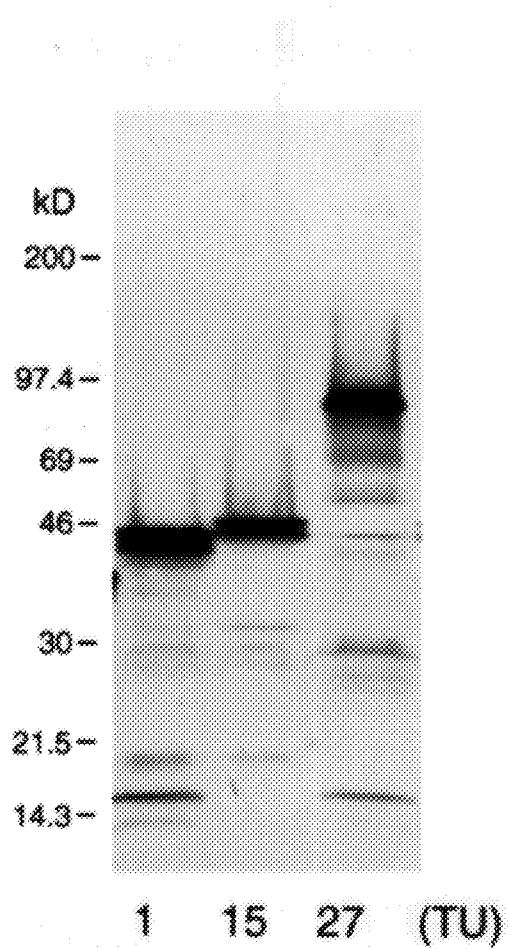
FIG. 3 depicts an autoradiograph demonstrating the expression of clones 1TU, 15TU and 27TU.
Figure 3B:
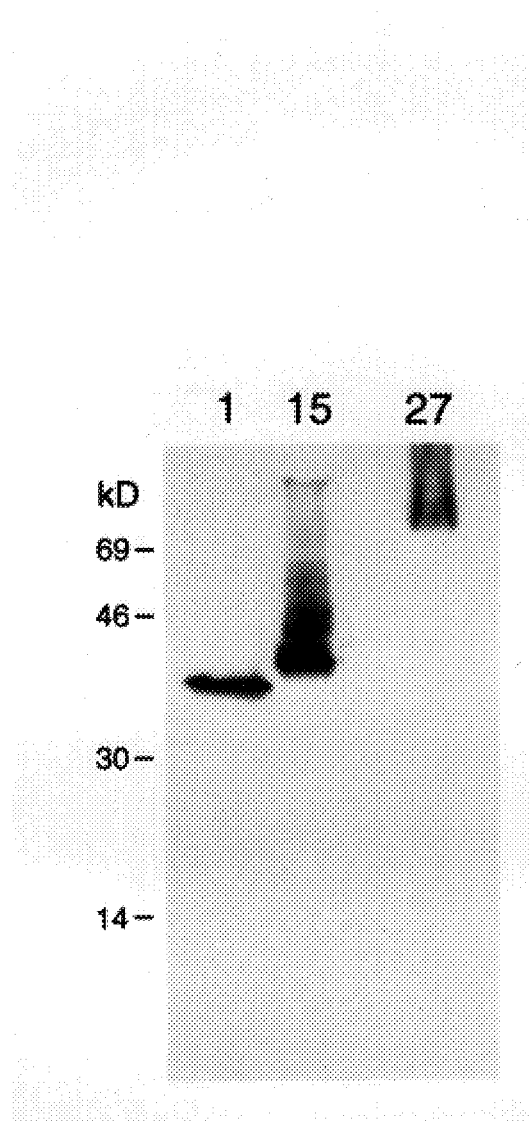

FIG. 3 depicts an autoradiograph demonstrating the expression of clones 1TU, 15TU and 27TU in yeast (A) and COS cells (B).

In (A): EGY48 was transformed with pJG4-5 containing clones 1TU, 15TU or 27TU. Cells were then grown overnight in galactose/raffinose medium. Cell lysates were prepared and subjected to 4–20% SDS gel electrophoresis, followed by Western blot analysis using anti-HA antibody (12CA5, Boehringer Mannheim).

In (B): COS cells were transfected with pED-Flag containing clones 1TU, 15TU and 27TU. Cell lysates were prepared and analyzed by Western blot using anti-Flag antibody (M2, Kodak).

Specific Binding of 1TU and 27TU to TNF-R1-DD

Figure 4:
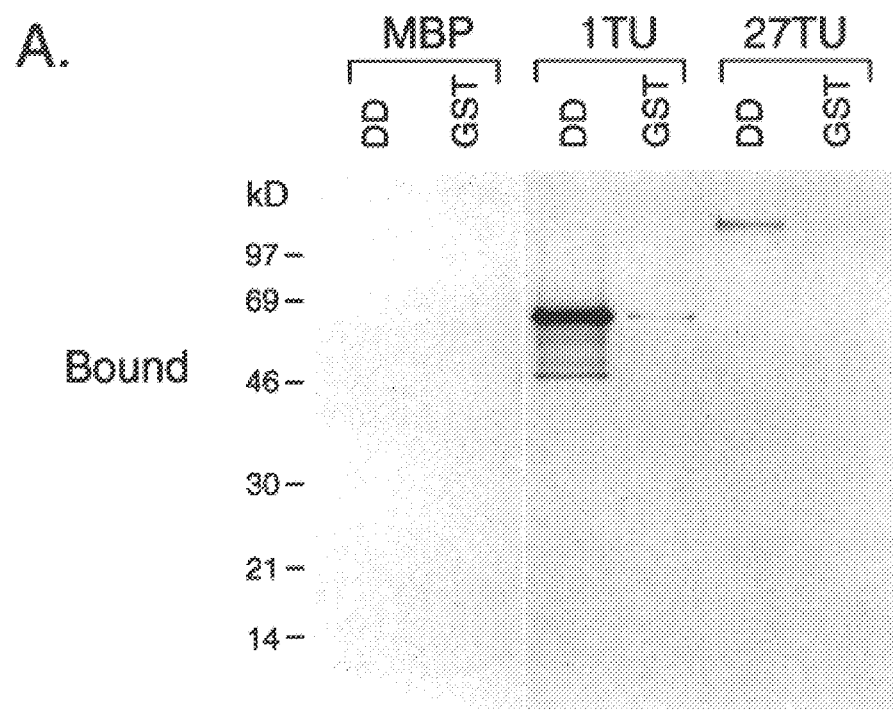
FIG. 4 demonstrates the binding of 1TU and 27TU to TNF-R1-DD. MBP, MBP-1TU or MBP-27TU (3 μg) was incubated with glutathione beads containing 3 μg of either GST or GST-TNF-R1-DD in 100 μl of binding buffer (0.2% Triton, 20 mM Tris pH 7.5, 140 mM NaCl, 0.1 mM EDTA, 10 mM DTT and 5% glycerol). The reaction ws performed at 4° C. for 2 hours and centrifuged to remove unbound fraction (Unbound). The beads were then washed with 500 μl binding buffer four times and resuspended into SDS-sample buffer (Bound). These samples were analyzed by Western blot using anti-MBP antibody (New England Biolab).
Figure 4:
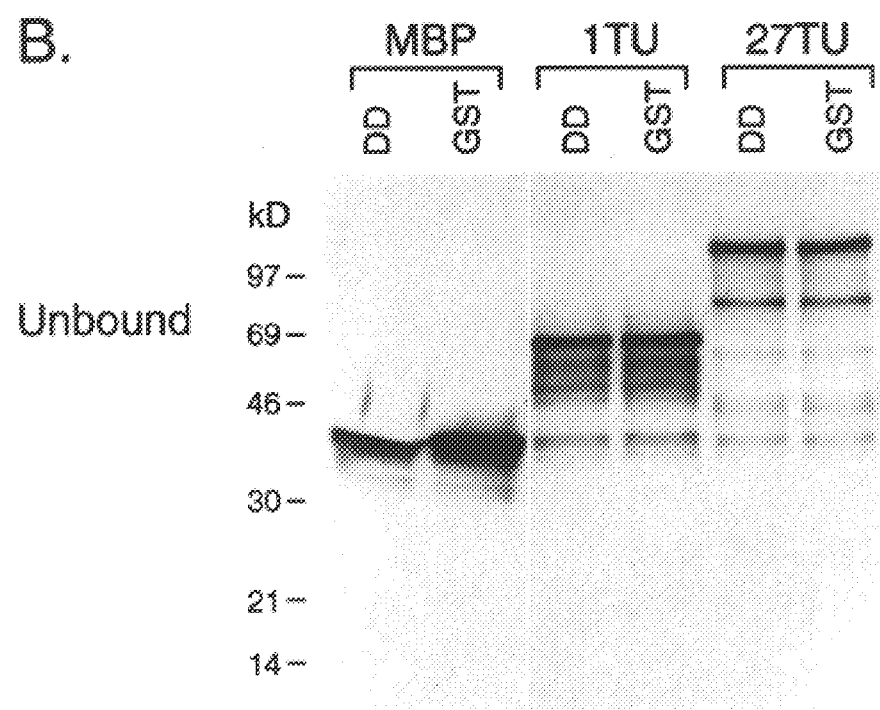

The interaction of 1TU and 27TU with TNF-R1-DD was tested using purified bacterially expressed fusion proteins. As shown in FIG. 4, MBP fusion proteins containing 1TU or 27TU bound only to TNF-R1-DD expressed as a GST fusion protein, but not to GST protein alone. In the control experiment, MBP protein did not bind either GST or GST/TNF-R1-DD. These results indicate that 1TU and 27TU bound specifically to the TNF-R1 death domain in vitro, confirming the data obtained in the interaction trap.

15TU and 27TU Activation of JNK Activity

Figure 5:
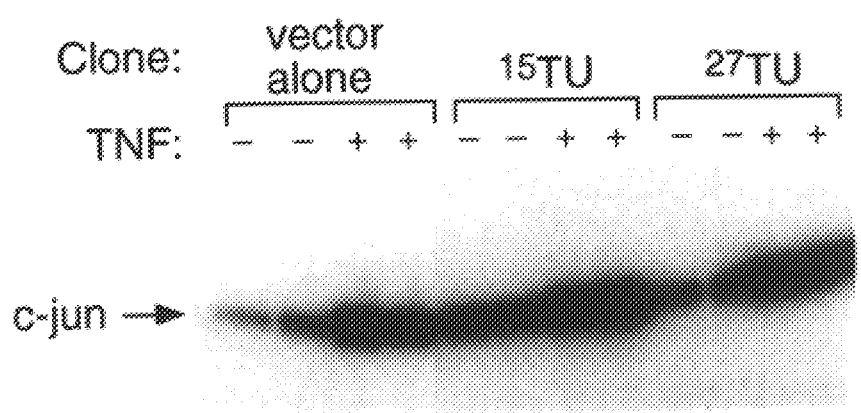
FIG. 5 demonstrates the ability of 15TU and 27TU to activate the JNK pathway. COS cells were contransfected with HA-tagged JNK1 and clones 15tu or 27TU. Cells were left untreated or treated for 15 min with 50 ng/ml TNF, and HA-JNK1 was immunoprecipitated with anti-HA antibody. JNK activity was measured in an in vitro kinase assay using GST-c-jun (amino acids 1–79) as substrate, and reactions were electrophoresed on SDS-PAGE.

The jun N-terminal kinase (JNK) is normally activated within 15 min of TNF treatment in COS cells. 15TU and 27TU were cotransfected with an epitope tagged version of JNK, HA-JNK, in duplicate. After TNF treatment, JNK was immunoprecipitated with anti-HA antibody and JNK activity was measured in immunoprecipitation kinase assays, using GST-c-jun (amino acids 1–79) as substrate). Reactions were electrophoresed on SDS-PAGE. As shown in FIG. 5, transfection of 15TU and 27TU, but not vector alone, into COS cells activated JNK even in the absence of TNF, suggesting that these clones are involved in signal transduction of TNF and the pathway leading to JNK activation in vivo.

EXAMPLE 8

Isolation, Expression and Assay of Clone 3TW

Figure 6:
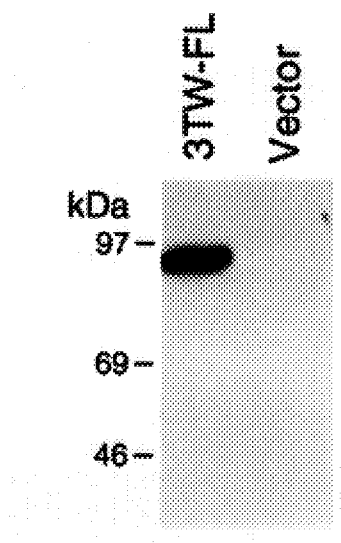
FIG. 6 is an autoradiograph of an SDS-PAGE gel of conditioned media from COS cells transfected with clone 3TW.

Clone 3TW was isolated from the WI38 cDNA library using clone 3DD as a porbe. Clone 3TW was expressed. FIG. 6 is an autoradiograph which demonstrates expression of 3TW (indicated by arrow).

Figure 7:
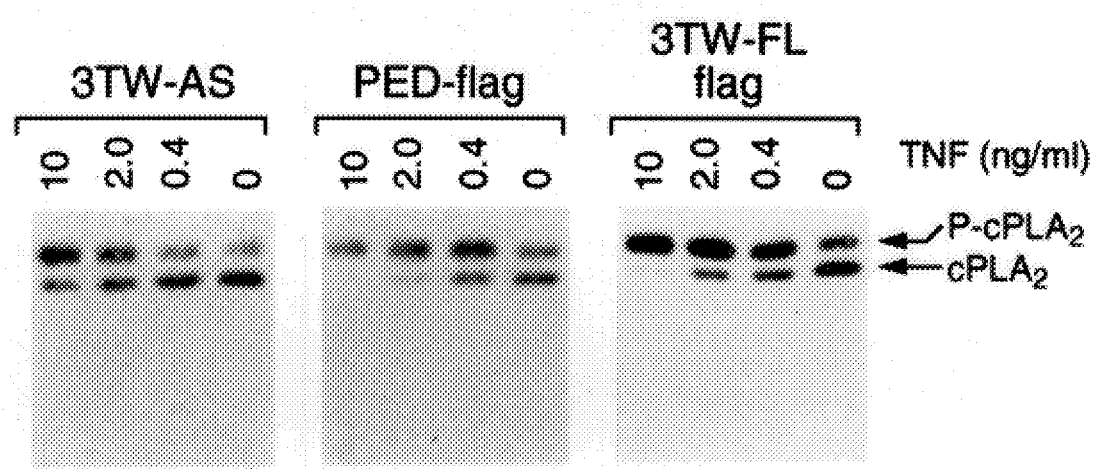
FIG. 7 is an autoradiograph which demonstrates that an antisense oligonucleotide derived from the sequence of clone 3TW inhibits TNF-induced cPLA$_2$ phosphorylation.

An antisense oligonucleotide was derived from the sequence of clone 3TW. The antisense oligonucleotide was assayed to determine its ability to inhibit TNF-induced cPLA$_2$ phosphorylation. FIG. 7 depicts the results of that experiment. Activity of the anitsense oligonucleotide (3TWAS) was compared with the full-length clone (3TWFL), Flag-3TW full length (3TWFLflag) and pED-flag vector (pEDflag). The antisense oligonucleotide inhibited phosphorylation.

What is claimed is:

1. A composition comprising a protein having TNF-R1-DD ligand protein activity, wherein said protein comprises an amino acid sequence selected from the group consisting of:
   (a) the amino acid sequence of SEQ ID NO:2; and
   (b) fragments of the amino acid sequence of SEQ ID NO:2 having TNF-R1-DD ligand protein activity; said protein being substantially free from other mammalian proteins.

2. The composition of claim 1, further comprising a pharmaceutically acceptable carrier.

3. TNF-R1-DD ligand protein produced according to a method comprising:
   (a) transforming a host cell with a composition comprising an isolated polynucleotide encoding the protein of claim 1, wherein the polynucleotide is operably linked to an expression control sequence;
   (b) growing a culture of the host cell in a suitable culture medium; and
   (c) purifying the protein of claim 1 from the culture.

4. TNF-R1-DD ligand protein produced according to the method of claim 3, wherein the host cell is a mammalian cell.

5. The composition of claim 1 wherein said protein comprises the amino acid sequence of SEQ ID NO:2.

6. A method of identifying an inhibitor of TNF-R death domain binding which comprises:
   (a) combining an TNF-R death domain protein with a composition comprising a protein having TNF-R1-DD ligand protein activity, wherein said protein comprises an amino acid sequence selected from the group consisting of:
      (i) the amino acid sequence of SEQ ID NO:16; and
      (ii) fragments of the amino acid sequence of SEQ ID NO:16 having TNF-R1-DD ligand protein activity, the fragments comprising an amino acid sequence not present in SEQ ID NO:12,
   said combination forming a first binding mixture;
   (b) measuring the amount of binding between the TNF-R death domain protein and the TNF-R1-DD ligand protein in the first binding mixture;
   (c) combining a compound with the TNF-R death domain protein and an TNF-R1-DD ligand protein to form a second binding mixture;
   (d) measuring the amount of binding in the second binding mixture; and
   (e) comparing the amount of binding in the first binding mixture with the amount of binding in the second binding mixture;
wherein the compound is capable of inhibiting TNF-R death domain binding when a decrease in the amount of binding of the second binding mixture occurs.

7. A composition comprising a protein having TNF-R1-DD ligand protein activity, wherein said protein comprises an amino acid sequence selected from the group consisting of:
  (a) the amino acid sequence of SEQ ID NO:12; and
  (b) fragments of the amino acid sequence of SEQ ID NO:12 having TNF-R1-DD ligand protein activity;
said protein being substantially free from other mammalian proteins.

8. The composition of claim 7 wherein said protein comprises the amino acid sequence of SEQ ID NO:12.

9. The composition of claim 7, further comprising a pharmaceutically acceptable carrier.

10. TNF-R1-DD ligand protein produced according to a method comprising:
  (a) transforming a host cell with a composition comprising an isolated polynucleotide encoding the protein of claim 7, wherein the polynucleotide is operably linked to an expression control sequence;
  (b) growing a culture of the host cell in a suitable culture medium; and
  (c) purifying the protein of claim 7 from the culture.

11. TNF-R1-DD ligand protein produced according to the method of claim 10, wherein the host cell is a mammalian cell.

12. A composition comprising a protein having TNF-R1-DD ligand protein activity, wherein said protein comprises an amino acid sequence selected from the group consisting of:
  (a) the amino acid sequence of SEQ ID NO:16; and
  (b) fragments of the amino acid sequence of SEQ ID NO:16 having TNF-R1-DD ligand protein activity;
said protein being substantially free from other mammalian proteins.

13. The composition of claim 12, wherein said protein comprises the amino acid sequence of SEQ ID NO:16.

14. The composition of claim 12, further comprising a pharmaceutically acceptable carrier.

15. TNF-R1-DD ligand protein produced according to a method comprising:
  (a) transforming a host cell with a composition comprising an isolated polynucleotide encoding the protein of claim 12, wherein the polynucleotide is operably linked to an expression control sequence;
  (b) growing a culture of the host cell in a suitable culture medium; and
  (c) purifying the protein of claim 12 from the culture.

16. TNF-R1-DD ligand protein produced according to the method of claim 15, wherein the host cell is a mammalian cell.

* * * * *

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
        ( A ) LENGTH: 2158 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 2..1231

( x i ) SEQUENCE DESCRIPTION: SEQ ID NO:1:

```
C AGC AAT GCA GGT GAT GGA CCA GGT GGC GAG GGC AGT GTT CAC CTG         46
  Ser Asn Ala Gly Asp Gly Pro Gly Gly Glu Gly Ser Val His Leu
   1               5                  10                  15

GCA AGC TCT CGG GGC ACT TTG TCT GAT AGT GAA ATT GAG ACC AAC TCT       94
Ala Ser Ser Arg Gly Thr Leu Ser Asp Ser Glu Ile Glu Thr Asn Ser
                  20                  25                  30

GCC ACA AGC ACC ATC TTT GGT AAA GCC CAC AGC TTG AAG CCA AGC ATA      142
Ala Thr Ser Thr Ile Phe Gly Lys Ala His Ser Leu Lys Pro Ser Ile
              35                  40                  45
```

| | | | | | | | | | | | | | | | | |
|---|---|---|---|---|---|---|---|---|---|---|---|---|---|---|---|---|
| AAG | GAG | AAG | CTG | GCA | GGC | AGC | CCC | ATT | CGT | ACT | TCT | GAA | GAT | GTG | AGC | 190 |
| Lys | Glu | Lys | Leu | Ala | Gly | Ser | Pro | Ile | Arg | Thr | Ser | Glu | Asp | Val | Ser | |
| | | 50 | | | | 55 | | | | | 60 | | | | | |
| CAG | CGA | GTC | TAT | CTC | TAT | GAG | GGA | CTC | CTA | GGC | AAA | GAG | CGT | TCT | ACT | 238 |
| Gln | Arg | Val | Tyr | Leu | Tyr | Glu | Gly | Leu | Leu | Gly | Lys | Glu | Arg | Ser | Thr | |
| | 65 | | | | | 70 | | | | | 75 | | | | | |
| TTA | TGG | GAC | CAA | ATG | CAA | TTC | TGG | GAA | GAT | GCC | TTC | TTA | GAT | GCT | GTG | 286 |
| Leu | Trp | Asp | Gln | Met | Gln | Phe | Trp | Glu | Asp | Ala | Phe | Leu | Asp | Ala | Val | |
| 80 | | | | | 85 | | | | | 90 | | | | | 95 | |
| ATG | TTG | GAG | AGA | GAA | GGG | ATG | GGT | ATG | GAC | CAG | GGT | CCC | CAG | GAA | ATG | 334 |
| Met | Leu | Glu | Arg | Glu | Gly | Met | Gly | Met | Asp | Gln | Gly | Pro | Gln | Glu | Met | |
| | | | | 100 | | | | | 105 | | | | | 110 | | |
| ATC | GAC | AGG | TAC | CTG | TCC | CTT | GGA | GAA | CAT | GAC | CGG | AAG | CGC | CTG | GAA | 382 |
| Ile | Asp | Arg | Tyr | Leu | Ser | Leu | Gly | Glu | His | Asp | Arg | Lys | Arg | Leu | Glu | |
| | | | 115 | | | | | 120 | | | | | 125 | | | |
| GAT | GAT | GAA | GAT | CGC | TTG | CTG | GCC | ACA | CTT | CTG | CAC | AAC | CTC | ATC | TCC | 430 |
| Asp | Asp | Glu | Asp | Arg | Leu | Leu | Ala | Thr | Leu | Leu | His | Asn | Leu | Ile | Ser | |
| | | 130 | | | | | 135 | | | | | 140 | | | | |
| TAC | ATG | CTG | CTG | ATG | AAG | GTA | AAT | AAG | AAT | GAC | ATC | CGC | AAG | AAG | GTG | 478 |
| Tyr | Met | Leu | Leu | Met | Lys | Val | Asn | Lys | Asn | Asp | Ile | Arg | Lys | Lys | Val | |
| | 145 | | | | | 150 | | | | | 155 | | | | | |
| AGG | CGC | CTA | ATG | GGA | AAG | TCG | CAC | ATT | GGG | CTT | GTG | TAC | AGC | CAG | CAA | 526 |
| Arg | Arg | Leu | Met | Gly | Lys | Ser | His | Ile | Gly | Leu | Val | Tyr | Ser | Gln | Gln | |
| 160 | | | | | 165 | | | | | 170 | | | | | 175 | |
| ATC | AAT | GAG | GTG | CTT | GAT | CAG | CTG | GCG | AAC | CTG | AAT | GGA | CGC | GAT | CTC | 574 |
| Ile | Asn | Glu | Val | Leu | Asp | Gln | Leu | Ala | Asn | Leu | Asn | Gly | Arg | Asp | Leu | |
| | | | | 180 | | | | | 185 | | | | | 190 | | |
| TCT | ATC | TGG | TCC | AGT | GGC | AGC | CGG | CAC | ATG | AAG | AAG | CAG | ACA | TTT | GTG | 622 |
| Ser | Ile | Trp | Ser | Ser | Gly | Ser | Arg | His | Met | Lys | Lys | Gln | Thr | Phe | Val | |
| | | | 195 | | | | | 200 | | | | | 205 | | | |
| GTA | CAT | GCA | GGG | ACA | GAT | ACA | AAC | GGA | GAT | ATC | TTT | TTC | ATG | GAG | GTG | 670 |
| Val | His | Ala | Gly | Thr | Asp | Thr | Asn | Gly | Asp | Ile | Phe | Phe | Met | Glu | Val | |
| | | 210 | | | | | 215 | | | | | 220 | | | | |
| TGC | GAT | GAC | TGT | GTG | GTG | TTG | CGT | AGT | AAC | ATC | GGA | ACA | GTG | TAT | GAG | 718 |
| Cys | Asp | Asp | Cys | Val | Val | Leu | Arg | Ser | Asn | Ile | Gly | Thr | Val | Tyr | Glu | |
| | 225 | | | | | 230 | | | | | 235 | | | | | |
| CGC | TGG | TGG | TAC | GAG | AAG | CTC | ATC | AAC | ATG | ACC | TAC | TGT | CCC | AAG | ACG | 766 |
| Arg | Trp | Trp | Tyr | Glu | Lys | Leu | Ile | Asn | Met | Thr | Tyr | Cys | Pro | Lys | Thr | |
| 240 | | | | | 245 | | | | | 250 | | | | | 255 | |
| AAG | GTG | TTG | TGC | TTG | TGG | CGT | AGA | AAT | GGC | TCT | GAG | ACC | CAG | CTC | AAC | 814 |
| Lys | Val | Leu | Cys | Leu | Trp | Arg | Arg | Asn | Gly | Ser | Glu | Thr | Gln | Leu | Asn | |
| | | | | 260 | | | | | 265 | | | | | 270 | | |
| AAG | TTC | TAT | ACT | AAA | AAG | TGT | CGG | GAG | CTG | TAC | TAC | TGT | GTG | AAG | GAC | 862 |
| Lys | Phe | Tyr | Thr | Lys | Lys | Cys | Arg | Glu | Leu | Tyr | Tyr | Cys | Val | Lys | Asp | |
| | | | 275 | | | | | 280 | | | | | 285 | | | |
| AGC | ATG | GAG | CGC | GCT | GCC | GCC | CGA | CAG | CAA | AGC | ATC | AAA | CCC | GGA | CCT | 910 |
| Ser | Met | Glu | Arg | Ala | Ala | Ala | Arg | Gln | Gln | Ser | Ile | Lys | Pro | Gly | Pro | |
| | | 290 | | | | | 295 | | | | | 300 | | | | |
| GAA | TTG | GGT | GGC | GAG | TTC | CCT | GTG | CAG | GAC | CTG | AAG | ACT | GGT | GAG | GGT | 958 |
| Glu | Leu | Gly | Gly | Glu | Phe | Pro | Val | Gln | Asp | Leu | Lys | Thr | Gly | Glu | Gly | |
| | 305 | | | | | 310 | | | | | 315 | | | | | |
| GGC | CTG | CTG | CAG | GTG | ACC | CTG | GAA | GGG | ATC | AAC | CTC | AAA | TTC | ATG | CAC | 1006 |
| Gly | Leu | Leu | Gln | Val | Thr | Leu | Glu | Gly | Ile | Asn | Leu | Lys | Phe | Met | His | |
| 320 | | | | | 325 | | | | | 330 | | | | | 335 | |
| AAT | CAG | GTT | TTC | ATA | GAG | CTG | AAT | CAC | ATT | AAA | AAG | TGC | AAT | ACA | GTT | 1054 |
| Asn | Gln | Val | Phe | Ile | Glu | Leu | Asn | His | Ile | Lys | Lys | Cys | Asn | Thr | Val | |
| | | | | 340 | | | | | 345 | | | | | 350 | | |
| CGA | GGC | GTC | TTT | GTC | CTG | GAG | GAA | TTT | GTT | CCT | GAA | ATT | AAA | GAA | GTG | 1102 |
| Arg | Gly | Val | Phe | Val | Leu | Glu | Glu | Phe | Val | Pro | Glu | Ile | Lys | Glu | Val | |
| | | | 355 | | | | | 360 | | | | | 365 | | | |

| | | | | | | | | | | | | | | | |
|---|---|---|---|---|---|---|---|---|---|---|---|---|---|---|---|
| GTG | AGC | CAC | AAG | TAC | AAG | ACA | CCA | ATG | GCC | CAC | GAA | ATC | TGC | TAC | TCC | 1150
| Val | Ser | His | Lys | Tyr | Lys | Thr | Pro | Met | Ala | His | Glu | Ile | Cys | Tyr | Ser |
| | | 370 | | | | 375 | | | | | 380 | | | | |
| GTA | TTA | TGT | CTC | TTC | TCG | TAC | GTG | GCT | GCA | GTT | CAT | AGC | AGT | GAG | GAA | 1198
| Val | Leu | Cys | Leu | Phe | Ser | Tyr | Val | Ala | Ala | Val | His | Ser | Ser | Glu | Glu |
| | 385 | | | | | 390 | | | | | 395 | | | | |
| GAT | CTC | AGA | ACC | CCG | CCC | CGG | CCT | GTC | TCT | AGC | TGATGGAGAG | GGGCTACGCA | | | | 1251
| Asp | Leu | Arg | Thr | Pro | Pro | Arg | Pro | Val | Ser | Ser | | | | | |
| 400 | | | | | 405 | | | | | 410 | | | | | |

| | | | | |
|---|---|---|---|---|
| GCTGCCCCAG | CCCAGGGCAC | GCCCCTGGCC | CCTTGCTGTT | CCCAAGTGCA CGATGCTGCT | 1311
| GTGACTGAGG | AGTGGATGAT | GCTCGTGTGT | CCTCTGCAAG | CCCCCTGCTG TGGCTTGGGT | 1371
| GGGTACCGGT | TATGTGTCCC | TCTGAGTGTG | TCTTGAGCGT | GTCCACCTTC TCCCTCTCCA | 1431
| CTCCCAGAAG | ACCAAACTGC | CTTCCCCTCA | GGGCTCAAGA | ATGTGTACAG TCTGTGGGGC | 1491
| CGGTGTGAAC | CCACTATTTT | GTGTCCTTGA | GACATTTGTG | TTGTGGTTCC TTGTCCTTGT | 1551
| CCCTGGCGTT | AACTGTCCAC | TGCAAGAGTC | TGGCTCTCCC | TTCTCTGTGA CCCGGCATGA | 1611
| CTGGGCGCCT | GGAGCAGTTT | CACTCTGTGA | GGAGTGAGGG | AACCCTGGGG CTCACCCTCT | 1671
| CAGAGGAAGG | GCACAGAGAG | GAAGGGAAGA | ATTGGGGGGC | AGCCGGAGTG AGTGGCAGCC | 1731
| TCCCTGCTTC | CTTCTGCATT | CCCAAGCCGG | CAGCTACTGC | CCAGGGCCCG CAGTGTTGGC | 1791
| TGCTGCCTGC | CACAGCCTCT | GTGACTGCAG | TGGAGCGGCG | AATTCCCTGT GGCCTGCCAC | 1851
| GCCTTCGGCA | TCAGAGGATG | GAGTGGTCGA | GGCTAGTGGA | GTCCCAGGGA CCGCTGGCTG | 1911
| CTCTGCCTGA | GCATCAGGGA | GGGGGCAGGA | AAGACCAAGC | TGGGTTTGCA CATCTGTCTG | 1971
| CAGGCTGTCT | CTCCAGGCAC | GGGGTGTCAG | GAGGGAGAGA | CAGCCTGGGT ATGGGCAAGA | 2031
| AATGACTGTA | AATATTTCAG | CCCCACATTA | TTTATAGAAA | ATGTACAGTT GTGTGAATGT | 2091
| GAAATAAATG | TCCTCACCTC | CCAAAAAAAA | AAAAAAAAAA | AAAAAAAAAA AAAAAAAAA | 2151
| AAAAAA | | | | | 2158

( 2 ) INFORMATION FOR SEQ ID NO:2:

( i ) SEQUENCE CHARACTERISTICS:
        ( A ) LENGTH: 410 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | |
|---|---|---|---|---|---|---|---|---|---|---|---|---|---|---|
| Ser | Asn | Ala | Gly | Asp | Gly | Pro | Gly | Gly | Glu | Gly | Ser | Val | His | Leu | Ala |
| 1 | | | | 5 | | | | | 10 | | | | | 15 |
| Ser | Ser | Arg | Gly | Thr | Leu | Ser | Asp | Ser | Glu | Ile | Glu | Thr | Asn | Ser | Ala |
| | | | 20 | | | | | 25 | | | | | 30 | |
| Thr | Ser | Thr | Ile | Phe | Gly | Lys | Ala | His | Ser | Leu | Lys | Pro | Ser | Ile | Lys |
| | | | 35 | | | | 40 | | | | | 45 | | |
| Glu | Lys | Leu | Ala | Gly | Ser | Pro | Ile | Arg | Thr | Ser | Glu | Asp | Val | Ser | Gln |
| | 50 | | | | | 55 | | | | | 60 | | | |
| Arg | Val | Tyr | Leu | Tyr | Glu | Gly | Leu | Leu | Gly | Lys | Glu | Arg | Ser | Thr | Leu |
| 65 | | | | | 70 | | | | | 75 | | | | | 80 |
| Trp | Asp | Gln | Met | Gln | Phe | Trp | Glu | Asp | Ala | Phe | Leu | Asp | Ala | Val | Met |
| | | | | 85 | | | | | 90 | | | | | 95 | |
| Leu | Glu | Arg | Glu | Gly | Met | Gly | Met | Asp | Gln | Gly | Pro | Gln | Glu | Met | Ile |
| | | | | 100 | | | | 105 | | | | | 110 | | |
| Asp | Arg | Tyr | Leu | Ser | Leu | Gly | Glu | His | Asp | Arg | Lys | Arg | Leu | Glu | Asp |
| | | | 115 | | | | | 120 | | | | | 125 | | |

| | | | | | | | | | | | | | | |
|---|---|---|---|---|---|---|---|---|---|---|---|---|---|---|
| Asp | Glu | Asp | Arg | Leu | Leu | Ala | Thr | Leu | Leu | His | Asn | Leu | Ile | Ser | Tyr |
| | 130 | | | | 135 | | | | | 140 | | | | | |
| Met | Leu | Leu | Met | Lys | Val | Asn | Lys | Asn | Asp | Ile | Arg | Lys | Lys | Val | Arg |
| 145 | | | | | 150 | | | | | 155 | | | | | 160 |
| Arg | Leu | Met | Gly | Lys | Ser | His | Ile | Gly | Leu | Val | Tyr | Ser | Gln | Gln | Ile |
| | | | | 165 | | | | | 170 | | | | | 175 | |
| Asn | Glu | Val | Leu | Asp | Gln | Leu | Ala | Asn | Leu | Asn | Gly | Arg | Asp | Leu | Ser |
| | | | 180 | | | | 185 | | | | | 190 | | | |
| Ile | Trp | Ser | Ser | Gly | Ser | Arg | His | Met | Lys | Lys | Gln | Thr | Phe | Val | Val |
| | | 195 | | | | | 200 | | | | | 205 | | | |
| His | Ala | Gly | Thr | Asp | Thr | Asn | Gly | Asp | Ile | Phe | Phe | Met | Glu | Val | Cys |
| | 210 | | | | | 215 | | | | | 220 | | | | |
| Asp | Asp | Cys | Val | Val | Leu | Arg | Ser | Asn | Ile | Gly | Thr | Val | Tyr | Glu | Arg |
| 225 | | | | | 230 | | | | | 235 | | | | | 240 |
| Trp | Trp | Tyr | Glu | Lys | Leu | Ile | Asn | Met | Thr | Tyr | Cys | Pro | Lys | Thr | Lys |
| | | | | 245 | | | | | 250 | | | | | 255 | |
| Val | Leu | Cys | Leu | Trp | Arg | Arg | Asn | Gly | Ser | Glu | Thr | Gln | Leu | Asn | Lys |
| | | | 260 | | | | | 265 | | | | | 270 | | |
| Phe | Tyr | Thr | Lys | Lys | Cys | Arg | Glu | Leu | Tyr | Tyr | Cys | Val | Lys | Asp | Ser |
| | | 275 | | | | | 280 | | | | | 285 | | | |
| Met | Glu | Arg | Ala | Ala | Ala | Arg | Gln | Gln | Ser | Ile | Lys | Pro | Gly | Pro | Glu |
| | 290 | | | | | 295 | | | | | 300 | | | | |
| Leu | Gly | Gly | Glu | Phe | Pro | Val | Gln | Asp | Leu | Lys | Thr | Gly | Glu | Gly | Gly |
| 305 | | | | | 310 | | | | | 315 | | | | | 320 |
| Leu | Leu | Gln | Val | Thr | Leu | Glu | Gly | Ile | Asn | Leu | Lys | Phe | Met | His | Asn |
| | | | | 325 | | | | | 330 | | | | | 335 | |
| Gln | Val | Phe | Ile | Glu | Leu | Asn | His | Ile | Lys | Lys | Cys | Asn | Thr | Val | Arg |
| | | | 340 | | | | | 345 | | | | | 350 | | |
| Gly | Val | Phe | Val | Leu | Glu | Glu | Phe | Val | Pro | Glu | Ile | Lys | Glu | Val | Val |
| | | 355 | | | | | 360 | | | | | 365 | | | |
| Ser | His | Lys | Tyr | Lys | Thr | Pro | Met | Ala | His | Glu | Ile | Cys | Tyr | Ser | Val |
| | 370 | | | | | 375 | | | | | 380 | | | | |
| Leu | Cys | Leu | Phe | Ser | Tyr | Val | Ala | Ala | Val | His | Ser | Ser | Glu | Glu | Asp |
| 385 | | | | | 390 | | | | | 395 | | | | | 400 |
| Leu | Arg | Thr | Pro | Pro | Arg | Pro | Val | Ser | Ser | | | | | | |
| | | | | 405 | | | | | 410 | | | | | | |

( 2 ) INFORMATION FOR SEQ ID NO:3:

( i ) SEQUENCE CHARACTERISTICS:
        ( A ) LENGTH: 826 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 2..415

( x i ) SEQUENCE DESCRIPTION: SEQ ID NO:3:

```
G  GAG  GTG  CAG  GAC  CTC  TTC  GAA  GCC  CAG  GGC  AAT  GAC  CGA  CTG  AAG          46
   Glu  Val  Gln  Asp  Leu  Phe  Glu  Ala  Gln  Gly  Asn  Asp  Arg  Leu  Lys
    1              5                     10                    15

CTG  CTG  GTG  CTG  TAC  AGT  GGA  GAG  GAT  GAT  GAG  CTG  CTA  CAG  CGG  GCA          94
Leu  Leu  Val  Leu  Tyr  Ser  Gly  Glu  Asp  Asp  Glu  Leu  Leu  Gln  Arg  Ala
            20                     25                    30
```

```
GCT GCC GGG GGC TTG GCC ATG CTT ACC TCC ATG CGG CCC ACG CTC TGC      142
Ala Ala Gly Gly Leu Ala Met Leu Thr Ser Met Arg Pro Thr Leu Cys
            35                      40                  45

AGC CGC ATT CCC CAA GTG ACC ACA CAC TGG CTG GAG ATC CTG CAG GCC      190
Ser Arg Ile Pro Gln Val Thr Thr His Trp Leu Glu Ile Leu Gln Ala
        50                      55                  60

CTG CTT CTG AGC TCC AAC CAG GAG CTG CAG CAC CGG GGT GCT GTG GTG      238
Leu Leu Leu Ser Ser Asn Gln Glu Leu Gln His Arg Gly Ala Val Val
    65                      70                  75

GTG CTG AAC ATG GTG GAG GCC TCG AGG GAG ATT GCC AGC ACC CTG ATG      286
Val Leu Asn Met Val Glu Ala Ser Arg Glu Ile Ala Ser Thr Leu Met
80                      85                  90                  95

GAG AGT GAG ATG ATG GAG ATC TTG TCA GTG CTA GCT AAG GGT GAC CAC      334
Glu Ser Glu Met Met Glu Ile Leu Ser Val Leu Ala Lys Gly Asp His
                    100                 105                 110

AGC CCT GTC ACA AGG GCT GCT GCA GCC TGC CTG GAC AAA GCA GTG GAA      382
Ser Pro Val Thr Arg Ala Ala Ala Ala Cys Leu Asp Lys Ala Val Glu
                115                 120                 125

TAT GGG CTT ATC CAA CCC AAC CAA GAT GGA GAG TGAGGGGGTT GTCCCTGGGC    435
Tyr Gly Leu Ile Gln Pro Asn Gln Asp Gly Glu
            130                 135

CCAAGGCTCA TGCACACGCT ACCTATTGTG GCACGGAGAG TAAGGACGGA AGCAGCTTTG    495

GCTGGTGGTG GCTGGCATGC CCAATACTCT TGCCCATCCT CGCTTGCTGC CCTAGGATGT    555

CCTCTGTTCT GAGTCAGCGG CCACGTTCAG TCACACAGCC CTGCTTGGCC AGCACTGCCT    615

GCAGCCTCAC TCAGAGGGGC CCTTTTTCTG TACTACTGTA GTCAGCTGGG AATGGGGAAG    675

GTGCATCCCA ACACAGCCTG TGGATCCTGG GGCATTTGGA AGGGCGCACA CATCAGCAGC    735

CTCACCAGCT GTGAGCCTGC TATCAGGCCT GCCCCTCCAA TAAAAGTGTG TAGAACTCCA    795

AAAAAAAAAA AAAAAAAAAA AAAAAAAAA A                                    826
```

( 2 ) INFORMATION FOR SEQ ID NO:4:

( i ) SEQUENCE CHARACTERISTICS:
    ( A ) LENGTH: 138 amino acids
    ( B ) TYPE: amino acid
    ( D ) TOPOLOGY: linear ( i i ) MOLECULE TYPE: protein ( x i ) SEQUENCE DESCRIPTION: SEQ ID NO:4:

```
Glu Val Gln Asp Leu Phe Glu Ala Gln Gly Asn Asp Arg Leu Lys Leu
 1               5                  10                  15

Leu Val Leu Tyr Ser Gly Glu Asp Glu Leu Leu Gln Arg Ala Ala
            20                  25                  30

Ala Gly Gly Leu Ala Met Leu Thr Ser Met Arg Pro Thr Leu Cys Ser
            35                  40                  45

Arg Ile Pro Gln Val Thr Thr His Trp Leu Glu Ile Leu Gln Ala Leu
        50                  55                  60

Leu Leu Ser Ser Asn Gln Glu Leu Gln His Arg Gly Ala Val Val Val
65                  70                  75                  80

Leu Asn Met Val Glu Ala Ser Arg Glu Ile Ala Ser Thr Leu Met Glu
                85                  90                  95

Ser Glu Met Met Glu Ile Leu Ser Val Leu Ala Lys Gly Asp His Ser
                100                 105                 110

Pro Val Thr Arg Ala Ala Ala Ala Cys Leu Asp Lys Ala Val Glu Tyr
            115                 120                 125
```

```
Gly  Leu  Ile  Gln  Pro  Asn  Gln  Asp  Gly  Glu
    130                      135
```

( 2 ) INFORMATION FOR SEQ ID NO:5:

( i ) SEQUENCE CHARACTERISTICS:
        ( A ) LENGTH: 722 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 2..559

( x i ) SEQUENCE DESCRIPTION: SEQ ID NO:5:

```
G  GAG  AAG  CCG  CTG  CAC  GCC  CTG  CTG  CAC  GGC  CGC  GGG  GTT  TGC  CTC            46
   Glu  Lys  Pro  Leu  His  Ala  Leu  Leu  His  Gly  Arg  Gly  Val  Cys  Leu
    1              5                       10                      15

AAC  GAA  AAG  AGC  TAC  CGC  GAG  CAA  GTC  AAG  ATC  GAG  AGA  GAC  TCC  CGT          94
Asn  Glu  Lys  Ser  Tyr  Arg  Glu  Gln  Val  Lys  Ile  Glu  Arg  Asp  Ser  Arg
               20                       25                       30

GAG  CAC  GAG  GAG  CCC  ACC  ACC  TCT  GAG  ATG  GCC  GAG  GAG  ACC  TAC  TCC         142
Glu  His  Glu  Glu  Pro  Thr  Thr  Ser  Glu  Met  Ala  Glu  Glu  Thr  Tyr  Ser
          35                       40                       45

CCC  AAG  ATC  TTC  CGG  CCC  AAA  CAC  ACC  CGC  ATC  TCC  GAG  CTG  AAG  GCT         190
Pro  Lys  Ile  Phe  Arg  Pro  Lys  His  Thr  Arg  Ile  Ser  Glu  Leu  Lys  Ala
               50                       55                       60

GAA  GCA  GTG  AAG  AAG  GAC  CGC  AGA  AAG  AAG  CTG  ACC  CAG  TCC  AAG  TTT         238
Glu  Ala  Val  Lys  Lys  Asp  Arg  Arg  Lys  Lys  Leu  Thr  Gln  Ser  Lys  Phe
          65                       70                       75

GTC  GGG  GGA  GCC  GAG  AAC  ACT  GCC  CAC  CCC  CGG  ATC  ATC  TCT  GAA  CCT         286
Val  Gly  Gly  Ala  Glu  Asn  Thr  Ala  His  Pro  Arg  Ile  Ile  Ser  Glu  Pro
 80                        85                       90                       95

GAG  ATG  AGA  CAG  GAG  TCT  GAG  CAG  GGC  CCC  TGC  CGC  AGA  CAC  ATG  GAG         334
Glu  Met  Arg  Gln  Glu  Ser  Glu  Gln  Gly  Pro  Cys  Arg  Arg  His  Met  Glu
               100                      105                      110

GCT  TCC  CTG  CAG  GAG  CTC  AAA  GCC  AGC  CCA  CGC  ATG  GTG  CCC  CGT  GCT         382
Ala  Ser  Leu  Gln  Glu  Leu  Lys  Ala  Ser  Pro  Arg  Met  Val  Pro  Arg  Ala
          115                      120                      125

GTG  TAC  CTG  CCC  AAT  TGT  GAC  CGC  AAA  GGA  TTC  TAC  AAG  AGA  AAG  CAG         430
Val  Tyr  Leu  Pro  Asn  Cys  Asp  Arg  Lys  Gly  Phe  Tyr  Lys  Arg  Lys  Gln
               130                      135                      140

TGC  AAA  CCT  TCC  CGT  GGC  CGC  AAG  CGT  GGC  ATC  TGC  TGG  TGC  GTG  GAC         478
Cys  Lys  Pro  Ser  Arg  Gly  Arg  Lys  Arg  Gly  Ile  Cys  Trp  Cys  Val  Asp
 145                      150                      155

AAG  TAC  GGG  ATG  AAG  CTG  CCA  GGC  ATG  GAG  TAC  GTT  GAC  GGG  GAC  TTT         526
Lys  Tyr  Gly  Met  Lys  Leu  Pro  Gly  Met  Glu  Tyr  Val  Asp  Gly  Asp  Phe
 160                      165                      170                      175

CAG  TGC  CAC  ACC  TTC  GAC  AGC  AGC  AAC  GTT  GAG  TGATGCGTCC  CCCCCCAACC          579
Gln  Cys  His  Thr  Phe  Asp  Ser  Ser  Asn  Val  Glu
                180                      185

TTTCCCTCAC  CCCCTTCCAC  CCCCAGCCCC  GACTCCAGCC  AGCGCCTCCC  TCCACCCCAG                639

GACGCCACTC  ATTTCATCTC  ATTTAAGGGA  AAAATATATA  TCTATCTATT  TGAGGAAAAA                699

AAAAAAAAAA  AAAAAAAAAA  AAA                                                           722
```

( 2 ) INFORMATION FOR SEQ ID NO:6:

( i ) SEQUENCE CHARACTERISTICS:

(A) LENGTH: 186 amino acids
(B) TYPE: amino acid
(D) TOPOLOGY: linear (ii) MOLECULE TYPE: protein (xi) SEQUENCE DESCRIPTION: SEQ ID NO:6:

| Glu | Lys | Pro | Leu | His | Ala | Leu | Leu | His | Gly | Arg | Gly | Val | Cys | Leu | Asn |
|---|---|---|---|---|---|---|---|---|---|---|---|---|---|---|---|
| 1 | | | | 5 | | | | | 10 | | | | | 15 | |
| Glu | Lys | Ser | Tyr | Arg | Glu | Gln | Val | Lys | Ile | Glu | Arg | Asp | Ser | Arg | Glu |
| | | | 20 | | | | | 25 | | | | | 30 | | |
| His | Glu | Glu | Pro | Thr | Thr | Ser | Glu | Met | Ala | Glu | Glu | Thr | Tyr | Ser | Pro |
| | | 35 | | | | | 40 | | | | | 45 | | | |
| Lys | Ile | Phe | Arg | Pro | Lys | His | Thr | Arg | Ile | Ser | Glu | Leu | Lys | Ala | Glu |
| | 50 | | | | | 55 | | | | | 60 | | | | |
| Ala | Val | Lys | Lys | Asp | Arg | Arg | Lys | Lys | Leu | Thr | Gln | Ser | Lys | Phe | Val |
| 65 | | | | | 70 | | | | | 75 | | | | | 80 |
| Gly | Gly | Ala | Glu | Asn | Thr | Ala | His | Pro | Arg | Ile | Ile | Ser | Glu | Pro | Glu |
| | | | | 85 | | | | | 90 | | | | | 95 | |
| Met | Arg | Gln | Glu | Ser | Glu | Gln | Gly | Pro | Cys | Arg | Arg | His | Met | Glu | Ala |
| | | | 100 | | | | | 105 | | | | | 110 | | |
| Ser | Leu | Gln | Glu | Leu | Lys | Ala | Ser | Pro | Arg | Met | Val | Pro | Arg | Ala | Val |
| | | 115 | | | | | 120 | | | | | 125 | | | |
| Tyr | Leu | Pro | Asn | Cys | Asp | Arg | Lys | Gly | Phe | Tyr | Lys | Arg | Lys | Gln | Cys |
| | 130 | | | | | 135 | | | | | 140 | | | | |
| Lys | Pro | Ser | Arg | Gly | Arg | Lys | Arg | Gly | Ile | Cys | Trp | Cys | Val | Asp | Lys |
| 145 | | | | | 150 | | | | | 155 | | | | | 160 |
| Tyr | Gly | Met | Lys | Leu | Pro | Gly | Met | Glu | Tyr | Val | Asp | Gly | Asp | Phe | Gln |
| | | | | 165 | | | | | 170 | | | | | 175 | |
| Cys | His | Thr | Phe | Asp | Ser | Ser | Asn | Val | Glu | | | | | | |
| | | | 180 | | | | | 185 | | | | | | | |

(2) INFORMATION FOR SEQ ID NO:7:

(i) SEQUENCE CHARACTERISTICS:
(A) LENGTH: 1023 base pairs
(B) TYPE: nucleic acid
(C) STRANDEDNESS: double
(D) TOPOLOGY: linear (ii) MOLECULE TYPE: cDNA (iii) HYPOTHETICAL: NO (ix) FEATURE:
(A) NAME/KEY: CDS
(B) LOCATION: 57..875

(xi) SEQUENCE DESCRIPTION: SEQ ID NO:7:

| CCCTGCACTC | TCGCTCTCCT | GCCCCACCCC | GAGGTAAAGG | GGGCGACTAA | GAGAAG | | | | | | | | | | | 56 |
|---|---|---|---|---|---|---|---|---|---|---|---|---|---|---|---|---|
| ATG | GTG | TTG | CTC | ACC | GCG | GTC | CTC | CTG | CTG | CTG | GCC | GCC | TAT | GCG | GGG | 104 |
| Met | Val | Leu | Leu | Thr | Ala | Val | Leu | Leu | Leu | Leu | Ala | Ala | Tyr | Ala | Gly | |
| 1 | | | | 5 | | | | | 10 | | | | | 15 | | |
| CCG | GCC | CAG | AGC | CTG | GGC | TCC | TTC | GTG | CAC | TGC | GAG | CCC | TGC | GAC | GAG | 152 |
| Pro | Ala | Gln | Ser | Leu | Gly | Ser | Phe | Val | His | Cys | Glu | Pro | Cys | Asp | Glu | |
| | | | 20 | | | | | 25 | | | | | 30 | | | |
| AAA | GCC | CTC | TCC | ATG | TGC | CCC | CCC | AGC | CCC | CTG | GGC | TGC | GAG | CTG | GTC | 200 |
| Lys | Ala | Leu | Ser | Met | Cys | Pro | Pro | Ser | Pro | Leu | Gly | Cys | Glu | Leu | Val | |
| | | | 35 | | | | | 40 | | | | | 45 | | | |
| AAG | GAG | CCG | GGC | TGC | GGC | TGC | TGC | ATG | ACC | TGC | GCC | CTG | GCC | GAG | GGG | 248 |
| Lys | Glu | Pro | Gly | Cys | Gly | Cys | Cys | Met | Thr | Cys | Ala | Leu | Ala | Glu | Gly | |
| | | | 50 | | | | | 55 | | | | | 60 | | | |

-continued

| | | | | | | | | | | | | | | | | |
|---|---|---|---|---|---|---|---|---|---|---|---|---|---|---|---|---|
| CAG | TCG | TGC | GGC | GTC | TAC | ACC | GAG | CGC | TGC | GCC | CAG | GGG | CTG | CGC | TGC | 296 |
| Gln | Ser | Cys | Gly | Val | Tyr | Thr | Glu | Arg | Cys | Ala | Gln | Gly | Leu | Arg | Cys | |
| 65 | | | | 70 | | | | 75 | | | | | | | 80 | |
| CTC | CCC | CGG | CAG | GAC | GAG | GAG | AAG | CCG | CTG | CAC | GCC | CTG | CTG | CAC | GGC | 344 |
| Leu | Pro | Arg | Gln | Asp | Glu | Glu | Lys | Pro | Leu | His | Ala | Leu | Leu | His | Gly | |
| | | | | 85 | | | | | 90 | | | | | 95 | | |
| CGC | GGG | GTT | TGC | CTC | AAC | GAA | AAG | AGC | TAC | CGC | GAG | CAA | GTC | AAG | ATC | 392 |
| Arg | Gly | Val | Cys | Leu | Asn | Glu | Lys | Ser | Tyr | Arg | Glu | Gln | Val | Lys | Ile | |
| | | | 100 | | | | | 105 | | | | | 110 | | | |
| GAG | AGA | GAC | TCC | CGT | GAG | CAC | GAG | GAG | CCC | ACC | ACC | TCT | GAG | ATG | GCC | 440 |
| Glu | Arg | Asp | Ser | Arg | Glu | His | Glu | Glu | Pro | Thr | Thr | Ser | Glu | Met | Ala | |
| | | | 115 | | | | 120 | | | | | 125 | | | | |
| GAG | GAG | ACC | TAC | TCC | CCC | AAG | ATC | TTC | CGG | CCC | AAA | CAC | ACC | CGC | ATC | 488 |
| Glu | Glu | Thr | Tyr | Ser | Pro | Lys | Ile | Phe | Arg | Pro | Lys | His | Thr | Arg | Ile | |
| | | 130 | | | | | 135 | | | | | 140 | | | | |
| TCC | GAG | CTG | AAG | GCT | GAA | GCA | GTG | AAG | AAG | GAC | CGC | AGA | AAG | AAG | CTG | 536 |
| Ser | Glu | Leu | Lys | Ala | Glu | Ala | Val | Lys | Lys | Asp | Arg | Arg | Lys | Lys | Leu | |
| 145 | | | | | 150 | | | | | 155 | | | | | 160 | |
| ACC | CAG | TCC | AAG | TTT | GTC | GGG | GGA | GCC | GAG | AAC | ACT | GCC | CAC | CCC | CGG | 584 |
| Thr | Gln | Ser | Lys | Phe | Val | Gly | Gly | Ala | Glu | Asn | Thr | Ala | His | Pro | Arg | |
| | | | | 165 | | | | | 170 | | | | | 175 | | |
| ATC | ATC | TCT | GCA | CCT | GAG | ATG | AGA | CAG | GAG | TCT | GAG | CAG | GGC | CCC | TGC | 632 |
| Ile | Ile | Ser | Ala | Pro | Glu | Met | Arg | Gln | Glu | Ser | Glu | Gln | Gly | Pro | Cys | |
| | | | 180 | | | | | 185 | | | | | 190 | | | |
| CGC | AGA | CAC | ATG | GAG | GCT | TCC | CTG | CAG | GAG | CTC | AAA | GCC | AGC | CCA | CGC | 680 |
| Arg | Arg | His | Met | Glu | Ala | Ser | Leu | Gln | Glu | Leu | Lys | Ala | Ser | Pro | Arg | |
| | | 195 | | | | | 200 | | | | | 205 | | | | |
| ATG | GTG | CCC | CGT | GCT | GTG | TAC | CTG | CCC | AAT | TGT | GAC | CGC | AAA | GGA | TTC | 728 |
| Met | Val | Pro | Arg | Ala | Val | Tyr | Leu | Pro | Asn | Cys | Asp | Arg | Lys | Gly | Phe | |
| | 210 | | | | | 215 | | | | | 220 | | | | | |
| TAC | AAG | AGA | AAG | CAG | TGC | AAA | CCT | TCC | CGT | GGC | CGC | AAG | CGT | GGC | ATC | 776 |
| Tyr | Lys | Arg | Lys | Gln | Cys | Lys | Pro | Ser | Arg | Gly | Arg | Lys | Arg | Gly | Ile | |
| 225 | | | | | 230 | | | | | 235 | | | | | 240 | |
| TGC | TGG | TGC | GTG | GAC | AAG | TAC | GGG | ATG | AAG | CTG | CCA | GGC | ATG | GAG | TAC | 824 |
| Cys | Trp | Cys | Val | Asp | Lys | Tyr | Gly | Met | Lys | Leu | Pro | Gly | Met | Glu | Tyr | |
| | | | | 245 | | | | | 250 | | | | | 255 | | |
| GTT | GAC | GGG | GAC | TTT | CAG | TGC | CAC | ACC | TTC | GAC | AGC | AGC | AAC | GTT | GAG | 872 |
| Val | Asp | Gly | Asp | Phe | Gln | Cys | His | Thr | Phe | Asp | Ser | Ser | Asn | Val | Glu | |
| | | | 260 | | | | | 265 | | | | | 270 | | | |

| | | | | |
|---|---|---|---|---|
| TGATGCGTCC | CCCCCAACC | TTTCCCTCAC | CCCTCCCAC | CCCCAGCCCC GACTCCAGCC | 932 |
| AGCGCCTCCC | TCCACCCCAG | GACGCCACTC | ATTTCATCTC | ATTTAAGGGA AAAATATATA | 992 |
| TCTATCTATT | TGAAAAAAAA | AAAAAAAACC | C | | 1023 |

( 2 ) INFORMATION FOR SEQ ID NO:8:

( i ) SEQUENCE CHARACTERISTICS:
        ( A ) LENGTH: 272 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

| | | | | | | | | | | | | | | |
|---|---|---|---|---|---|---|---|---|---|---|---|---|---|---|
| Met | Val | Leu | Leu | Thr | Ala | Val | Leu | Leu | Leu | Ala | Ala | Tyr | Ala | Gly |
| 1 | | | | 5 | | | | | 10 | | | | | 15 |
| Pro | Ala | Gln | Ser | Leu | Gly | Ser | Phe | Val | His | Cys | Glu | Pro | Cys | Asp | Glu |
| | | | 20 | | | | 25 | | | | 30 | | | | |
| Lys | Ala | Leu | Ser | Met | Cys | Pro | Pro | Ser | Pro | Leu | Gly | Cys | Glu | Leu | Val |
| | | 35 | | | | | 40 | | | | | 45 | | | |

| Lys | Glu | Pro | Gly | Cys | Gly | Cys | Cys | Met | Thr | Cys | Ala | Leu | Ala | Glu | Gly |
| | 50 | | | | 55 | | | | | 60 | | | | | |

| Gln | Ser | Cys | Gly | Val | Tyr | Thr | Glu | Arg | Cys | Ala | Gln | Gly | Leu | Arg | Cys |
| 65 | | | | | 70 | | | | 75 | | | | | | 80 |

| Leu | Pro | Arg | Gln | Asp | Glu | Glu | Lys | Pro | Leu | His | Ala | Leu | Leu | His | Gly |
| | | | | 85 | | | | | 90 | | | | | 95 | |

| Arg | Gly | Val | Cys | Leu | Asn | Glu | Lys | Ser | Tyr | Arg | Glu | Gln | Val | Lys | Ile |
| | | | 100 | | | | | 105 | | | | | 110 | | |

| Glu | Arg | Asp | Ser | Arg | Glu | His | Glu | Glu | Pro | Thr | Thr | Ser | Glu | Met | Ala |
| | | | 115 | | | | 120 | | | | | 125 | | | |

| Glu | Glu | Thr | Tyr | Ser | Pro | Lys | Ile | Phe | Arg | Pro | Lys | His | Thr | Arg | Ile |
| | | 130 | | | | | 135 | | | | | 140 | | | |

| Ser | Glu | Leu | Lys | Ala | Glu | Ala | Val | Lys | Lys | Asp | Arg | Arg | Lys | Lys | Leu |
| 145 | | | | | 150 | | | | | 155 | | | | | 160 |

| Thr | Gln | Ser | Lys | Phe | Val | Gly | Gly | Ala | Glu | Asn | Thr | Ala | His | Pro | Arg |
| | | | | 165 | | | | | 170 | | | | | 175 | |

| Ile | Ile | Ser | Ala | Pro | Glu | Met | Arg | Gln | Glu | Ser | Glu | Gln | Gly | Pro | Cys |
| | | | 180 | | | | | 185 | | | | | 190 | | |

| Arg | Arg | His | Met | Glu | Ala | Ser | Leu | Gln | Glu | Leu | Lys | Ala | Ser | Pro | Arg |
| | | 195 | | | | | 200 | | | | | 205 | | | |

| Met | Val | Pro | Arg | Ala | Val | Tyr | Leu | Pro | Asn | Cys | Asp | Arg | Lys | Gly | Phe |
| | 210 | | | | | 215 | | | | | 220 | | | | |

| Tyr | Lys | Arg | Lys | Gln | Cys | Lys | Pro | Ser | Arg | Gly | Arg | Lys | Arg | Gly | Ile |
| 225 | | | | | 230 | | | | | 235 | | | | | 240 |

| Cys | Trp | Cys | Val | Asp | Lys | Tyr | Gly | Met | Lys | Leu | Pro | Gly | Met | Glu | Tyr |
| | | | | 245 | | | | | 250 | | | | | 255 | |

| Val | Asp | Gly | Asp | Phe | Gln | Cys | His | Thr | Phe | Asp | Ser | Ser | Asn | Val | Glu |
| | | | | 260 | | | | | 265 | | | | | 270 | |

(2) INFORMATION FOR SEQ ID NO:9:

(i) SEQUENCE CHARACTERISTICS:
        (A) LENGTH: 1694 base pairs
        (B) TYPE: nucleic acid
        (C) STRANDEDNESS: double
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 2..931

(xi) SEQUENCE DESCRIPTION: SEQ ID NO:9:

| C | TCT | CTC | AAG | GCC | AAC | ATC | CCT | GAG | GTG | GAA | GCT | GTC | CTC | AAC | ACC | 46 |
| | Ser | Leu | Lys | Ala | Asn | Ile | Pro | Glu | Val | Glu | Ala | Val | Leu | Asn | Thr | |
| | 1 | | | | 5 | | | | | 10 | | | | | 15 | |

| GAC | AGG | AGT | TTG | GTG | TGT | GAT | GGG | AAG | AGG | GGC | TTA | TTA | ACT | CGT | CTG | 94 |
| Asp | Arg | Ser | Leu | Val | Cys | Asp | Gly | Lys | Arg | Gly | Leu | Leu | Thr | Arg | Leu | |
| | | | | 20 | | | | | 25 | | | | | 30 | | |

| CTG | CAG | GTC | ATG | AAG | AAG | GAG | CCA | GCA | GAG | TCG | TCT | TTC | AGG | TTT | TGG | 142 |
| Leu | Gln | Val | Met | Lys | Lys | Glu | Pro | Ala | Glu | Ser | Ser | Phe | Arg | Phe | Trp | |
| | | | | 35 | | | | | 40 | | | | | 45 | | |

| CAA | GCT | CGG | GCT | GTG | GAG | AGT | TTC | CTC | CGA | GGG | ACC | ACC | TCC | TAT | GCA | 190 |
| Gln | Ala | Arg | Ala | Val | Glu | Ser | Phe | Leu | Arg | Gly | Thr | Thr | Ser | Tyr | Ala | |
| | | | 50 | | | | | 55 | | | | | 60 | | | |

| GAC | CAG | ATG | TTC | CTG | CTG | AAG | CGA | GGC | CTC | TTG | GAG | CAC | ATC | CTT | TAC | 238 |
| Asp | Gln | Met | Phe | Leu | Leu | Lys | Arg | Gly | Leu | Leu | Glu | His | Ile | Leu | Tyr | |
| | | | 65 | | | | | 70 | | | | | 75 | | | |

| | | | | | | | | | | | | | | | | |
|---|---|---|---|---|---|---|---|---|---|---|---|---|---|---|---|---|
| TGC | ATT | GTG | GAC | AGC | GAG | TGT | AAG | TCA | AGG | GAT | GTG | CTC | CAG | AGT | TAC | 286 |
| Cys | Ile | Val | Asp | Ser | Glu | Cys | Lys | Ser | Arg | Asp | Val | Leu | Gln | Ser | Tyr | |
| 80 | | | | | 85 | | | | | 90 | | | | | 95 | |
| TTT | GAC | CTC | CTG | GGG | GAG | CTG | ATG | AAG | TTC | AAC | GTT | GAT | GCA | TTC | AAG | 334 |
| Phe | Asp | Leu | Leu | Gly | Glu | Leu | Met | Lys | Phe | Asn | Val | Asp | Ala | Phe | Lys | |
| | | | | 100 | | | | | 105 | | | | | 110 | | |
| AGA | TTC | AAT | AAA | TAT | ATC | AAC | ACC | GAT | GCA | AAG | TTC | CAG | GTA | TTC | CTG | 382 |
| Arg | Phe | Asn | Lys | Tyr | Ile | Asn | Thr | Asp | Ala | Lys | Phe | Gln | Val | Phe | Leu | |
| | | | | 115 | | | | | 120 | | | | | 125 | | |
| AAG | CAG | ATC | AAC | AGC | TCC | CTG | GTG | GAC | TCC | AAC | ATG | CTG | GTG | CGC | TGT | 430 |
| Lys | Gln | Ile | Asn | Ser | Ser | Leu | Val | Asp | Ser | Asn | Met | Leu | Val | Arg | Cys | |
| | | | 130 | | | | | 135 | | | | | 140 | | | |
| GTC | ACT | CTG | TCC | CTG | GAC | CGA | TTT | GAA | AAC | CAG | GTG | GAT | ATG | AAA | GTT | 478 |
| Val | Thr | Leu | Ser | Leu | Asp | Arg | Phe | Glu | Asn | Gln | Val | Asp | Met | Lys | Val | |
| | | | 145 | | | | | 150 | | | | | 155 | | | |
| GCC | GAG | GTA | CTG | TCT | GAA | TGC | CGC | CTG | CTC | GCC | TAC | ATA | TCC | CAG | GTG | 526 |
| Ala | Glu | Val | Leu | Ser | Glu | Cys | Arg | Leu | Leu | Ala | Tyr | Ile | Ser | Gln | Val | |
| 160 | | | | | 165 | | | | | 170 | | | | | 175 | |
| CCC | ACG | CAG | ATG | TCC | TTC | CTC | TTC | CGC | CTC | ATC | AAC | ATC | ATC | CAC | GTG | 574 |
| Pro | Thr | Gln | Met | Ser | Phe | Leu | Phe | Arg | Leu | Ile | Asn | Ile | Ile | His | Val | |
| | | | | 180 | | | | | 185 | | | | | 190 | | |
| CAG | ACG | CTG | ACC | CAG | GAG | AAC | GTC | AGC | TGC | CTC | AAC | ACC | AGC | CTG | GTG | 622 |
| Gln | Thr | Leu | Thr | Gln | Glu | Asn | Val | Ser | Cys | Leu | Asn | Thr | Ser | Leu | Val | |
| | | | | 195 | | | | | 200 | | | | | 205 | | |
| ATC | CTG | ATG | CTG | GCC | CGA | CGG | AAA | GAG | CGG | CTG | CCC | CTG | TAC | CTG | CGG | 670 |
| Ile | Leu | Met | Leu | Ala | Arg | Arg | Lys | Glu | Arg | Leu | Pro | Leu | Tyr | Leu | Arg | |
| | | 210 | | | | | 215 | | | | | 220 | | | | |
| CTG | CTG | CAG | CGG | ATG | GAG | CAC | AGC | AAG | AAG | TAC | CCC | GGC | TTC | CTG | CTC | 718 |
| Leu | Leu | Gln | Arg | Met | Glu | His | Ser | Lys | Lys | Tyr | Pro | Gly | Phe | Leu | Leu | |
| | 225 | | | | | 230 | | | | | 235 | | | | | |
| AAC | AAC | TTC | CAC | AAC | CTG | CTG | CGC | TTC | TGG | CAG | CAG | CAC | TAC | CTG | CAC | 766 |
| Asn | Asn | Phe | His | Asn | Leu | Leu | Arg | Phe | Trp | Gln | Gln | His | Tyr | Leu | His | |
| 240 | | | | | 245 | | | | | 250 | | | | | 255 | |
| AAG | GAC | AAG | GAC | AGC | ACC | TGC | CTA | GAG | AAC | AGC | TCC | TGC | ATC | AGC | TTC | 814 |
| Lys | Asp | Lys | Asp | Ser | Thr | Cys | Leu | Glu | Asn | Ser | Ser | Cys | Ile | Ser | Phe | |
| | | | | 260 | | | | | 265 | | | | | 270 | | |
| TCA | TAC | TGG | AAG | GAG | ACA | GTG | TCC | ATC | CTG | TTG | AAC | CCG | GAC | CGG | CAG | 862 |
| Ser | Tyr | Trp | Lys | Glu | Thr | Val | Ser | Ile | Leu | Leu | Asn | Pro | Asp | Arg | Gln | |
| | | | 275 | | | | | 280 | | | | | 285 | | | |
| TCA | CCC | TCT | GCT | CTC | GTT | AGC | TAC | ATT | GAG | GAG | CCC | TAC | ATG | GAC | ATA | 910 |
| Ser | Pro | Ser | Ala | Leu | Val | Ser | Tyr | Ile | Glu | Glu | Pro | Tyr | Met | Asp | Ile | |
| | | 290 | | | | | 295 | | | | | 300 | | | | |
| GAC | AGG | GAC | TTC | ACT | GAG | GAG | TGACCTTGGG | | CCAGGCCTCG | | GGAGGCTGCT | | | | | 961 |
| Asp | Arg | Asp | Phe | Thr | Glu | Glu | | | | | | | | | | |
| | | 305 | | | | 310 | | | | | | | | | | |

| | | | | |
|---|---|---|---|---|
| GGGCCAGTGT | GGGTGAGCGT | GGGTACGATG | CCACACGCCC | TGCCCTGTTC | CCGTTCCTCC | 1021 |
| CTGCTGCTCT | CTGCCTGCCC | CAGGTCTTTG | GGTACAGGCT | TGGTGGGAGG | GAAGTCCTAG | 1081 |
| AAGCCCTTGG | TCCCCCTGGG | TCTGAGGGCC | CTAGGTCATG | GAGAGCCTCA | GTCCCCATAA | 1141 |
| TGAGGACAGG | GTACCATGCC | CACCTTTCCT | TCAGAACCCT | GGGGCCCAGG | GCCACCCAGA | 1201 |
| GGTAAGAGGA | CATTTAGCAT | TAGCTCTGTG | TGAGCTCCTG | CCGGTTTCTT | GGCTGTCAGT | 1261 |
| CAGTCCAGA | GTGGGGAGGA | AGATATGGGT | GACCCCCACC | CCCCATCTGT | GAGCCAAGCC | 1321 |
| TCCCTTGTCC | CTGGCCTTTG | GACCCAGGCA | AAGGCTTCTG | AGCCCTGGGC | AGGGGTGGTG | 1381 |
| GGTACCAGAG | AATGCTGCCT | TCCCCCAAGC | CTGCCCCTCT | GCCTCATTTT | CCTGTAGCTC | 1441 |
| CTCTGGTTCT | GTTTGCTCAT | TGGCCGCTGT | GTTCATCCAA | GGGGGTTCTC | CCAGAAGTGA | 1501 |
| GGGGCCTTTC | CCTCCATCCC | TTGGGGCACG | GGGCAGCTGT | GCCTGCCCTG | CCTCTGCCTG | 1561 |

AGGCAGCCGC TCCTGCCTGA GCCTGGACAT GGGGCCCTTC CTTGTGTTGC CAATTTATTA       1621

ACAGCAAATA AACCAATTAA ATGGAGACTA TTAAATAACT TTATTTTAAA AATGAAAAAA       1681

AAAAAAAAAA AAA                                                         1694

( 2 ) INFORMATION FOR SEQ ID NO:10:

( i ) SEQUENCE CHARACTERISTICS:
        ( A ) LENGTH: 310 amino acids
        ( B ) TYPE: amino acid
        ( D ) TOPOLOGY: linear ( i i ) MOLECULE TYPE: protein ( x i ) SEQUENCE DESCRIPTION: SEQ ID NO:10:

| | | | | | | | | | | | | | | |
|---|---|---|---|---|---|---|---|---|---|---|---|---|---|---|
| Ser | Leu | Lys | Ala | Asn | Ile | Pro | Glu | Val | Glu | Ala | Val | Leu | Asn | Thr | Asp |
| 1 | | | | 5 | | | | | 10 | | | | | 15 | |
| Arg | Ser | Leu | Val | Cys | Asp | Gly | Lys | Arg | Gly | Leu | Leu | Thr | Arg | Leu | Leu |
| | | | 20 | | | | | 25 | | | | | 30 | | |
| Gln | Val | Met | Lys | Lys | Glu | Pro | Ala | Glu | Ser | Ser | Phe | Arg | Phe | Trp | Gln |
| | | | 35 | | | | | 40 | | | | | 45 | | |
| Ala | Arg | Ala | Val | Glu | Ser | Phe | Leu | Arg | Gly | Thr | Thr | Ser | Tyr | Ala | Asp |
| | | | 50 | | | | | 55 | | | | | 60 | | |
| Gln | Met | Phe | Leu | Leu | Lys | Arg | Gly | Leu | Leu | Glu | His | Ile | Leu | Tyr | Cys |
| 65 | | | | | 70 | | | | | 75 | | | | | 80 |
| Ile | Val | Asp | Ser | Glu | Cys | Lys | Ser | Arg | Asp | Val | Leu | Gln | Ser | Tyr | Phe |
| | | | | 85 | | | | | 90 | | | | | 95 | |
| Asp | Leu | Leu | Gly | Glu | Leu | Met | Lys | Phe | Asn | Val | Asp | Ala | Phe | Lys | Arg |
| | | | 100 | | | | | 105 | | | | | 110 | | |
| Phe | Asn | Lys | Tyr | Ile | Asn | Thr | Asp | Ala | Lys | Phe | Gln | Val | Phe | Leu | Lys |
| | | | 115 | | | | | 120 | | | | | 125 | | |
| Gln | Ile | Asn | Ser | Ser | Leu | Val | Asp | Ser | Asn | Met | Leu | Val | Arg | Cys | Val |
| | | | 130 | | | | | 135 | | | | | 140 | | |
| Thr | Leu | Ser | Leu | Asp | Arg | Phe | Glu | Asn | Gln | Val | Asp | Met | Lys | Val | Ala |
| 145 | | | | | 150 | | | | | 155 | | | | | 160 |
| Glu | Val | Leu | Ser | Glu | Cys | Arg | Leu | Leu | Ala | Tyr | Ile | Ser | Gln | Val | Pro |
| | | | | 165 | | | | | 170 | | | | | 175 | |
| Thr | Gln | Met | Ser | Phe | Leu | Phe | Arg | Leu | Ile | Asn | Ile | Ile | His | Val | Gln |
| | | | 180 | | | | | 185 | | | | | 190 | | |
| Thr | Leu | Thr | Gln | Glu | Asn | Val | Ser | Cys | Leu | Asn | Thr | Ser | Leu | Val | Ile |
| | | | 195 | | | | | 200 | | | | | 205 | | |
| Leu | Met | Leu | Ala | Arg | Arg | Lys | Glu | Arg | Leu | Pro | Leu | Tyr | Leu | Arg | Leu |
| | | | 210 | | | | | 215 | | | | | 220 | | |
| Leu | Gln | Arg | Met | Glu | His | Ser | Lys | Lys | Tyr | Pro | Gly | Phe | Leu | Leu | Asn |
| 225 | | | | | 230 | | | | | 235 | | | | | 240 |
| Asn | Phe | His | Asn | Leu | Leu | Arg | Phe | Trp | Gln | Gln | His | Tyr | Leu | His | Lys |
| | | | | 245 | | | | | 250 | | | | | 255 | |
| Asp | Lys | Asp | Ser | Thr | Cys | Leu | Glu | Asn | Ser | Ser | Cys | Ile | Ser | Phe | Ser |
| | | | 260 | | | | | 265 | | | | | 270 | | |
| Tyr | Trp | Lys | Glu | Thr | Val | Ser | Ile | Leu | Leu | Asn | Pro | Asp | Arg | Gln | Ser |
| | | | 275 | | | | | 280 | | | | | 285 | | |
| Pro | Ser | Ala | Leu | Val | Ser | Tyr | Ile | Glu | Glu | Pro | Tyr | Met | Asp | Ile | Asp |
| | | | 290 | | | | | 295 | | | | | 300 | | |
| Arg | Asp | Phe | Thr | Glu | Glu | | | | | | | | | | |
| 305 | | | | | 310 | | | | | | | | | | |

( 2 ) INFORMATION FOR SEQ ID NO:11:

( i ) SEQUENCE CHARACTERISTICS:
        ( A ) LENGTH: 2735 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 2..1822

( x i ) SEQUENCE DESCRIPTION: SEQ ID NO:11:

```
G GAG ATC AGT CGG AAG GTG TAC AAG GGA ATG TTA GAC CTC CTC AAG        46
  Glu Ile Ser Arg Lys Val Tyr Lys Gly Met Leu Asp Leu Leu Lys
  1               5                  10                      15

TGT ACA GTC CTC AGC TTG GAG CAG TCC TAT GCC CAC GCG GGT CTG GGT      94
Cys Thr Val Leu Ser Leu Glu Gln Ser Tyr Ala His Ala Gly Leu Gly
                20                  25                  30

GGC ATG GCC AGC ATC TTT GGG CTT TTG GAG ATT GCC CAG ACC CAC TAC     142
Gly Met Ala Ser Ile Phe Gly Leu Leu Glu Ile Ala Gln Thr His Tyr
                35                  40                  45

TAT AGT AAA GAA CCA GAC AAG CGG AAG AGA AGT CCA ACA GAA AGT GTA     190
Tyr Ser Lys Glu Pro Asp Lys Arg Lys Arg Ser Pro Thr Glu Ser Val
            50                  55                  60

AAT ACC CCA GTT GGC AAG GAT CCT GGC CTA GCT GGG CGG GGG GAC CCA     238
Asn Thr Pro Val Gly Lys Asp Pro Gly Leu Ala Gly Arg Gly Asp Pro
        65                  70                  75

AAG GCT ATG GCA CAA CTG AGA GTT CCA CAA CTG GGA CCT CGG GCA CCA     286
Lys Ala Met Ala Gln Leu Arg Val Pro Gln Leu Gly Pro Arg Ala Pro
80                  85                  90                  95

AGT GCC ACA GGA AAG GGT CCT AAG GAA CTG GAC ACC AGA AGT TTA AAG     334
Ser Ala Thr Gly Lys Gly Pro Lys Glu Leu Asp Thr Arg Ser Leu Lys
                100                 105                 110

GAA GAA AAT TTT ATA GCA TCT ATT GGG CCT GAA GTA ATC AAA CCT GTC     382
Glu Glu Asn Phe Ile Ala Ser Ile Gly Pro Glu Val Ile Lys Pro Val
                115                 120                 125

TTT GAC CTT GGT GAG ACA GAG GAG AAA AAG TCC CAG ATC AGC GCA GAC     430
Phe Asp Leu Gly Glu Thr Glu Glu Lys Lys Ser Gln Ile Ser Ala Asp
            130                 135                 140

AGT GGT GTG AGC CTG ACG TCT AGT TCC CAG AGG ACT GAT CAA GAC TCT     478
Ser Gly Val Ser Leu Thr Ser Ser Ser Gln Arg Thr Asp Gln Asp Ser
        145                 150                 155

GTC ATC GGC GTG AGT CCA GCT GTT ATG ATC CGC AGC TCA AGT CAG GAT     526
Val Ile Gly Val Ser Pro Ala Val Met Ile Arg Ser Ser Ser Gln Asp
160                 165                 170                 175

TCT GAA GTT AGC ACC GTG GTG AGT AAT AGC TCT GGA GAG ACC CTT GGA     574
Ser Glu Val Ser Thr Val Val Ser Asn Ser Ser Gly Glu Thr Leu Gly
                180                 185                 190

GCT GAC AGT GAC TTG AGC AGC AAT GCA GGT GAT GGA CCA GGT GGC GAG     622
Ala Asp Ser Asp Leu Ser Ser Asn Ala Gly Asp Gly Pro Gly Gly Glu
                195                 200                 205

GGC AGT GTT CAC CTG GCA AGC TCT CGG GGC ACT TTG TCT GAT AGT GAA     670
Gly Ser Val His Leu Ala Ser Ser Arg Gly Thr Leu Ser Asp Ser Glu
            210                 215                 220

ATT GAG ACC AAC TCT GCC ACA AGC ACC ATC TTT GGT AAA GCC CAC AGC     718
Ile Glu Thr Asn Ser Ala Thr Ser Thr Ile Phe Gly Lys Ala His Ser
        225                 230                 235
```

| | | | | | | | | | | | | | | | | |
|---|---|---|---|---|---|---|---|---|---|---|---|---|---|---|---|---|
| TTG | AAG | CCA | AGC | ATA | AAG | GAG | AAG | CTG | GCA | GGC | AGC | CCC | ATT | CGT | ACT | 766 |
| Leu | Lys | Pro | Ser | Ile | Lys | Glu | Lys | Leu | Ala | Gly | Ser | Pro | Ile | Arg | Thr | |
| 240 | | | | 245 | | | | | 250 | | | | | 255 | | |
| TCT | GAA | GAT | GTG | AGC | CAG | CGA | GTC | TAT | CTC | TAT | GAG | GGA | CTC | CTA | GGC | 814 |
| Ser | Glu | Asp | Val | Ser | Gln | Arg | Val | Tyr | Leu | Tyr | Glu | Gly | Leu | Leu | Gly | |
| | | | 260 | | | | | 265 | | | | | 270 | | | |
| AAA | GAG | CGT | TCT | ACT | TTA | TGG | GAC | CAA | ATG | CAA | TTC | TGG | GAA | GAT | GCC | 862 |
| Lys | Glu | Arg | Ser | Thr | Leu | Trp | Asp | Gln | Met | Gln | Phe | Trp | Glu | Asp | Ala | |
| | | | 275 | | | | | 280 | | | | | 285 | | | |
| TTC | TTA | GAT | GCT | GTG | ATG | TTG | GAG | AGA | GAA | GGG | ATG | GGT | ATG | GAC | CAG | 910 |
| Phe | Leu | Asp | Ala | Val | Met | Leu | Glu | Arg | Glu | Gly | Met | Gly | Met | Asp | Gln | |
| | | 290 | | | | | 295 | | | | | 300 | | | | |
| GGT | CCC | CAG | GAA | ATG | ATC | GAC | AGG | TAC | CTG | TCC | CTT | GGA | GAA | CAT | GAC | 958 |
| Gly | Pro | Gln | Glu | Met | Ile | Asp | Arg | Tyr | Leu | Ser | Leu | Gly | Glu | His | Asp | |
| | 305 | | | | | 310 | | | | | 315 | | | | | |
| CGG | AAG | CGC | CTG | GAA | GAT | GAT | GAA | GAT | CGC | TTG | CTG | GCC | ACA | CTT | CTG | 1006 |
| Arg | Lys | Arg | Leu | Glu | Asp | Asp | Glu | Asp | Arg | Leu | Leu | Ala | Thr | Leu | Leu | |
| 320 | | | | | 325 | | | | | 330 | | | | | 335 | |
| CAC | AAC | CTC | ATC | TCC | TAC | ATG | CTG | CTG | ATG | AAG | GTA | AAT | AAG | AAT | GAC | 1054 |
| His | Asn | Leu | Ile | Ser | Tyr | Met | Leu | Leu | Met | Lys | Val | Asn | Lys | Asn | Asp | |
| | | | | 340 | | | | | 345 | | | | | 350 | | |
| ATC | CGC | AAG | AAG | GTG | AGG | CGC | CTA | ATG | GGA | AAG | TCG | CAC | ATT | GGG | CTT | 1102 |
| Ile | Arg | Lys | Lys | Val | Arg | Arg | Leu | Met | Gly | Lys | Ser | His | Ile | Gly | Leu | |
| | | | | 355 | | | | | 360 | | | | | 365 | | |
| GTG | TAC | AGC | CAG | CAA | ATC | AAT | GAG | GTG | CTT | GAT | CAG | CTG | GCG | AAC | CTG | 1150 |
| Val | Tyr | Ser | Gln | Gln | Ile | Asn | Glu | Val | Leu | Asp | Gln | Leu | Ala | Asn | Leu | |
| | | 370 | | | | | 375 | | | | | 380 | | | | |
| AAT | GGA | CGC | GAT | CTC | TCT | ATC | TGG | TCC | AGT | GGC | AGC | CGG | CAC | ATG | AAG | 1198 |
| Asn | Gly | Arg | Asp | Leu | Ser | Ile | Trp | Ser | Ser | Gly | Ser | Arg | His | Met | Lys | |
| | 385 | | | | | 390 | | | | | 395 | | | | | |
| AAG | CAG | ACA | TTT | GTG | GTA | CAT | GCA | GGG | ACA | GAT | ACA | AAC | GGA | GAT | ATC | 1246 |
| Lys | Gln | Thr | Phe | Val | Val | His | Ala | Gly | Thr | Asp | Thr | Asn | Gly | Asp | Ile | |
| 400 | | | | | 405 | | | | | 410 | | | | | 415 | |
| TTT | TTC | ATG | GAG | GTG | TGC | GAT | GAC | TGT | GTG | GTG | TTG | CGT | AGT | AAC | ATC | 1294 |
| Phe | Phe | Met | Glu | Val | Cys | Asp | Asp | Cys | Val | Val | Leu | Arg | Ser | Asn | Ile | |
| | | | | 420 | | | | | 425 | | | | | 430 | | |
| GGA | ACA | GTG | TAT | GAG | CGC | TGG | TGG | TAC | GAG | AAG | CTC | ATC | AAC | ATG | ACC | 1342 |
| Gly | Thr | Val | Tyr | Glu | Arg | Trp | Trp | Tyr | Glu | Lys | Leu | Ile | Asn | Met | Thr | |
| | | | 435 | | | | | 440 | | | | | 445 | | | |
| TAC | TGT | CCC | AAG | ACG | AAG | GTG | TTG | TGC | TTG | TGG | CGT | AGA | AAT | GGC | TCT | 1390 |
| Tyr | Cys | Pro | Lys | Thr | Lys | Val | Leu | Cys | Leu | Trp | Arg | Arg | Asn | Gly | Ser | |
| | | 450 | | | | | 455 | | | | | 460 | | | | |
| GAG | ACC | CAG | CTC | AAC | AAG | TTC | TAT | ACT | AAA | AAG | TGT | CGG | GAG | CTG | TAC | 1438 |
| Glu | Thr | Gln | Leu | Asn | Lys | Phe | Tyr | Thr | Lys | Lys | Cys | Arg | Glu | Leu | Tyr | |
| | 465 | | | | | 470 | | | | | 475 | | | | | |
| TAC | TGT | GTG | AAG | GAC | AGC | ATG | GAG | CGC | GCT | GCC | GCC | CGA | CAG | CAA | AGC | 1486 |
| Tyr | Cys | Val | Lys | Asp | Ser | Met | Glu | Arg | Ala | Ala | Ala | Arg | Gln | Gln | Ser | |
| 480 | | | | | 485 | | | | | 490 | | | | | 495 | |
| ATC | AAA | CCC | GGA | CCT | GAA | TTG | GGT | GGC | GAG | TTC | CCT | GTG | CAG | GAC | CTG | 1534 |
| Ile | Lys | Pro | Gly | Pro | Glu | Leu | Gly | Gly | Glu | Phe | Pro | Val | Gln | Asp | Leu | |
| | | | | 500 | | | | | 505 | | | | | 510 | | |
| AAG | ACT | GGT | GAG | GGT | GGC | CTG | CTG | CAG | GTG | ACC | CTG | GAA | GGG | ATC | AAC | 1582 |
| Lys | Thr | Gly | Glu | Gly | Gly | Leu | Leu | Gln | Val | Thr | Leu | Glu | Gly | Ile | Asn | |
| | | | | 515 | | | | | 520 | | | | | 525 | | |
| CTC | AAA | TTC | ATG | CAC | AAT | CAG | GTT | TTC | ATA | GAG | CTG | AAT | CAC | ATT | AAA | 1630 |
| Leu | Lys | Phe | Met | His | Asn | Gln | Val | Phe | Ile | Glu | Leu | Asn | His | Ile | Lys | |
| | | | 530 | | | | | 535 | | | | | 540 | | | |
| AAG | TGC | AAT | ACA | GTT | CGA | GGC | GTC | TTT | GTC | CTG | GAG | GAA | TTT | GTT | CCT | 1678 |
| Lys | Cys | Asn | Thr | Val | Arg | Gly | Val | Phe | Val | Leu | Glu | Glu | Phe | Val | Pro | |
| | | | 545 | | | | | 550 | | | | | 555 | | | |

| | | | | | | | | | | | | | | | |
|---|---|---|---|---|---|---|---|---|---|---|---|---|---|---|---|
| GAA | ATT | AAA | GAA | GTG | GTG | AGC | CAC | AAG | TAC | AAG | ACA | CCA | ATG | GCC | CAC | 1726
| Glu | Ile | Lys | Glu | Val | Val | Ser | His | Lys | Tyr | Lys | Thr | Pro | Met | Ala | His |
| 560 | | | | 565 | | | | | 570 | | | | | | 575 |
| GAA | ATC | TGC | TAC | TCC | GTA | TTA | TGT | CTC | TTC | TCG | TAC | GTG | GCT | GCA | GTT | 1774
| Glu | Ile | Cys | Tyr | Ser | Val | Leu | Cys | Leu | Phe | Ser | Tyr | Val | Ala | Ala | Val |
| | | | | 580 | | | | | 585 | | | | | 590 | |
| CAT | AGC | AGT | GAG | GAA | GAT | CTC | AGA | ACC | CCG | CCC | CGG | CCT | GTC | TCT | AGC | 1822
| His | Ser | Ser | Glu | Glu | Asp | Leu | Arg | Thr | Pro | Pro | Arg | Pro | Val | Ser | Ser |
| | | | 595 | | | | | 600 | | | | | 605 | | |

```
TGATGGAGAG  GGGCTACGCA  GCTGCCCCAG  CCCAGGGCAC  GCCCCTGGCC  CCTTGCTGTT   1882
CCCAAGTGCA  CGATGCTGCT  GTGACTGAGG  AGTGGATGAT  GCTCGTGTGT  CCTCTGCAAG   1942
CCCCCTGCTG  TGGCTTGGTT  GGTTACCGGT  TATGTGTCCC  TCTGAGTGTG  TCTTGAGCGT   2002
GTCCACCTTC  TCCCTCTCCA  CTCCCAGAAG  ACCAAACTGC  CTTCCCCTCA  GGGCTCAAGA   2062
ATGTGTACAG  TCTGTGGGGC  CGGTGTGAAC  CCACTATTTT  GTGTCCTTGA  GACATTTGTG   2122
TTGTGGTTCC  TTGTCCTTGT  CCCTGGCGTT  ATAACTGTCC  ACTGCAAGAG  TCTGGCTCTC   2182
CCTTCTCTGT  GACCCGGCAT  GACTGGGCGC  CTGGAGCAGT  TTCACTCTGT  GAGGAGTGAG   2242
GGAACCCTGG  GGCTCACCCT  CTCAGAGGAA  GGGCACAGAG  AGGAAGGGAA  GAATTGGGGG   2302
GCAGCCGGAG  TGAGTGGCAG  CCTCCCTGCT  TCCTTCTGCA  TTCCCAAGCC  GGCAGCTACT   2362
GCCCAGGGCC  CGCAGTGTTG  GCTGCTGCCT  GCCACAGCCT  CTGTGACTGC  AGTGGAGCGG   2422
CGAATTCCCT  GTGGCCTGCC  ACGCCTTCGG  CATCAGAGGA  TGGAGTGGTC  GAGGCTAGTG   2482
GAGTCCCAGG  GACCGCTGGC  TGCTCTGCCT  GAGCATCAGG  GAGGGGGCAG  GAAAGACCAA   2542
GCTGGGTTTG  CACATCTGTC  TGCAGGCTGT  CTCTCCAGGC  ACGGGGTGTC  AGGAGGGAGA   2602
GACAGCCTGG  GTATGGGCAA  GAAATGACTG  TAAATATTTC  AGCCCCACAT  TATTTATAGA   2662
AAATGTACAG  TTGTGTGAAT  GTGAAATAAA  TGTCCTCAAC  TCCCAAAAAA  AAAAAAAAA    2722
AAAAAAAAAA  AAA                                                         2735
```

( 2 ) INFORMATION FOR SEQ ID NO:12:

( i ) SEQUENCE CHARACTERISTICS:
        ( A ) LENGTH: 607 amino acids
        ( B ) TYPE: amino acid
        ( D ) TOPOLOGY: linear ( i i ) MOLECULE TYPE: protein ( x i ) SEQUENCE DESCRIPTION: SEQ ID NO:12:

| | | | | | | | | | | | | | | |
|---|---|---|---|---|---|---|---|---|---|---|---|---|---|---|
| Glu | Ile | Ser | Arg | Lys | Val | Tyr | Lys | Gly | Met | Leu | Asp | Leu | Leu | Lys | Cys |
| 1 | | | | 5 | | | | | 10 | | | | | 15 |
| Thr | Val | Leu | Ser | Leu | Glu | Gln | Ser | Tyr | Ala | His | Ala | Gly | Leu | Gly | Gly |
| | | | 20 | | | | | 25 | | | | | 30 | | |
| Met | Ala | Ser | Ile | Phe | Gly | Leu | Leu | Glu | Ile | Ala | Gln | Thr | His | Tyr | Tyr |
| | | 35 | | | | | 40 | | | | | 45 | | | |
| Ser | Lys | Glu | Pro | Asp | Lys | Arg | Lys | Arg | Ser | Pro | Thr | Glu | Ser | Val | Asn |
| 50 | | | | | 55 | | | | | 60 | | | | | |
| Thr | Pro | Val | Gly | Lys | Asp | Pro | Gly | Leu | Ala | Gly | Arg | Gly | Asp | Pro | Lys |
| 65 | | | | | 70 | | | | | 75 | | | | | 80 |
| Ala | Met | Ala | Gln | Leu | Arg | Val | Pro | Gln | Leu | Gly | Pro | Arg | Ala | Pro | Ser |
| | | | | 85 | | | | | 90 | | | | | 95 | |
| Ala | Thr | Gly | Lys | Gly | Pro | Lys | Glu | Leu | Asp | Thr | Arg | Ser | Leu | Lys | Glu |
| | | | 100 | | | | | 105 | | | | | 110 | | |
| Glu | Asn | Phe | Ile | Ala | Ser | Ile | Gly | Pro | Glu | Val | Ile | Lys | Pro | Val | Phe |
| | | | 115 | | | | | 120 | | | | | 125 | | |

```
Asp Leu Gly Glu Thr Glu Glu Lys Lys Ser Gln Ile Ser Ala Asp Ser
    130             135                 140
Gly Val Ser Leu Thr Ser Ser Ser Gln Arg Thr Asp Gln Asp Ser Val
145             150                 155                 160
Ile Gly Val Ser Pro Ala Val Met Ile Arg Ser Ser Ser Gln Asp Ser
                165             170                 175
Glu Val Ser Thr Val Val Ser Asn Ser Gly Glu Thr Leu Gly Ala
            180             185                 190
Asp Ser Asp Leu Ser Ser Asn Ala Gly Asp Pro Gly Gly Glu Gly
        195             200             205
Ser Val His Leu Ala Ser Ser Arg Gly Thr Leu Ser Asp Ser Glu Ile
    210             215                 220
Glu Thr Asn Ser Ala Thr Ser Thr Ile Phe Gly Lys Ala His Ser Leu
225             230                 235                 240
Lys Pro Ser Ile Lys Glu Lys Leu Ala Gly Ser Pro Ile Arg Thr Ser
                245             250                 255
Glu Asp Val Ser Gln Arg Val Tyr Leu Tyr Glu Gly Leu Leu Gly Lys
            260             265                 270
Glu Arg Ser Thr Leu Trp Asp Met Gln Phe Trp Glu Asp Ala Phe
            275             280                 285
Leu Asp Ala Val Met Leu Glu Arg Glu Gly Met Gly Met Asp Gln Gly
290             295                 300
Pro Gln Glu Met Ile Asp Arg Tyr Leu Ser Leu Gly Glu His Asp Arg
305             310                 315                 320
Lys Arg Leu Glu Asp Asp Glu Asp Arg Leu Leu Ala Thr Leu Leu His
                325             330                 335
Asn Leu Ile Ser Tyr Met Leu Leu Met Lys Val Asn Lys Asn Asp Ile
            340             345                 350
Arg Lys Lys Val Arg Arg Leu Met Gly Lys Ser His Ile Gly Leu Val
            355             360                 365
Tyr Ser Gln Gln Ile Asn Glu Val Leu Asp Gln Leu Ala Asn Leu Asn
    370             375                 380
Gly Arg Asp Leu Ser Ile Trp Ser Ser Gly Ser Arg His Met Lys Lys
385             390                 395                 400
Gln Thr Phe Val Val His Ala Gly Thr Asp Thr Asn Gly Asp Ile Phe
                405             410                 415
Phe Met Glu Val Cys Asp Asp Cys Val Val Leu Arg Ser Asn Ile Gly
            420             425                 430
Thr Val Tyr Glu Arg Trp Trp Tyr Glu Lys Leu Ile Asn Met Thr Tyr
        435             440                 445
Cys Pro Lys Thr Lys Val Leu Cys Leu Trp Arg Arg Asn Gly Ser Glu
    450             455                 460
Thr Gln Leu Asn Lys Phe Tyr Thr Lys Lys Cys Arg Glu Leu Tyr Tyr
465             470                 475                 480
Cys Val Lys Asp Ser Met Glu Arg Ala Ala Ala Arg Gln Gln Ser Ile
                485             490                 495
Lys Pro Gly Pro Glu Leu Gly Gly Glu Phe Pro Val Gln Asp Leu Lys
            500             505                 510
Thr Gly Glu Gly Gly Leu Leu Gln Val Thr Leu Glu Gly Ile Asn Leu
        515             520                 525
Lys Phe Met His Asn Gln Val Phe Ile Glu Leu Asn His Ile Lys Lys
    530             535                 540
Cys Asn Thr Val Arg Gly Val Phe Val Leu Glu Glu Phe Val Pro Glu
545             550                 555                 560
```

```
Ile  Lys  Glu  Val  Val  Ser  His  Lys  Tyr  Lys  Thr  Pro  Met  Ala  His  Glu
               565                     570                     575

Ile  Cys  Tyr  Ser  Val  Leu  Cys  Leu  Phe  Ser  Tyr  Val  Ala  Ala  Val  His
               580                     585                     590

Ser  Ser  Glu  Glu  Asp  Leu  Arg  Thr  Pro  Pro  Arg  Pro  Val  Ser  Ser
          595                     600                     605
```

( 2 ) INFORMATION FOR SEQ ID NO:13:

( i ) SEQUENCE CHARACTERISTICS:
        ( A ) LENGTH: 3225 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 3..2846

( x i ) SEQUENCE DESCRIPTION: SEQ ID NO:13:

```
CC  CAG  ACT  CGC  CCC  GCC  CCA  GAG  ACT  GCG  CCT  GCG  CGG  GCA  CGA  GAC         47
    Gln  Thr  Arg  Pro  Ala  Pro  Glu  Thr  Ala  Pro  Ala  Arg  Ala  Arg  Asp
     1              5                    10                        15

ACC  CTC  TCC  GCG  ATG  ACT  GCC  AGC  TCA  GTG  GAG  CAG  CTG  CGG  AAG  GAG        95
Thr  Leu  Ser  Ala  Met  Thr  Ala  Ser  Ser  Val  Glu  Gln  Leu  Arg  Lys  Glu
                    20                    25                         30

GGC  AAT  GAG  CTG  TTC  AAA  TGT  GGA  GAC  TAC  GGG  GGC  GCC  CTG  GCG  GCC       143
Gly  Asn  Glu  Leu  Phe  Lys  Cys  Gly  Asp  Tyr  Gly  Gly  Ala  Leu  Ala  Ala
               35                    40                         45

TAC  ACT  CAG  GCC  CTG  GGT  CTG  GAC  GCG  ACG  CCC  CAG  GAC  CAG  GCC  GTT       191
Tyr  Thr  Gln  Ala  Leu  Gly  Leu  Asp  Ala  Thr  Pro  Gln  Asp  Gln  Ala  Val
          50                         55                    60

CTG  CAC  CGG  AAC  CGG  GCC  GCC  TGC  CAC  CTC  AAG  CTG  GAA  GAT  TAC  GAC       239
Leu  His  Arg  Asn  Arg  Ala  Ala  Cys  His  Leu  Lys  Leu  Glu  Asp  Tyr  Asp
     65                         70                    75

AAA  GCA  GAA  ACA  GAG  GCA  TCC  AAA  GCC  ATT  GAA  AAG  GAT  GGT  GGG  GAT       287
Lys  Ala  Glu  Thr  Glu  Ala  Ser  Lys  Ala  Ile  Glu  Lys  Asp  Gly  Gly  Asp
80                    85                         90                         95

GTC  AAA  GCA  CTC  TAC  CGG  CGG  AGC  CAA  GCC  CTA  GAG  AAG  CTG  GGC  CGC       335
Val  Lys  Ala  Leu  Tyr  Arg  Arg  Ser  Gln  Ala  Leu  Glu  Lys  Leu  Gly  Arg
                    100                        105                       110

CTG  GAC  CAG  GCT  GTC  CTT  GAC  CTG  CAG  AGA  TGT  GTG  AGC  TTG  GAG  CCC       383
Leu  Asp  Gln  Ala  Val  Leu  Asp  Leu  Gln  Arg  Cys  Val  Ser  Leu  Glu  Pro
               115                        120                  125

AAG  AAC  AAA  GTT  TTC  CAG  GAG  GCC  TTG  CGG  AAC  ATC  GGG  GGC  CAG  ATT       431
Lys  Asn  Lys  Val  Phe  Gln  Glu  Ala  Leu  Arg  Asn  Ile  Gly  Gly  Gln  Ile
          130                         135                  140

CAG  GAG  AAG  GTG  CGA  TAC  ATG  TCC  TCG  ACG  GAT  GCC  AAA  GTG  GAA  CAG       479
Gln  Glu  Lys  Val  Arg  Tyr  Met  Ser  Ser  Thr  Asp  Ala  Lys  Val  Glu  Gln
     145                        150                   155

ATG  TTT  CAG  ATA  CTG  TTG  GAC  CCA  GAA  GAG  AAG  GGC  ACT  GAG  AAA  AAG       527
Met  Phe  Gln  Ile  Leu  Leu  Asp  Pro  Glu  Glu  Lys  Gly  Thr  Glu  Lys  Lys
160                       165                   170                        175

CAA  AAG  GCT  TCT  CAG  AAC  CTG  GTG  GTG  CTG  GCC  AGG  GAG  GAT  GCT  GGA       575
Gln  Lys  Ala  Ser  Gln  Asn  Leu  Val  Val  Leu  Ala  Arg  Glu  Asp  Ala  Gly
               180                        185                       190

GCG  GAG  AAG  ATC  TTC  CGG  AGT  AAT  GGG  GTT  CAG  CTC  TTG  CAA  CGT  TTA       623
Ala  Glu  Lys  Ile  Phe  Arg  Ser  Asn  Gly  Val  Gln  Leu  Leu  Gln  Arg  Leu
          195                         200                  205
```

| | | | | | | | | | | | | | | | | |
|---|---|---|---|---|---|---|---|---|---|---|---|---|---|---|---|---|
| CTG | GAC | ATG | GGA | GAG | ACT | GAC | CTC | ATG | CTG | GCG | GCT | CTG | CGT | ACG | CTG | 671 |
| Leu | Asp | Met | Gly | Glu | Thr | Asp | Leu | Met | Leu | Ala | Ala | Leu | Arg | Thr | Leu | |
| | | 210 | | | | 215 | | | | 220 | | | | | | |
| GTT | GGC | ATT | TGC | TCT | GAG | CAT | CAG | TCA | CGG | ACA | GTG | GCA | ACC | CTG | AGC | 719 |
| Val | Gly | Ile | Cys | Ser | Glu | His | Gln | Ser | Arg | Thr | Val | Ala | Thr | Leu | Ser | |
| 225 | | | | | 230 | | | | | 235 | | | | | | |
| ATA | CTG | GGA | ACT | CGG | CGA | GTA | GTC | TCC | ATC | CTG | GGC | GTG | GAA | AGC | CAG | 767 |
| Ile | Leu | Gly | Thr | Arg | Arg | Val | Val | Ser | Ile | Leu | Gly | Val | Glu | Ser | Gln | |
| 240 | | | | | 245 | | | | | 250 | | | | | 255 | |
| GCT | GTG | TCC | CTG | GCT | GCC | TGC | CAC | CTG | CTG | CAG | GTT | ATG | TTT | GAT | GCC | 815 |
| Ala | Val | Ser | Leu | Ala | Ala | Cys | His | Leu | Leu | Gln | Val | Met | Phe | Asp | Ala | |
| | | | | 260 | | | | | 265 | | | | | 270 | | |
| CTC | AAG | GAA | GGT | GTC | AAA | AAA | GGC | TTC | CGA | GGC | AAA | GAA | GGT | GCC | ATC | 863 |
| Leu | Lys | Glu | Gly | Val | Lys | Lys | Gly | Phe | Arg | Gly | Lys | Glu | Gly | Ala | Ile | |
| | | | 275 | | | | | 280 | | | | | 285 | | | |
| ATT | GTG | GAT | CCT | GCC | CGG | GAG | CTG | AAG | GTC | CTC | ATC | AGT | AAC | CTC | TTA | 911 |
| Ile | Val | Asp | Pro | Ala | Arg | Glu | Leu | Lys | Val | Leu | Ile | Ser | Asn | Leu | Leu | |
| | | 290 | | | | 295 | | | | 300 | | | | | | |
| GAT | CTG | CTG | ACA | GAG | GTG | GGG | GTC | TCT | GGC | CAA | GGC | CGA | GAC | AAT | GCC | 959 |
| Asp | Leu | Leu | Thr | Glu | Val | Gly | Val | Ser | Gly | Gln | Gly | Arg | Asp | Asn | Ala | |
| 305 | | | | | 310 | | | | | 315 | | | | | | |
| CTG | ACC | CTC | CTG | ATT | AAA | GCG | GTG | CCC | CGG | AAG | TCT | CTC | AAG | GAC | CCC | 1007 |
| Leu | Thr | Leu | Leu | Ile | Lys | Ala | Val | Pro | Arg | Lys | Ser | Leu | Lys | Asp | Pro | |
| 320 | | | | | 325 | | | | | 330 | | | | | 335 | |
| AAC | AAC | AGC | CTC | ACC | CTC | TGG | GTC | ATC | GAC | CAA | GGT | CTG | AAA | AAG | ATT | 1055 |
| Asn | Asn | Ser | Leu | Thr | Leu | Trp | Val | Ile | Asp | Gln | Gly | Leu | Lys | Lys | Ile | |
| | | | | 340 | | | | | 345 | | | | | 350 | | |
| TTG | GAA | GTG | GGG | GGC | TCT | CTA | CAG | GAC | CCT | CCT | GGG | GAG | CTC | GCA | GTG | 1103 |
| Leu | Glu | Val | Gly | Gly | Ser | Leu | Gln | Asp | Pro | Pro | Gly | Glu | Leu | Ala | Val | |
| | | | 355 | | | | | 360 | | | | | 365 | | | |
| ACC | GCA | AAC | AGC | CGC | ATG | AGC | GCC | TCT | ATT | CTC | CTC | AGC | AAG | CTC | TTT | 1151 |
| Thr | Ala | Asn | Ser | Arg | Met | Ser | Ala | Ser | Ile | Leu | Leu | Ser | Lys | Leu | Phe | |
| | | 370 | | | | 375 | | | | 380 | | | | | | |
| GAT | GAC | CTC | AAG | TGT | GAT | GCG | GAG | AGG | GAG | AAT | TTC | CAC | AGA | CTT | TGT | 1199 |
| Asp | Asp | Leu | Lys | Cys | Asp | Ala | Glu | Arg | Glu | Asn | Phe | His | Arg | Leu | Cys | |
| 385 | | | | | 390 | | | | | 395 | | | | | | |
| GAA | AAC | TAC | ATC | AAG | AGC | TGG | TTT | GAG | GGC | CAA | GGG | CTG | GCC | GGG | AAG | 1247 |
| Glu | Asn | Tyr | Ile | Lys | Ser | Trp | Phe | Glu | Gly | Gln | Gly | Leu | Ala | Gly | Lys | |
| 400 | | | | | 405 | | | | | 410 | | | | | 415 | |
| CTA | CGG | GCC | ATC | CAG | ACG | GTG | TCC | TGC | CTC | CTG | CAG | GGC | CCA | TGT | GAC | 1295 |
| Leu | Arg | Ala | Ile | Gln | Thr | Val | Ser | Cys | Leu | Leu | Gln | Gly | Pro | Cys | Asp | |
| | | | | 420 | | | | | 425 | | | | | 430 | | |
| GCT | GGC | AAC | CGG | GCC | TTG | GAG | CTG | AGC | GGT | GTC | ATG | GAG | AGT | GTG | ATT | 1343 |
| Ala | Gly | Asn | Arg | Ala | Leu | Glu | Leu | Ser | Gly | Val | Met | Glu | Ser | Val | Ile | |
| | | | 435 | | | | | 440 | | | | | 445 | | | |
| GCT | CTG | TGT | GCC | TCT | GAG | CAG | GAG | GAG | GAG | CAG | CTG | GTG | GCC | GTG | GAG | 1391 |
| Ala | Leu | Cys | Ala | Ser | Glu | Gln | Glu | Glu | Glu | Gln | Leu | Val | Ala | Val | Glu | |
| | | 450 | | | | | 455 | | | | | 460 | | | | |
| GCT | CTG | ATC | CAT | GCA | GCC | GGC | AAG | GCT | AAG | CGG | GCC | TCA | TTC | ATC | ACT | 1439 |
| Ala | Leu | Ile | His | Ala | Ala | Gly | Lys | Ala | Lys | Arg | Ala | Ser | Phe | Ile | Thr | |
| 465 | | | | | 470 | | | | | 475 | | | | | | |
| GCC | AAT | GGT | GTC | TCG | CTG | CTG | AAG | GAC | CTA | TAT | AAG | TGC | AGC | GAG | AAG | 1487 |
| Ala | Asn | Gly | Val | Ser | Leu | Leu | Lys | Asp | Leu | Tyr | Lys | Cys | Ser | Glu | Lys | |
| 480 | | | | | 485 | | | | | 490 | | | | | 495 | |
| GAC | AGC | ATC | CGC | ATC | CGG | GCG | CTA | GTG | GGA | CTC | TGT | AAG | CTC | GGT | TCG | 1535 |
| Asp | Ser | Ile | Arg | Ile | Arg | Ala | Leu | Val | Gly | Leu | Cys | Lys | Leu | Gly | Ser | |
| | | | | 500 | | | | | 505 | | | | | 510 | | |
| GCT | GGA | GGG | ACT | GAC | TTC | AGC | ATG | AAG | CAG | TTT | GCT | GAA | GGC | TCC | ACT | 1583 |
| Ala | Gly | Gly | Thr | Asp | Phe | Ser | Met | Lys | Gln | Phe | Ala | Glu | Gly | Ser | Thr | |
| | | | 515 | | | | | 520 | | | | | 525 | | | |

```
CTC  AAA  CTG  GCT  AAG  CAG  TGT  CGA  AAG  TGG  CTG  TGC  AAT  GAC  CAG  ATC   1631
Leu  Lys  Leu  Ala  Lys  Gln  Cys  Arg  Lys  Trp  Leu  Cys  Asn  Asp  Gln  Ile
          530            535                           540

GAC  GCA  GGC  ACT  CGG  CGC  TGG  GCA  GTG  GAG  GGC  CTG  GCT  TAC  CTG  ACC   1679
Asp  Ala  Gly  Thr  Arg  Arg  Trp  Ala  Val  Glu  Gly  Leu  Ala  Tyr  Leu  Thr
     545                           550                           555

TTT  GAT  GCC  GAC  GTG  AAG  GAA  GAG  TTT  GTG  GAG  GAT  GCG  GCT  GCT  CTG   1727
Phe  Asp  Ala  Asp  Val  Lys  Glu  Glu  Phe  Val  Glu  Asp  Ala  Ala  Ala  Leu
560                      565                      570                      575

AAA  GCT  CTG  TTC  CAG  CTC  AGC  AGG  TTG  GAG  GAG  AGG  TCA  GTG  CTC  TTT   1775
Lys  Ala  Leu  Phe  Gln  Leu  Ser  Arg  Leu  Glu  Glu  Arg  Ser  Val  Leu  Phe
                    580                      585                      590

GCG  GTG  GCC  TCA  GCG  CTG  GTG  AAC  TGC  ACC  AAC  AGC  TAT  GAC  TAC  GAG   1823
Ala  Val  Ala  Ser  Ala  Leu  Val  Asn  Cys  Thr  Asn  Ser  Tyr  Asp  Tyr  Glu
               595                      600                      605

GAG  CCC  GAC  CCC  AAG  ATG  GTG  GAG  CTG  GCC  AAG  TAT  GCC  AAG  CAG  CAT   1871
Glu  Pro  Asp  Pro  Lys  Met  Val  Glu  Leu  Ala  Lys  Tyr  Ala  Lys  Gln  His
          610                      615                      620

GTG  CCC  GAG  CAG  CAC  CCC  AAG  GAC  AAG  CCA  AGC  TTC  GTG  CGG  GCT  CGG   1919
Val  Pro  Glu  Gln  His  Pro  Lys  Asp  Lys  Pro  Ser  Phe  Val  Arg  Ala  Arg
     625                      630                      635

GTG  AAG  AAG  CTG  CTG  GCA  GCG  GGT  GTG  GTG  TCG  GCC  ATG  GTG  TGC  ATG   1967
Val  Lys  Lys  Leu  Leu  Ala  Ala  Gly  Val  Val  Ser  Ala  Met  Val  Cys  Met
640                      645                      650                      655

GTG  AAG  ACG  GAG  AGC  CCT  GTG  CTG  ACC  AGT  TCC  TGC  AGA  GAG  CTG  CTC   2015
Val  Lys  Thr  Glu  Ser  Pro  Val  Leu  Thr  Ser  Ser  Cys  Arg  Glu  Leu  Leu
                    660                      665                      670

TCC  AGG  GTC  TTC  TTG  GCT  TTA  GTG  GAA  GAG  GTA  GAG  GAC  CGA  GGC  ACT   2063
Ser  Arg  Val  Phe  Leu  Ala  Leu  Val  Glu  Glu  Val  Glu  Asp  Arg  Gly  Thr
               675                      680                      685

GTG  GTT  GCC  CAG  GGA  GGC  GGC  AGG  GCG  CTG  ATC  CCG  CTG  GCC  CTG  GAA   2111
Val  Val  Ala  Gln  Gly  Gly  Gly  Arg  Ala  Leu  Ile  Pro  Leu  Ala  Leu  Glu
          690                      695                      700

GGC  ACG  GAC  GTG  GGG  CAG  ACA  AAG  GCA  GCC  CAG  GCC  CTT  GCC  AAG  CTC   2159
Gly  Thr  Asp  Val  Gly  Gln  Thr  Lys  Ala  Ala  Gln  Ala  Leu  Ala  Lys  Leu
     705                      710                      715

ACC  ATC  ACC  TCC  AAC  CCG  GAG  ATG  ACC  TTC  CCT  GGC  GAG  CGG  ATC  TAT   2207
Thr  Ile  Thr  Ser  Asn  Pro  Glu  Met  Thr  Phe  Pro  Gly  Glu  Arg  Ile  Tyr
720                      725                      730                      735

GAG  GTG  GTC  CGG  CCC  CTC  GTC  TCC  CTG  TTG  CAC  CTC  AAC  TGC  TCA  GGC   2255
Glu  Val  Val  Arg  Pro  Leu  Val  Ser  Leu  Leu  His  Leu  Asn  Cys  Ser  Gly
                    740                      745                      750

CTG  CAG  AAC  TTC  GAG  GCG  CTC  ATG  GCC  CTA  ACA  AAC  CTG  GCT  GGG  ATC   2303
Leu  Gln  Asn  Phe  Glu  Ala  Leu  Met  Ala  Leu  Thr  Asn  Leu  Ala  Gly  Ile
               755                      760                      765

AGC  GAG  AGG  CTC  CGG  CAG  AAG  ATC  CTG  AAG  GAG  AAG  GCT  GTG  CCC  ATG   2351
Ser  Glu  Arg  Leu  Arg  Gln  Lys  Ile  Leu  Lys  Glu  Lys  Ala  Val  Pro  Met
          770                      775                      780

ATA  GAA  GGC  TAC  ATG  TTT  GAG  GAG  CAT  GAG  ATG  ATC  CGC  CGG  GCA  GCC   2399
Ile  Glu  Gly  Tyr  Met  Phe  Glu  Glu  His  Glu  Met  Ile  Arg  Arg  Ala  Ala
     785                      790                      795

ACG  GAG  TGC  ATG  TGT  AAC  TTG  GCC  ATG  AGC  AAG  GAG  GTG  CAG  GAC  CTC   2447
Thr  Glu  Cys  Met  Cys  Asn  Leu  Ala  Met  Ser  Lys  Glu  Val  Gln  Asp  Leu
800                      805                      810                      815

TTC  GAA  GCC  CAG  GGC  AAT  GAC  CGA  CTG  AAG  CTG  CTG  GTG  CTG  TAC  AGT   2495
Phe  Glu  Ala  Gln  Gly  Asn  Asp  Arg  Leu  Lys  Leu  Leu  Val  Leu  Tyr  Ser
                    820                      825                      830

GGA  GAG  GAT  GAT  GAG  CTG  CTA  CAG  CGG  GCA  GCT  GCC  GGG  GGC  TTG  GCC   2543
Gly  Glu  Asp  Asp  Glu  Leu  Leu  Gln  Arg  Ala  Ala  Ala  Gly  Gly  Leu  Ala
               835                      840                      845
```

```
ATG CTT ACC TCC ATG CGG CCC ACG CTC TGC AGC CGC ATT CCC CAA GTG      2591
Met Leu Thr Ser Met Arg Pro Thr Leu Cys Ser Arg Ile Pro Gln Val
            850                 855                 860

ACC ACA CAC TGG CTG GAG ATC CTG CAG GCC CTG CTT CTG AGC TCC AAC      2639
Thr Thr His Trp Leu Glu Ile Leu Gln Ala Leu Leu Leu Ser Ser Asn
    865                 870                 875

CAG GAG CTG CAG CAC CGG GGT GCT GTG GTG GTG CTG AAC ATG GTG GAG      2687
Gln Glu Leu Gln His Arg Gly Ala Val Val Val Leu Asn Met Val Glu
880                 885                 890                 895

GCC TCG AGG GAG ATT GCC AGC ACC CTG ATG GAG AGT GAG ATG ATG GAG      2735
Ala Ser Arg Glu Ile Ala Ser Thr Leu Met Glu Ser Glu Met Met Glu
                900                 905                 910

ATC TTG TCA GTG CTA GCT AAG GGT GAC CAC AGC CCT GTC ACA AGG GCT      2783
Ile Leu Ser Val Leu Ala Lys Gly Asp His Ser Pro Val Thr Arg Ala
            915                 920                 925

GCT GCA GCC TGC CTG GAC AAA GCA GTG GAA TAT GGG CTT ATC CAA CCC      2831
Ala Ala Ala Cys Leu Asp Lys Ala Val Glu Tyr Gly Leu Ile Gln Pro
        930                 935                 940

AAC CAA GAT GGA GAG TGAGGGGGTT GTCCCTGGGC CCAAGGCTCA TGCACACGCT      2886
Asn Gln Asp Gly Glu
        945

ACCTATTGTG GCACGGAGAG TAAGGACGGA AGCAGCTTTG GCTGGTGGTG GCTGGCATGC    2946

CCAATACTCT TGCCCATCCT CGCTTGCTGC CCTAGGATGT CCTCTGTTCT GAGTCAGCGG    3006

CCACGTTCAG TCACACAGCC CTGCTTGGCC AGCACTGCCT GCAGCCTCAC TCAGAGGGGC    3066

CCTTTTTCTG TACTACTGTA GTCAGCTGGG AATGGGGAAG GTGCATCCCA ACACAGCCTG    3126

TGGATCCTGG GGCATTTGGA AGGGCGCACA CATCAGCAGC CTCACCAGCT GTGAGCCTGC    3186

TATCAGGCCT GCCCCTCCAA TAAAAGTGTG TAGAACTCC                           3225
```

( 2 ) INFORMATION FOR SEQ ID NO:14:

( i ) SEQUENCE CHARACTERISTICS:
        ( A ) LENGTH: 948 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

```
Gln Thr Arg Pro Ala Pro Glu Thr Ala Pro Ala Arg Ala Arg Asp Thr
 1               5                  10                  15

Leu Ser Ala Met Thr Ala Ser Ser Val Gln Leu Arg Lys Glu Gly
             20                  25                  30

Asn Glu Leu Phe Lys Cys Gly Asp Tyr Gly Gly Ala Leu Ala Ala Tyr
             35                  40                  45

Thr Gln Ala Leu Gly Leu Asp Ala Thr Pro Gln Asp Gln Ala Val Leu
         50                  55                  60

His Arg Asn Arg Ala Ala Cys His Leu Lys Leu Glu Asp Tyr Asp Lys
 65                  70                  75                  80

Ala Glu Thr Glu Ala Ser Lys Ala Ile Glu Lys Asp Gly Gly Asp Val
                 85                  90                  95

Lys Ala Leu Tyr Arg Arg Ser Gln Ala Leu Glu Lys Leu Gly Arg Leu
            100                 105                 110

Asp Gln Ala Val Leu Asp Leu Gln Arg Cys Val Ser Leu Glu Pro Lys
            115                 120                 125

Asn Lys Val Phe Gln Glu Ala Leu Arg Asn Ile Gly Gly Gln Ile Gln
        130                 135                 140
```

| Glu 145 | Lys | Val | Arg | Tyr | Met 150 | Ser | Ser | Thr | Asp | Ala 155 | Lys | Val | Glu | Gln | Met 160 |
| Phe | Gln | Ile | Leu | Leu 165 | Asp | Pro | Glu | Glu | Lys 170 | Gly | Thr | Glu | Lys | Lys 175 | Gln |
| Lys | Ala | Ser | Gln 180 | Asn | Leu | Val | Val | Leu 185 | Ala | Arg | Glu | Asp | Gly 190 | Ala |
| Glu | Lys | Ile 195 | Phe | Arg | Ser | Asn | Gly 200 | Val | Gln | Leu | Leu | Gln 205 | Arg | Leu | Leu |
| Asp | Met 210 | Gly | Glu | Thr | Asp | Leu 215 | Met | Leu | Ala | Ala | Leu 220 | Arg | Thr | Leu | Val |
| Gly 225 | Ile | Cys | Ser | Glu | His 230 | Gln | Ser | Arg | Thr | Val 235 | Ala | Thr | Leu | Ser | Ile 240 |
| Leu | Gly | Thr | Arg | Arg 245 | Val | Val | Ser | Ile | Leu 250 | Gly | Val | Glu | Ser | Gln 255 | Ala |
| Val | Ser | Leu | Ala 260 | Ala | Cys | His | Leu | Leu 265 | Gln | Val | Met | Phe | Asp 270 | Ala | Leu |
| Lys | Glu | Gly | Val 275 | Lys | Lys | Gly | Phe 280 | Arg | Gly | Lys | Glu | Gly 285 | Ala | Ile | Ile |
| Val | Asp 290 | Pro | Ala | Arg | Glu | Leu 295 | Lys | Val | Leu | Ile | Ser 300 | Asn | Leu | Leu | Asp |
| Leu 305 | Leu | Thr | Glu | Val | Gly 310 | Val | Ser | Gly | Gln | Gly 315 | Arg | Asp | Asn | Ala | Leu 320 |
| Thr | Leu | Leu | Ile | Lys 325 | Ala | Val | Pro | Arg | Lys 330 | Ser | Leu | Lys | Asp | Pro 335 | Asn |
| Asn | Ser | Leu | Thr 340 | Leu | Trp | Val | Ile | Asp 345 | Gln | Gly | Leu | Lys | Lys 350 | Ile | Leu |
| Glu | Val | Gly 355 | Gly | Ser | Leu | Gln | Asp 360 | Pro | Pro | Gly | Glu | Leu 365 | Ala | Val | Thr |
| Ala | Asn 370 | Ser | Arg | Met | Ser | Ala 375 | Ser | Ile | Leu | Leu | Ser 380 | Lys | Leu | Phe | Asp |
| Asp 385 | Leu | Lys | Cys | Asp | Ala 390 | Glu | Arg | Glu | Asn | Phe 395 | His | Arg | Leu | Cys | Glu 400 |
| Asn | Tyr | Ile | Lys | Ser 405 | Trp | Phe | Glu | Gly | Gln 410 | Gly | Leu | Ala | Gly | Lys 415 | Leu |
| Arg | Ala | Ile | Gln 420 | Thr | Val | Ser | Cys | Leu 425 | Leu | Gln | Gly | Pro | Cys 430 | Asp | Ala |
| Gly | Asn | Arg 435 | Ala | Leu | Glu | Leu | Ser 440 | Gly | Val | Met | Glu | Ser 445 | Val | Ile | Ala |
| Leu | Cys 450 | Ala | Ser | Glu | Gln | Glu 455 | Glu | Glu | Gln | Leu | Val 460 | Ala | Val | Glu | Ala |
| Leu 465 | Ile | His | Ala | Ala | Gly 470 | Lys | Ala | Lys | Arg | Ala 475 | Ser | Phe | Ile | Thr | Ala 480 |
| Asn | Gly | Val | Ser | Leu 485 | Leu | Lys | Asp | Leu | Tyr 490 | Lys | Cys | Ser | Glu | Lys 495 | Asp |
| Ser | Ile | Arg | Ile 500 | Arg | Ala | Leu | Val | Gly 505 | Leu | Cys | Lys | Leu | Gly 510 | Ser | Ala |
| Gly | Gly | Thr 515 | Asp | Phe | Ser | Met | Lys 520 | Gln | Phe | Ala | Glu | Gly 525 | Ser | Thr | Leu |
| Lys | Leu 530 | Ala | Lys | Gln | Cys | Arg 535 | Lys | Trp | Leu | Cys | Asn 540 | Asp | Gln | Ile | Asp |
| Ala 545 | Gly | Thr | Arg | Arg | Trp 550 | Ala | Val | Glu | Gly | Leu 555 | Ala | Tyr | Leu | Thr | Phe 560 |
| Asp | Ala | Asp | Val | Lys 565 | Glu | Glu | Phe | Val | Glu 570 | Asp | Ala | Ala | Ala | Leu 575 | Lys |

| | | | | | | | | | | | | | | |
|---|---|---|---|---|---|---|---|---|---|---|---|---|---|---|
| Ala | Leu | Phe | Gln | Leu | Ser | Arg | Leu | Glu | Glu | Arg | Ser | Val | Leu | Phe | Ala |
| | | | 580 | | | | | 585 | | | | | 590 | | |
| Val | Ala | Ser | Ala | Leu | Val | Asn | Cys | Thr | Asn | Ser | Tyr | Asp | Tyr | Glu | Glu |
| | | 595 | | | | | 600 | | | | | 605 | | | |
| Pro | Asp | Pro | Lys | Met | Val | Glu | Leu | Ala | Lys | Tyr | Ala | Lys | Gln | His | Val |
| | 610 | | | | | 615 | | | | | 620 | | | | |
| Pro | Glu | Gln | His | Pro | Lys | Asp | Lys | Pro | Ser | Phe | Val | Arg | Ala | Arg | Val |
| 625 | | | | | 630 | | | | | 635 | | | | | 640 |
| Lys | Lys | Leu | Leu | Ala | Ala | Gly | Val | Val | Ser | Ala | Met | Val | Cys | Met | Val |
| | | | | 645 | | | | | 650 | | | | | 655 | |
| Lys | Thr | Glu | Ser | Pro | Val | Leu | Thr | Ser | Ser | Cys | Arg | Glu | Leu | Leu | Ser |
| | | | 660 | | | | | 665 | | | | | 670 | | |
| Arg | Val | Phe | Leu | Ala | Leu | Val | Glu | Val | Glu | Asp | Arg | Gly | Thr | Val |
| | | 675 | | | | | 680 | | | | | 685 | | | |
| Val | Ala | Gln | Gly | Gly | Gly | Arg | Ala | Leu | Ile | Pro | Leu | Ala | Leu | Glu | Gly |
| | | 690 | | | | | 695 | | | | | 700 | | | |
| Thr | Asp | Val | Gly | Gln | Thr | Lys | Ala | Ala | Gln | Ala | Leu | Ala | Lys | Leu | Thr |
| 705 | | | | | 710 | | | | | 715 | | | | | 720 |
| Ile | Thr | Ser | Asn | Pro | Glu | Met | Thr | Phe | Pro | Gly | Glu | Arg | Ile | Tyr | Glu |
| | | | | 725 | | | | | 730 | | | | | 735 | |
| Val | Val | Arg | Pro | Leu | Val | Ser | Leu | Leu | His | Leu | Asn | Cys | Ser | Gly | Leu |
| | | | 740 | | | | | 745 | | | | | 750 | | |
| Gln | Asn | Phe | Glu | Ala | Leu | Met | Ala | Leu | Thr | Asn | Leu | Ala | Gly | Ile | Ser |
| | | 755 | | | | | 760 | | | | | 765 | | | |
| Glu | Arg | Leu | Arg | Gln | Lys | Ile | Leu | Lys | Glu | Lys | Ala | Val | Pro | Met | Ile |
| | 770 | | | | | 775 | | | | | 780 | | | | |
| Glu | Gly | Tyr | Met | Phe | Glu | Glu | His | Glu | Met | Ile | Arg | Arg | Ala | Ala | Thr |
| 785 | | | | | 790 | | | | | 795 | | | | | 800 |
| Glu | Cys | Met | Cys | Asn | Leu | Ala | Met | Ser | Lys | Glu | Val | Gln | Asp | Leu | Phe |
| | | | | 805 | | | | | 810 | | | | | 815 | |
| Glu | Ala | Gln | Gly | Asn | Asp | Arg | Leu | Lys | Leu | Leu | Val | Leu | Tyr | Ser | Gly |
| | | | 820 | | | | | 825 | | | | | 830 | | |
| Glu | Asp | Asp | Glu | Leu | Leu | Gln | Arg | Ala | Ala | Ala | Gly | Gly | Leu | Ala | Met |
| | | 835 | | | | | 840 | | | | | 845 | | | |
| Leu | Thr | Ser | Met | Arg | Pro | Thr | Leu | Cys | Ser | Arg | Ile | Pro | Gln | Val | Thr |
| | 850 | | | | | 855 | | | | | 860 | | | | |
| Thr | His | Trp | Leu | Glu | Ile | Leu | Gln | Ala | Leu | Leu | Leu | Ser | Ser | Asn | Gln |
| 865 | | | | | 870 | | | | | 875 | | | | | 880 |
| Glu | Leu | Gln | His | Arg | Gly | Ala | Val | Val | Val | Leu | Asn | Met | Val | Glu | Ala |
| | | | | 885 | | | | | 890 | | | | | 895 | |
| Ser | Arg | Glu | Ile | Ala | Ser | Thr | Leu | Met | Glu | Ser | Glu | Met | Met | Glu | Ile |
| | | | 900 | | | | | 905 | | | | | 910 | | |
| Leu | Ser | Val | Leu | Ala | Lys | Gly | Asp | His | Ser | Pro | Val | Thr | Arg | Ala | Ala |
| | | 915 | | | | | 920 | | | | | 925 | | | |
| Ala | Ala | Cys | Leu | Asp | Lys | Ala | Val | Glu | Tyr | Gly | Leu | Ile | Gln | Pro | Asn |
| | | 930 | | | | | 935 | | | | | 940 | | | |
| Gln | Asp | Gly | Glu |
| 945 | | | | |

( 2 ) INFORMATION FOR SEQ ID NO:15:

( i ) SEQUENCE CHARACTERISTICS:
        ( A ) LENGTH: 6002 base pairs
        ( B ) TYPE: nucleic acid
        ( C ) STRANDEDNESS: double ( D ) TOPOLOGY: linear ( i i ) MOLECULE TYPE: cDNA ( i i i ) HYPOTHETICAL: NO ( i x ) FEATURE:
   ( A ) NAME/KEY: CDS
   ( B ) LOCATION: 326..5092

( x i ) SEQUENCE DESCRIPTION: SEQ ID NO:15:

```
CACGTGCATG TGTAGCATGC CTTGGTTTTT CCTTTGGCAT CTGAAAAAGG CACAACCTGA        60

AAGACCTAGA ACCCAGTGTC GGTCCCCAGG CCCTTTGGGA CAGGAAGAGA AGAGCCGTGT       120

GGCCGCGGGG AGGATGTCCT GCGGCGGGGC TGTCCTCGCG GACTGACTGG ACTCCATCTC       180

CCAGCGGGCG CCGCGGCGCG GCCACGCCCC CCCACTCCCC GCGCGCGCCC GGTGGAGACT       240

TCGATTTTCA GAATTCCTCC TGGGAATGCT GACTCCTTGC TTGGTGCCCT GATGCTTCTC       300

TGAGATAAAC TGATGAATTG GAACC ATG GTG CAA AAG AAG AAG TTC TGT CCT         352
                            Met Val Gln Lys Lys Lys Phe Cys Pro
                              1               5

CGG TTA CTT GAC TAT CTA GTG ATC GTA GGG GCC AGG CAC CCG AGC AGT         400
Arg Leu Leu Asp Tyr Leu Val Ile Val Gly Ala Arg His Pro Ser Ser
 10              15                  20                      25

GAT AGC GTG GCC CAG ACT CCT GAA TTG CTA CGG CGA TAC CCC TTG GAG         448
Asp Ser Val Ala Gln Thr Pro Glu Leu Leu Arg Arg Tyr Pro Leu Glu
                 30                  35                  40

GAT CAC ACT GAG TTT CCC CTG CCC CCA GAT GTA GTG TTC TTC TGC CAG         496
Asp His Thr Glu Phe Pro Leu Pro Pro Asp Val Val Phe Phe Cys Gln
             45                  50                  55

CCC GAG GGC TGC CTG AGC GTG CGG CAG CGG CGC ATG AGC CTT CGG GAT         544
Pro Glu Gly Cys Leu Ser Val Arg Gln Arg Arg Met Ser Leu Arg Asp
         60                  65                  70

GAT ACC TCT TTT GTC TTC ACC CTC ACT GAC AAG GAC ACT GGA GTC ACG         592
Asp Thr Ser Phe Val Phe Thr Leu Thr Asp Lys Asp Thr Gly Val Thr
     75                  80                  85

CGA TAT GGC ATC TGT GTT AAC TTC TAC CGC TCC TTC CAA AAG CGA ATC         640
Arg Tyr Gly Ile Cys Val Asn Phe Tyr Arg Ser Phe Gln Lys Arg Ile
 90              95                 100                     105

TCT AAG GAG AAG GGG GAA GGT GGG GCA GGG TCC CGT GGG AAG GAA GGA         688
Ser Lys Glu Lys Gly Glu Gly Gly Ala Gly Ser Arg Gly Lys Glu Gly
                110                 115                     120

ACC CAT GCC ACC TGT GCC TCA GAA GAG GGT GGC ACT GAG AGC TCA GAG         736
Thr His Ala Thr Cys Ala Ser Glu Glu Gly Gly Thr Glu Ser Ser Glu
             125                 130                     135

AGT GGC TCA TCC CTG CAG CCT CTC AGT GCT GAC TCT ACC CCT GAT GTG         784
Ser Gly Ser Ser Leu Gln Pro Leu Ser Ala Asp Ser Thr Pro Asp Val
         140                 145                     150

AAC CAG TCT CCT CGG GGC AAA CGC CGG GCC AAG GCG GGG AGC CGC TCC         832
Asn Gln Ser Pro Arg Gly Lys Arg Arg Ala Lys Ala Gly Ser Arg Ser
     155                 160                     165

CGC AAC AGT ACT CTC ACG TCC CTG TGC GTG CTC AGC CAC TAC CCT TTC         880
Arg Asn Ser Thr Leu Thr Ser Leu Cys Val Leu Ser His Tyr Pro Phe
170                 175                     180                 185

TTC TCC ACC TTC CGA GAG TGT TTG TAT ACT CTC AAG CGC CTG GTG GAC         928
Phe Ser Thr Phe Arg Glu Cys Leu Tyr Thr Leu Lys Arg Leu Val Asp
                190                 195                     200

TGC TGT AGT GAG CGC CTT CTG GGC AAG AAA CTG GGC ATC CCT CGA GGC         976
Cys Cys Ser Glu Arg Leu Leu Gly Lys Lys Leu Gly Ile Pro Arg Gly
             205                 210                     215
```

```
GTA CAA AGG GAC ACC ATG TGG CGG ATC TTT ACT GGA TCG CTG CTG GTA      1024
Val Gln Arg Asp Thr Met Trp Arg Ile Phe Thr Gly Ser Leu Leu Val
        220                 225                 230

GAG GAG AAG TCA AGT GCC CTT CTG CAT GAC CTT CGA GAG ATT GAG GCC      1072
Glu Glu Lys Ser Ser Ala Leu Leu His Asp Leu Arg Glu Ile Glu Ala
        235                 240                 245

TGG ATC TAT CGA TTG CTG CGC TCC CCA GTA CCC GTC TCT GGG CAG AAG      1120
Trp Ile Tyr Arg Leu Leu Arg Ser Pro Val Pro Val Ser Gly Gln Lys
250                 255                 260                 265

CGA GTA GAC ATC GAG GTC CTA CCC CAA GAG CTC CAG CCA GCT CTG ACC      1168
Arg Val Asp Ile Glu Val Leu Pro Gln Glu Leu Gln Pro Ala Leu Thr
                    270                 275                 280

TTT GCT CTT CCA GAC CCA TCT CGA TTC ACC CTA GTG GAT TTC CCA CTG      1216
Phe Ala Leu Pro Asp Pro Ser Arg Phe Thr Leu Val Asp Phe Pro Leu
            285                 290                 295

CAC CTT CCC TTG GAA CTT CTA GGT GTG GAC GCC TGT CTC CAG GTG CTA      1264
His Leu Pro Leu Glu Leu Leu Gly Val Asp Ala Cys Leu Gln Val Leu
        300                 305                 310

ACC TGC ATT CTG TTA GAG CAC AAG GTG GTG CTA CAG TCC CGA GAC TAC      1312
Thr Cys Ile Leu Leu Glu His Lys Val Val Leu Gln Ser Arg Asp Tyr
    315                 320                 325

AAT GCA CTC TCC ATG TCT GTG ATG GCA TTC GTG GCA ATG ATC TAC CCA      1360
Asn Ala Leu Ser Met Ser Val Met Ala Phe Val Ala Met Ile Tyr Pro
330                 335                 340                 345

CTG GAA TAT ATG TTT CCT GTC ATC CCG CTA CTA CCC ACC TGC ATG GCA      1408
Leu Glu Tyr Met Phe Pro Val Ile Pro Leu Leu Pro Thr Cys Met Ala
                350                 355                 360

TCA GCA GAG CAG CTG CTG TTG GCT CCA ACC CCG TAC ATC ATT GGG GTT      1456
Ser Ala Glu Gln Leu Leu Leu Ala Pro Thr Pro Tyr Ile Ile Gly Val
            365                 370                 375

CCT GCC AGC TTC TTC CTC TAC AAA CTG GAC TTC AAA ATG CCT GAT GAT      1504
Pro Ala Ser Phe Phe Leu Tyr Lys Leu Asp Phe Lys Met Pro Asp Asp
        380                 385                 390

GTA TGG CTA GTG GAT CTG GAC AGC AAT AGG GTG ATT GCC CCC ACC AAT      1552
Val Trp Leu Val Asp Leu Asp Ser Asn Arg Val Ile Ala Pro Thr Asn
    395                 400                 405

GCA GAA GTG CTG CCT ATC CTG CCA GAA CCA GAA TCA CTA GAG CTG AAA      1600
Ala Glu Val Leu Pro Ile Leu Pro Glu Pro Glu Ser Leu Glu Leu Lys
410                 415                 420                 425

AAG CAT TTA AAG CAG GCC TTG GCC AGC ATG AGT CTC AAC ACC CAG CCC      1648
Lys His Leu Lys Gln Ala Leu Ala Ser Met Ser Leu Asn Thr Gln Pro
                430                 435                 440

ATC CTC AAT CTG GAG AAA TTT CAT GAG GGC CAG GAG ATC CCC CTT CTC      1696
Ile Leu Asn Leu Glu Lys Phe His Glu Gly Gln Glu Ile Pro Leu Leu
            445                 450                 455

TTG GGA AGG CCT TCT AAT GAC CTG CAG TCC ACA CCG TCC ACT GAA TTC      1744
Leu Gly Arg Pro Ser Asn Asp Leu Gln Ser Thr Pro Ser Thr Glu Phe
        460                 465                 470

AAC CCA CTC ATC TAT GGC AAT GAT GTG GAT TCT GTG GAT GTT GCA ACC      1792
Asn Pro Leu Ile Tyr Gly Asn Asp Val Asp Ser Val Asp Val Ala Thr
    475                 480                 485

AGG GTT GCC ATG GTA CGG TTC TTC AAT TCC GCC AAC GTG CTG CAG GGA      1840
Arg Val Ala Met Val Arg Phe Phe Asn Ser Ala Asn Val Leu Gln Gly
490                 495                 500                 505

TTT CAG ATG CAC ACG CGT ACC CTG CGC CTC TTT CCT CGG CCT GTG GTA      1888
Phe Gln Met His Thr Arg Thr Leu Arg Leu Phe Pro Arg Pro Val Val
                510                 515                 520

GCT TTT CAA GCT GGC TCC TTT CTA GCC TCA CGT CCC CGG CAG ACT CCT      1936
Ala Phe Gln Ala Gly Ser Phe Leu Ala Ser Arg Pro Arg Gln Thr Pro
            525                 530                 535
```

| | | | | | | | | | | | | | | | | |
|---|---|---|---|---|---|---|---|---|---|---|---|---|---|---|---|---|
| TTT | GCC | GAG | AAA | TTG | GCC | AGG | ACT | CAG | GCT | GTG | GAG | TAC | TTT | GGG | GAA | 1984 |
| Phe | Ala | Glu | Lys | Leu | Ala | Arg | Thr | Gln | Ala | Val | Glu | Tyr | Phe | Gly | Glu | |
| | | 540 | | | | 545 | | | | | 550 | | | | | |
| TGG | ATC | CTT | AAC | CCC | ACC | AAC | TAT | GCC | TTT | CAG | CGA | ATT | CAC | AAC | AAT | 2032 |
| Trp | Ile | Leu | Asn | Pro | Thr | Asn | Tyr | Ala | Phe | Gln | Arg | Ile | His | Asn | Asn | |
| | 555 | | | | | 560 | | | | | 565 | | | | | |
| ATG | TTT | GAT | CCA | GCC | CTG | ATT | GGT | GAC | AAG | CCA | AAG | TGG | TAT | GCT | CAT | 2080 |
| Met | Phe | Asp | Pro | Ala | Leu | Ile | Gly | Asp | Lys | Pro | Lys | Trp | Tyr | Ala | His | |
| 570 | | | | | 575 | | | | 580 | | | | | | 585 | |
| CAG | CTG | CAG | CCT | ATC | CAC | TAT | CGC | GTC | TAT | GAC | AGC | AAT | TCC | CAG | CTG | 2128 |
| Gln | Leu | Gln | Pro | Ile | His | Tyr | Arg | Val | Tyr | Asp | Ser | Asn | Ser | Gln | Leu | |
| | | | | 590 | | | | 595 | | | | | 600 | | | |
| GCT | GAG | GCC | CTG | AGT | GTA | CCA | CCA | GAG | CGG | GAC | TCT | GAC | TCC | GAA | CCT | 2176 |
| Ala | Glu | Ala | Leu | Ser | Val | Pro | Pro | Glu | Arg | Asp | Ser | Asp | Ser | Glu | Pro | |
| | | | 605 | | | | | 610 | | | | 615 | | | | |
| ACT | GAT | GAT | AGT | GGC | AGT | GAT | AGT | ATG | GAT | TAT | GAC | GAT | TCA | AGC | TCT | 2224 |
| Thr | Asp | Asp | Ser | Gly | Ser | Asp | Ser | Met | Asp | Tyr | Asp | Asp | Ser | Ser | Ser | |
| | | 620 | | | | | 625 | | | | | 630 | | | | |
| TCT | TAC | TCC | TCC | CTT | GGT | GAC | TTT | GTC | AGT | GAA | ATG | ATG | AAA | TGT | GAC | 2272 |
| Ser | Tyr | Ser | Ser | Leu | Gly | Asp | Phe | Val | Ser | Glu | Met | Met | Lys | Cys | Asp | |
| | 635 | | | | | 640 | | | | | 645 | | | | | |
| ATT | AAT | GGT | GAT | ACT | CCC | AAT | GTG | GAC | CCT | CTG | ACA | CAT | GCA | GCA | CTG | 2320 |
| Ile | Asn | Gly | Asp | Thr | Pro | Asn | Val | Asp | Pro | Leu | Thr | His | Ala | Ala | Leu | |
| 650 | | | | | 655 | | | | 660 | | | | | | 665 | |
| GGG | GAT | GCC | AGC | GAG | GTG | GAG | ATT | GAC | GAG | CTG | CAG | AAT | CAG | AAG | GAA | 2368 |
| Gly | Asp | Ala | Ser | Glu | Val | Glu | Ile | Asp | Glu | Leu | Gln | Asn | Gln | Lys | Glu | |
| | | | | 670 | | | | | 675 | | | | | 680 | | |
| GCA | GAA | GAG | CCT | GGC | CCA | GAC | AGT | GAG | AAC | TCT | CAG | GAA | AAC | CCC | CCA | 2416 |
| Ala | Glu | Glu | Pro | Gly | Pro | Asp | Ser | Glu | Asn | Ser | Gln | Glu | Asn | Pro | Pro | |
| | | | 685 | | | | | 690 | | | | | 695 | | | |
| CTG | CGC | TCC | AGC | TCT | AGC | ACC | ACA | GCC | AGC | AGC | AGC | CCC | AGC | ACT | GTC | 2464 |
| Leu | Arg | Ser | Ser | Ser | Ser | Thr | Thr | Ala | Ser | Ser | Ser | Pro | Ser | Thr | Val | |
| | | 700 | | | | | 705 | | | | | 710 | | | | |
| ATC | CAC | GGA | GCC | AAC | TCT | GAA | CCT | GCT | GAC | TCT | ACG | GAG | ATG | GAT | GAT | 2512 |
| Ile | His | Gly | Ala | Asn | Ser | Glu | Pro | Ala | Asp | Ser | Thr | Glu | Met | Asp | Asp | |
| | 715 | | | | | 720 | | | | | 725 | | | | | |
| AAG | GCA | GCA | GTA | GGC | GTC | TCC | AAG | CCC | CTC | CCT | TCC | GTG | CCT | CCC | AGC | 2560 |
| Lys | Ala | Ala | Val | Gly | Val | Ser | Lys | Pro | Leu | Pro | Ser | Val | Pro | Pro | Ser | |
| 730 | | | | | 735 | | | | 740 | | | | | | 745 | |
| ATT | GGC | AAA | TCG | AAC | ATG | GAC | AGA | CGT | CAG | GCA | GAA | ATT | GGA | GAG | GGG | 2608 |
| Ile | Gly | Lys | Ser | Asn | Met | Asp | Arg | Arg | Gln | Ala | Glu | Ile | Gly | Glu | Gly | |
| | | | | 750 | | | | 755 | | | | | 760 | | | |
| TCA | GTG | CGC | CGG | CGA | ATC | TAT | GAC | AAT | CCA | TAC | TTC | GAG | CCC | CAA | TAT | 2656 |
| Ser | Val | Arg | Arg | Arg | Ile | Tyr | Asp | Asn | Pro | Tyr | Phe | Glu | Pro | Gln | Tyr | |
| | | | 765 | | | | | 770 | | | | | 775 | | | |
| GGC | TTT | CCC | CCT | GAG | GAA | GAT | GAG | GAT | GAG | CAG | GGG | GAA | AGT | TAC | ACT | 2704 |
| Gly | Phe | Pro | Pro | Glu | Glu | Asp | Glu | Asp | Glu | Gln | Gly | Glu | Ser | Tyr | Thr | |
| | | 780 | | | | | 785 | | | | | 790 | | | | |
| CCC | CGA | TTC | AGC | CAA | CAT | GTC | AGT | GGC | AAT | CGG | GCT | CAA | AAG | CTG | CTG | 2752 |
| Pro | Arg | Phe | Ser | Gln | His | Val | Ser | Gly | Asn | Arg | Ala | Gln | Lys | Leu | Leu | |
| | 795 | | | | | 800 | | | | | 805 | | | | | |
| CGG | CCC | AAC | AGC | TTG | AGA | CTG | GCA | AGT | GAC | TCA | GAT | GCA | GAG | TCA | GAC | 2800 |
| Arg | Pro | Asn | Ser | Leu | Arg | Leu | Ala | Ser | Asp | Ser | Asp | Ala | Glu | Ser | Asp | |
| 810 | | | | | 815 | | | | 820 | | | | | | 825 | |
| TCT | CGG | GCA | AGC | TCT | CCC | AAC | TCC | ACC | GTC | TCC | AAC | ACC | AGC | ACC | GAG | 2848 |
| Ser | Arg | Ala | Ser | Ser | Pro | Asn | Ser | Thr | Val | Ser | Asn | Thr | Ser | Thr | Glu | |
| | | | | 830 | | | | 835 | | | | | 840 | | | |
| GGC | TTC | GGG | GGC | ATC | ATG | TCT | TTT | GCC | AGC | AGC | CTC | TAT | CGG | AAC | CAC | 2896 |
| Gly | Phe | Gly | Gly | Ile | Met | Ser | Phe | Ala | Ser | Ser | Leu | Tyr | Arg | Asn | His | |
| | | | 845 | | | | | 850 | | | | | 855 | | | |

| | | | | | | | | | | | | | | | | |
|---|---|---|---|---|---|---|---|---|---|---|---|---|---|---|---|---|
| AGT | ACC | AGC | TTC | AGT | CTT | TCA | AAC | CTC | ACA | CTG | CCC | ACC | AAA | GGT | GCC | 2944 |
| Ser | Thr | Ser | Phe | Ser | Leu | Ser | Asn | Leu | Thr | Leu | Pro | Thr | Lys | Gly | Ala | |
| | | 860 | | | | 865 | | | | | 870 | | | | | |
| CGA | GAG | AAG | GCC | ACG | CCC | TTC | CCC | AGT | CTG | AAA | GGA | AAC | AGG | AGG | GCG | 2992 |
| Arg | Glu | Lys | Ala | Thr | Pro | Phe | Pro | Ser | Leu | Lys | Gly | Asn | Arg | Arg | Ala | |
| 875 | | | | | 880 | | | | | 885 | | | | | | |
| TTA | GTG | GAT | CAG | AAG | TCA | TCT | GTC | ATT | AAA | CAC | AGC | CCA | ACA | GTG | AAA | 3040 |
| Leu | Val | Asp | Gln | Lys | Ser | Ser | Val | Ile | Lys | His | Ser | Pro | Thr | Val | Lys | |
| 890 | | | | | 895 | | | | | 900 | | | | | 905 | |
| AGA | GAA | CCT | CCA | TCA | CCC | CAG | GGT | CGA | TCC | AGC | AAT | TCT | AGT | GAG | AAC | 3088 |
| Arg | Glu | Pro | Pro | Ser | Pro | Gln | Gly | Arg | Ser | Ser | Asn | Ser | Ser | Glu | Asn | |
| | | | | 910 | | | | | 915 | | | | | 920 | | |
| CAG | CAG | TTC | CTG | AAG | GAG | GTG | GTG | CAC | AGC | GTG | CTG | GAC | GGC | CAG | GGA | 3136 |
| Gln | Gln | Phe | Leu | Lys | Glu | Val | Val | His | Ser | Val | Leu | Asp | Gly | Gln | Gly | |
| | | | | 925 | | | | | 930 | | | | | 935 | | |
| GTT | GGC | TGG | CTC | AAC | ATG | AAA | AAG | GTG | CGC | CGG | CTG | CTG | GAG | AGC | GAG | 3184 |
| Val | Gly | Trp | Leu | Asn | Met | Lys | Lys | Val | Arg | Arg | Leu | Leu | Glu | Ser | Glu | |
| | | | 940 | | | | | 945 | | | | | 950 | | | |
| CAG | CTG | CGA | GTC | TTT | GTC | CTG | AGC | AAG | CTG | AAC | CGC | ATG | GTG | CAG | TCA | 3232 |
| Gln | Leu | Arg | Val | Phe | Val | Leu | Ser | Lys | Leu | Asn | Arg | Met | Val | Gln | Ser | |
| | | 955 | | | | | 960 | | | | | 965 | | | | |
| GAG | GAC | GAT | GCC | CGG | CAG | GAC | ATC | ATC | CCG | GAT | GTG | GAG | ATC | AGT | CGG | 3280 |
| Glu | Asp | Asp | Ala | Arg | Gln | Asp | Ile | Ile | Pro | Asp | Val | Glu | Ile | Ser | Arg | |
| 970 | | | | | 975 | | | | | 980 | | | | | 985 | |
| AAG | GTG | TAC | AAG | GGA | ATG | TTA | GAC | CTC | CTC | AAG | TGT | ACA | GTC | CTC | AGC | 3328 |
| Lys | Val | Tyr | Lys | Gly | Met | Leu | Asp | Leu | Leu | Lys | Cys | Thr | Val | Leu | Ser | |
| | | | | 990 | | | | | 995 | | | | | 1000 | | |
| TTG | GAG | CAG | TCC | TAT | GCC | CAC | GCG | GGT | CTG | GGT | GGC | ATG | GCC | AGC | ATC | 3376 |
| Leu | Glu | Gln | Ser | Tyr | Ala | His | Ala | Gly | Leu | Gly | Gly | Met | Ala | Ser | Ile | |
| | | | | 1005 | | | | | 1010 | | | | | 1015 | | |
| TTT | GGG | CTT | TTG | GAG | ATT | GCC | CAG | ACC | CAC | TAC | TAT | AGT | AAA | GAA | CCA | 3424 |
| Phe | Gly | Leu | Leu | Glu | Ile | Ala | Gln | Thr | His | Tyr | Tyr | Ser | Lys | Glu | Pro | |
| | | | 1020 | | | | | 1025 | | | | | 1030 | | | |
| GAC | AAG | CGG | AAG | AGA | AGT | CCA | ACA | GAA | AGT | GTA | AAT | ACC | CCA | GTT | GGC | 3472 |
| Asp | Lys | Arg | Lys | Arg | Ser | Pro | Thr | Glu | Ser | Val | Asn | Thr | Pro | Val | Gly | |
| | | | 1035 | | | | | 1040 | | | | | 1045 | | | |
| AAG | GAT | CCT | GGC | CTA | GCT | GGG | CGG | GGG | GAC | CCA | AAG | GCT | ATG | GCA | CAA | 3520 |
| Lys | Asp | Pro | Gly | Leu | Ala | Gly | Arg | Gly | Asp | Pro | Lys | Ala | Met | Ala | Gln | |
| 1050 | | | | | 1055 | | | | | 1060 | | | | | 1065 | |
| CTG | AGA | GTT | CCA | CAA | CTG | GGA | CCT | CGG | GCA | CCA | AGT | GCC | ACA | GGA | AAG | 3568 |
| Leu | Arg | Val | Pro | Gln | Leu | Gly | Pro | Arg | Ala | Pro | Ser | Ala | Thr | Gly | Lys | |
| | | | | 1070 | | | | | 1075 | | | | | 1080 | | |
| GGT | CCT | AAG | GAA | CTG | GAC | ACC | AGA | AGT | TTA | AAG | GAA | GAA | AAT | TTT | ATA | 3616 |
| Gly | Pro | Lys | Glu | Leu | Asp | Thr | Arg | Ser | Leu | Lys | Glu | Glu | Asn | Phe | Ile | |
| | | | | 1085 | | | | | 1090 | | | | | 1095 | | |
| GCA | TCT | ATT | GGG | CCT | GAA | GTA | ATC | AAA | CCT | GTC | TTT | GAC | CTT | GGT | GAG | 3664 |
| Ala | Ser | Ile | Gly | Pro | Glu | Val | Ile | Lys | Pro | Val | Phe | Asp | Leu | Gly | Glu | |
| | | | 1100 | | | | | 1105 | | | | | 1110 | | | |
| ACA | GAG | GAG | AAA | AAG | TCC | CAG | ATC | AGC | GCA | GAC | AGT | GGT | GTG | AGC | CTG | 3712 |
| Thr | Glu | Glu | Lys | Lys | Ser | Gln | Ile | Ser | Ala | Asp | Ser | Gly | Val | Ser | Leu | |
| | | 1115 | | | | | 1120 | | | | | 1125 | | | | |
| ACG | TCT | AGT | TCC | CAG | AGG | ACT | GAT | CAA | GAC | TCT | GTC | ATC | GGC | GTG | AGT | 3760 |
| Thr | Ser | Ser | Ser | Gln | Arg | Thr | Asp | Gln | Asp | Ser | Val | Ile | Gly | Val | Ser | |
| 1130 | | | | | 1135 | | | | | 1140 | | | | | 1145 | |
| CCA | GCT | GTT | ATG | ATC | CGC | AGC | TCA | AGT | CAG | GAT | TCT | GAA | GTT | AGC | ACC | 3808 |
| Pro | Ala | Val | Met | Ile | Arg | Ser | Ser | Ser | Gln | Asp | Ser | Glu | Val | Ser | Thr | |
| | | | | 1150 | | | | | 1155 | | | | | 1160 | | |
| GTG | GTG | AGT | AAT | AGC | TCT | GGA | GAG | ACC | CTT | GGA | GCT | GAC | AGT | GAC | TTG | 3856 |
| Val | Val | Ser | Asn | Ser | Ser | Gly | Glu | Thr | Leu | Gly | Ala | Asp | Ser | Asp | Leu | |
| | | | 1165 | | | | | 1170 | | | | | 1175 | | | |

| | | | | | | | | | | | | | | | |
|---|---|---|---|---|---|---|---|---|---|---|---|---|---|---|---|
| AGC | AGC | AAT | GCA | GGT | GAT | GGA | CCA | GGT | GGC | GAG | GGC | AGT | GTT | CAC | CTG |
| Ser | Ser | Asn | Ala | Gly | Asp | Gly | Pro | Gly | Gly | Glu | Gly | Ser | Val | His | Leu |
| | | 1180 | | | | | 1185 | | | | | 1190 | | | |

3904

| GCA | AGC | TCT | CGG | GGC | ACT | TTG | TCT | GAT | AGT | GAA | ATT | GAG | ACC | AAC | TCT |
|---|---|---|---|---|---|---|---|---|---|---|---|---|---|---|---|
| Ala | Ser | Ser | Arg | Gly | Thr | Leu | Ser | Asp | Ser | Glu | Ile | Glu | Thr | Asn | Ser |
| 1195 | | | | | 1200 | | | | | 1205 | | | | | |

3952

| GCC | ACA | AGC | ACC | ATC | TTT | GGT | AAA | GCC | CAC | AGC | TTG | AAG | CCA | AGC | ATA |
|---|---|---|---|---|---|---|---|---|---|---|---|---|---|---|---|
| Ala | Thr | Ser | Thr | Ile | Phe | Gly | Lys | Ala | His | Ser | Leu | Lys | Pro | Ser | Ile |
| 1210 | | | | 1215 | | | | | 1220 | | | | | 1225 | |

4000

| AAG | GAG | AAG | CTG | GCA | GGC | AGC | CCC | ATT | CGT | ACT | TCT | GAA | GAT | GTG | AGC |
|---|---|---|---|---|---|---|---|---|---|---|---|---|---|---|---|
| Lys | Glu | Lys | Leu | Ala | Gly | Ser | Pro | Ile | Arg | Thr | Ser | Glu | Asp | Val | Ser |
| | | | | 1230 | | | | | 1235 | | | | | 1240 | |

4048

| CAG | CGA | GTC | TAT | CTC | TAT | GAG | GGA | CTC | CTA | GGC | AAA | GAG | CGT | TCT | ACT |
|---|---|---|---|---|---|---|---|---|---|---|---|---|---|---|---|
| Gln | Arg | Val | Tyr | Leu | Tyr | Glu | Gly | Leu | Leu | Gly | Lys | Glu | Arg | Ser | Thr |
| | | | | 1245 | | | | | 1250 | | | | | 1255 | |

4096

| TTA | TGG | GAC | CAA | ATG | CAA | TTC | TGG | GAA | GAT | GCC | TTC | TTA | GAT | GCT | GTG |
|---|---|---|---|---|---|---|---|---|---|---|---|---|---|---|---|
| Leu | Trp | Asp | Gln | Met | Gln | Phe | Trp | Glu | Asp | Ala | Phe | Leu | Asp | Ala | Val |
| | | | 1260 | | | | | 1265 | | | | | 1270 | | |

4144

| ATG | TTG | GAG | AGA | GAA | GGG | ATG | GGT | ATG | GAC | CAG | GGT | CCC | CAG | GAA | ATG |
|---|---|---|---|---|---|---|---|---|---|---|---|---|---|---|---|
| Met | Leu | Glu | Arg | Glu | Gly | Met | Gly | Met | Asp | Gln | Gly | Pro | Gln | Glu | Met |
| | | 1275 | | | | | 1280 | | | | | 1285 | | | |

4192

| ATC | GAC | AGG | TAC | CTG | TCC | CTT | GGA | GAA | CAT | GAC | CGG | AAG | CGC | CTG | GAA |
|---|---|---|---|---|---|---|---|---|---|---|---|---|---|---|---|
| Ile | Asp | Arg | Tyr | Leu | Ser | Leu | Gly | Glu | His | Asp | Arg | Lys | Arg | Leu | Glu |
| 1290 | | | | | 1295 | | | | | 1300 | | | | | 1305 |

4240

| GAT | GAT | GAA | GAT | CGC | TTG | CTG | GCC | ACA | CTT | CTG | CAC | AAC | CTC | ATC | TCC |
|---|---|---|---|---|---|---|---|---|---|---|---|---|---|---|---|
| Asp | Asp | Glu | Asp | Arg | Leu | Leu | Ala | Thr | Leu | Leu | His | Asn | Leu | Ile | Ser |
| | | | | 1310 | | | | | 1315 | | | | | 1320 | |

4288

| TAC | ATG | CTG | CTG | ATG | AAG | GTA | AAT | AAG | AAT | GAC | ATC | CGC | AAG | AAG | GTG |
|---|---|---|---|---|---|---|---|---|---|---|---|---|---|---|---|
| Tyr | Met | Leu | Leu | Met | Lys | Val | Asn | Lys | Asn | Asp | Ile | Arg | Lys | Lys | Val |
| | | | | 1325 | | | | | 1330 | | | | | 1335 | |

4336

| AGG | CGC | CTA | ATG | GGA | AAG | TCG | CAC | ATT | GGG | CTT | GTG | TAC | AGC | CAG | CAA |
|---|---|---|---|---|---|---|---|---|---|---|---|---|---|---|---|
| Arg | Arg | Leu | Met | Gly | Lys | Ser | His | Ile | Gly | Leu | Val | Tyr | Ser | Gln | Gln |
| | | | 1340 | | | | | 1345 | | | | | 1350 | | |

4384

| ATC | AAT | GAG | GTG | CTT | GAT | CAG | CTG | GCG | AAC | CTG | AAT | GGA | CGC | GAT | CTC |
|---|---|---|---|---|---|---|---|---|---|---|---|---|---|---|---|
| Ile | Asn | Glu | Val | Leu | Asp | Gln | Leu | Ala | Asn | Leu | Asn | Gly | Arg | Asp | Leu |
| | | 1355 | | | | | 1360 | | | | | 1365 | | | |

4432

| TCT | ATC | TGG | TCC | AGT | GGC | AGC | CGG | CAC | ATG | AAG | AAG | CAG | ACA | TTT | GTG |
|---|---|---|---|---|---|---|---|---|---|---|---|---|---|---|---|
| Ser | Ile | Trp | Ser | Ser | Gly | Ser | Arg | His | Met | Lys | Lys | Gln | Thr | Phe | Val |
| 1370 | | | | | 1375 | | | | | 1380 | | | | | 1385 |

4480

| GTA | CAT | GCA | GGG | ACA | GAT | ACA | AAC | GGA | GAT | ATC | TTT | TTC | ATG | GAG | GTG |
|---|---|---|---|---|---|---|---|---|---|---|---|---|---|---|---|
| Val | His | Ala | Gly | Thr | Asp | Thr | Asn | Gly | Asp | Ile | Phe | Phe | Met | Glu | Val |
| | | | | 1390 | | | | | 1395 | | | | | 1400 | |

4528

| TGC | GAT | GAC | TGT | GTG | GTG | TTG | CGT | AGT | AAC | ATC | GGA | ACA | GTG | TAT | GAG |
|---|---|---|---|---|---|---|---|---|---|---|---|---|---|---|---|
| Cys | Asp | Asp | Cys | Val | Val | Leu | Arg | Ser | Asn | Ile | Gly | Thr | Val | Tyr | Glu |
| | | | 1405 | | | | | 1410 | | | | | 1415 | | |

4576

| CGC | TGG | TGG | TAC | GAG | AAG | CTC | ATC | AAC | ATG | ACC | TAC | TGT | CCC | AAG | ACG |
|---|---|---|---|---|---|---|---|---|---|---|---|---|---|---|---|
| Arg | Trp | Trp | Tyr | Glu | Lys | Leu | Ile | Asn | Met | Thr | Tyr | Cys | Pro | Lys | Thr |
| | | 1420 | | | | | 1425 | | | | | 1430 | | | |

4624

| AAG | GTG | TTG | TGC | TTG | TGG | CGT | AGA | AAT | GGC | TCT | GAG | ACC | CAG | CTC | AAC |
|---|---|---|---|---|---|---|---|---|---|---|---|---|---|---|---|
| Lys | Val | Leu | Cys | Leu | Trp | Arg | Arg | Asn | Gly | Ser | Glu | Thr | Gln | Leu | Asn |
| | 1435 | | | | | 1440 | | | | | 1445 | | | | |

4672

| AAG | TTC | TAT | ACT | AAA | AAG | TGT | CGG | GAG | CTG | TAC | TAC | TGT | GTG | AAG | GAC |
|---|---|---|---|---|---|---|---|---|---|---|---|---|---|---|---|
| Lys | Phe | Tyr | Thr | Lys | Lys | Cys | Arg | Glu | Leu | Tyr | Tyr | Cys | Val | Lys | Asp |
| 1450 | | | | | 1455 | | | | | 1460 | | | | | 1465 |

4720

| AGC | ATG | GAG | CGC | GCT | GCC | GCC | CGA | CAG | CAA | AGC | ATC | AAA | CCC | GGA | CCT |
|---|---|---|---|---|---|---|---|---|---|---|---|---|---|---|---|
| Ser | Met | Glu | Arg | Ala | Ala | Ala | Arg | Gln | Gln | Ser | Ile | Lys | Pro | Gly | Pro |
| | | | | 1470 | | | | | 1475 | | | | | 1480 | |

4768

| GAA | TTG | GGT | GGC | GAG | TTC | CCT | GTG | CAG | GAC | CTG | AAG | ACT | GGT | GAG | GGT |
|---|---|---|---|---|---|---|---|---|---|---|---|---|---|---|---|
| Glu | Leu | Gly | Gly | Glu | Phe | Pro | Val | Gln | Asp | Leu | Lys | Thr | Gly | Glu | Gly |
| | | | | 1485 | | | | | 1490 | | | | | 1495 | |

4816

-continued

| | | | | | | | | | | | | | | | | |
|---|---|---|---|---|---|---|---|---|---|---|---|---|---|---|---|---|
| GGC | CTG | CTG | CAG | GTG | ACC | CTG | GAA | GGG | ATC | AAC | CTC | AAA | TTC | ATG | CAC | 4864 |
| Gly | Leu | Leu | Gln | Val | Thr | Leu | Glu | Gly | Ile | Asn | Leu | Lys | Phe | Met | His | |
| | | 1500 | | | | | 1505 | | | | | 1510 | | | | |
| AAT | CAG | GTT | TTC | ATA | GAG | CTG | AAT | CAC | ATT | AAA | AAG | TGC | AAT | ACA | GTT | 4912 |
| Asn | Gln | Val | Phe | Ile | Glu | Leu | Asn | His | Ile | Lys | Lys | Cys | Asn | Thr | Val | |
| | 1515 | | | | | 1520 | | | | | 1525 | | | | | |
| CGA | GGC | GTC | TTT | GTC | CTG | GAG | GAA | TTT | GTT | CCT | GAA | ATT | AAA | GAA | GTG | 4960 |
| Arg | Gly | Val | Phe | Val | Leu | Glu | Glu | Phe | Val | Pro | Glu | Ile | Lys | Glu | Val | |
| 1530 | | | | | 1535 | | | | | 1540 | | | | | 1545 | |
| GTG | AGC | CAC | AAG | TAC | AAG | ACA | CCA | ATG | GCC | CAC | GAA | ATC | TGC | TAC | TCC | 5008 |
| Val | Ser | His | Lys | Tyr | Lys | Thr | Pro | Met | Ala | His | Glu | Ile | Cys | Tyr | Ser | |
| | | | | 1550 | | | | | 1555 | | | | | 1560 | | |
| GTA | TTA | TGT | CTC | TTC | TCG | TAC | GTG | GCT | GCA | GTT | CAT | AGC | AGT | GAG | GAA | 5056 |
| Val | Leu | Cys | Leu | Phe | Ser | Tyr | Val | Ala | Ala | Val | His | Ser | Ser | Glu | Glu | |
| | | | 1565 | | | | | 1570 | | | | | 1575 | | | |
| GAT | CTC | AGA | ACC | CCG | CCC | CGG | CCT | GTC | TCT | AGC | TGA | TGGAGAGGG | | | | 5102 |
| Asp | Leu | Arg | Thr | Pro | Pro | Arg | Pro | Val | Ser | Ser | * | | | | | |
| | | 1580 | | | | 1585 | | | | | | | | | | |

| | | | | | |
|---|---|---|---|---|---|
| CTACGCAGCT | GCCCCAGCCC | AGGGCACGCC | CCTGGCCCCT | TGCTGTTCCC | AAGTGCACGA | 5162 |
| TGCTGCTGTG | ACTGAGGAGT | GGATGATGCT | CGTGTGTCCT | CTGCAAGCCC | CCTGCTGTGG | 5222 |
| CTTGGTTGGT | TACCGGTTAT | GTGTCCCTCT | GAGTGTGTCT | TGAGCGTGTC | CACCTTCTCC | 5282 |
| CTCTCCACTC | CCAGAAGACC | AAACTGCCTT | CCCCTCAGGG | CTCAAGAATG | TGTACAGTCT | 5342 |
| GTGGGGCCGG | TGTGAACCCA | CTATTTTGTG | TCCTTGAGAC | ATTTGTGTTG | TGGTTCCTTG | 5402 |
| TCCTTGTCCC | TGGCGTTATA | ACTGTCCACT | GCAAGAGTCT | GGCTCTCCCT | TCTCTGTGAC | 5462 |
| CCGGCATGAC | TGGGCGCCTG | GAGCAGTTTC | ACTCTGTGAG | GAGTGAGGGA | ACCCTGGGGC | 5522 |
| TCACCCTCTC | AGAGGAAGGG | CACAGAGAGG | AAGGGAAGAA | TTGGGGGGCA | GCCGGAGTGA | 5582 |
| GTGGCAGCCT | CCCTGCTTCC | TTCTGCATTC | CCAAGCCGGC | AGCTACTGCC | CAGGGCCCGC | 5642 |
| AGTGTTGGCT | GCTGCCTGCC | ACAGCCTCTG | TGACTGCAGT | GGAGCGGCGA | ATTCCCTGTG | 5702 |
| GCCTGCCACG | CCTTCGGCAT | CAGAGGATGG | AGTGGTCGAG | GCTAGTGGAG | TCCCAGGGAC | 5762 |
| CGCTGGCTGC | TCTGCCTGAG | CATCAGGGAG | GGGGCAGGAA | AGACCAAGCT | GGGTTTGCAC | 5822 |
| ATCTGTCTGC | AGGCTGTCTC | TCCAGGCACG | GGGTGTCAGG | AGGGAGAGAC | AGCCTGGGTA | 5882 |
| TGGGCAAGAA | ATGACTGTAA | ATATTTCAGC | CCCACATTAT | TTATAGAAAA | TGTACAGTTG | 5942 |
| TGTGAATGTG | AAATAAATGT | CCTCAACTCC | CAAAAAAAAA | AAAAAAAAA | AAAAAAAAA | 6002 |

( 2 ) INFORMATION FOR SEQ ID NO:16:

( i ) SEQUENCE CHARACTERISTICS:
        ( A ) LENGTH: 1588 amino acids
        ( B ) TYPE: amino acid
        ( D ) TOPOLOGY: linear ( i i ) MOLECULE TYPE: protein ( x i ) SEQUENCE DESCRIPTION: SEQ ID NO:16:

| | | | | | | | | | | | | | | |
|---|---|---|---|---|---|---|---|---|---|---|---|---|---|---|
| Met | Val | Gln | Lys | Lys | Lys | Phe | Cys | Pro | Arg | Leu | Leu | Asp | Tyr | Leu | Val |
| 1 | | | | 5 | | | | | 10 | | | | | 15 | |
| Ile | Val | Gly | Ala | Arg | His | Pro | Ser | Ser | Asp | Ser | Val | Ala | Gln | Thr | Pro |
| | | | 20 | | | | | 25 | | | | | 30 | | |
| Glu | Leu | Leu | Arg | Arg | Tyr | Pro | Leu | Glu | Asp | His | Thr | Glu | Phe | Pro | Leu |
| | | 35 | | | | | 40 | | | | | 45 | | | |
| Pro | Pro | Asp | Val | Val | Phe | Phe | Cys | Gln | Pro | Glu | Gly | Cys | Leu | Ser | Val |
| | | 50 | | | | | 55 | | | | | 60 | | | |
| Arg | Gln | Arg | Arg | Met | Ser | Leu | Arg | Asp | Asp | Thr | Ser | Phe | Val | Phe | Thr |
| 65 | | | | | 70 | | | | | 75 | | | | | 80 |

-continued

```
Leu Thr Asp Lys Asp Thr Gly Val Thr Arg Tyr Gly Ile Cys Val Asn
                 85                  90                      95
Phe Tyr Arg Ser Phe Gln Lys Arg Ile Ser Lys Glu Lys Gly Glu Gly
                100                 105                 110
Gly Ala Gly Ser Arg Gly Lys Glu Gly Thr His Ala Thr Cys Ala Ser
                115                 120                 125
Glu Glu Gly Gly Thr Glu Ser Ser Glu Ser Gly Ser Ser Leu Gln Pro
            130                 135                 140
Leu Ser Ala Asp Ser Thr Pro Asp Val Asn Gln Ser Pro Arg Gly Lys
145                 150                 155                 160
Arg Arg Ala Lys Ala Gly Ser Arg Ser Arg Asn Ser Thr Leu Thr Ser
                165                 170                 175
Leu Cys Val Leu Ser His Tyr Pro Phe Phe Ser Thr Phe Arg Glu Cys
                180                 185                 190
Leu Tyr Thr Leu Lys Arg Leu Val Asp Cys Cys Ser Glu Arg Leu Leu
            195                 200                 205
Gly Lys Lys Leu Gly Ile Pro Arg Gly Val Gln Arg Asp Thr Met Trp
        210                 215                 220
Arg Ile Phe Thr Gly Ser Leu Leu Val Glu Glu Lys Ser Ser Ala Leu
225                 230                 235                 240
Leu His Asp Leu Arg Glu Ile Glu Ala Trp Ile Tyr Arg Leu Leu Arg
                245                 250                 255
Ser Pro Val Pro Val Ser Gly Gln Lys Arg Val Asp Ile Glu Val Leu
                260                 265                 270
Pro Gln Glu Leu Gln Pro Ala Leu Thr Phe Ala Leu Pro Asp Pro Ser
            275                 280                 285
Arg Phe Thr Leu Val Asp Phe Pro Leu His Leu Pro Leu Glu Leu Leu
        290                 295                 300
Gly Val Asp Ala Cys Leu Gln Val Leu Thr Cys Ile Leu Leu Glu His
305                 310                 315                 320
Lys Val Val Leu Gln Ser Arg Asp Tyr Asn Ala Leu Ser Met Ser Val
                325                 330                 335
Met Ala Phe Val Ala Met Ile Tyr Pro Leu Glu Tyr Met Phe Pro Val
                340                 345                 350
Ile Pro Leu Leu Pro Thr Cys Met Ala Ser Ala Glu Gln Leu Leu Leu
            355                 360                 365
Ala Pro Thr Pro Tyr Ile Ile Gly Val Pro Ala Ser Phe Phe Leu Tyr
        370                 375                 380
Lys Leu Asp Phe Lys Met Pro Asp Asp Val Trp Leu Val Asp Leu Asp
385                 390                 395                 400
Ser Asn Arg Val Ile Ala Pro Thr Asn Ala Glu Val Leu Pro Ile Leu
                405                 410                 415
Pro Glu Pro Glu Ser Leu Glu Leu Lys Lys His Leu Lys Gln Ala Leu
                420                 425                 430
Ala Ser Met Ser Leu Asn Thr Gln Pro Ile Leu Asn Leu Glu Lys Phe
            435                 440                 445
His Glu Gly Gln Glu Ile Pro Leu Leu Leu Gly Arg Pro Ser Asn Asp
        450                 455                 460
Leu Gln Ser Thr Pro Ser Thr Glu Phe Asn Pro Leu Ile Tyr Gly Asn
465                 470                 475                 480
Asp Val Asp Ser Val Asp Val Ala Thr Arg Val Ala Met Val Arg Phe
                485                 490                 495
```

```
Phe  Asn  Ser  Ala  Asn  Val  Leu  Gln  Gly  Phe  Gln  Met  His  Thr  Arg  Thr
               500                 505                      510

Leu  Arg  Leu  Phe  Pro  Arg  Pro  Val  Ala  Phe  Gln  Ala  Gly  Ser  Phe
               515                 520                      525

Leu  Ala  Ser  Arg  Pro  Arg  Gln  Thr  Pro  Phe  Ala  Glu  Lys  Leu  Ala  Arg
          530                      535                      540

Thr  Gln  Ala  Val  Glu  Tyr  Phe  Gly  Glu  Trp  Ile  Leu  Asn  Pro  Thr  Asn
545                      550                      555                      560

Tyr  Ala  Phe  Gln  Arg  Ile  His  Asn  Asn  Met  Phe  Asp  Pro  Ala  Leu  Ile
                    565                 570                      575

Gly  Asp  Lys  Pro  Lys  Trp  Tyr  Ala  His  Gln  Leu  Gln  Pro  Ile  His  Tyr
               580                      585                      590

Arg  Val  Tyr  Asp  Ser  Asn  Ser  Gln  Leu  Ala  Glu  Ala  Leu  Ser  Val  Pro
          595                      600                      605

Pro  Glu  Arg  Asp  Ser  Asp  Ser  Glu  Pro  Thr  Asp  Asp  Ser  Gly  Ser  Asp
          610                      615                      620

Ser  Met  Asp  Tyr  Asp  Asp  Ser  Ser  Ser  Tyr  Ser  Ser  Leu  Gly  Asp
625                      630                      635                      640

Phe  Val  Ser  Glu  Met  Met  Lys  Cys  Asp  Ile  Asn  Gly  Asp  Thr  Pro  Asn
                    645                 650                      655

Val  Asp  Pro  Leu  Thr  His  Ala  Ala  Leu  Gly  Asp  Ala  Ser  Glu  Val  Glu
               660                      665                      670

Ile  Asp  Glu  Leu  Gln  Asn  Gln  Lys  Glu  Ala  Glu  Glu  Pro  Gly  Pro  Asp
          675                      680                      685

Ser  Glu  Asn  Ser  Gln  Glu  Asn  Pro  Pro  Leu  Arg  Ser  Ser  Ser  Thr
690                      695                      700

Thr  Ala  Ser  Ser  Ser  Pro  Ser  Thr  Val  Ile  His  Gly  Ala  Asn  Ser  Glu
705                      710                      715                      720

Pro  Ala  Asp  Ser  Thr  Glu  Met  Asp  Asp  Lys  Ala  Ala  Val  Gly  Val  Ser
               725                      730                      735

Lys  Pro  Leu  Pro  Ser  Val  Pro  Pro  Ser  Ile  Gly  Lys  Ser  Asn  Met  Asp
               740                      745                      750

Arg  Arg  Gln  Ala  Glu  Ile  Gly  Glu  Gly  Ser  Val  Arg  Arg  Ile  Tyr
          755                      760                      765

Asp  Asn  Pro  Tyr  Phe  Glu  Pro  Gln  Tyr  Gly  Phe  Pro  Pro  Glu  Glu  Asp
770                      775                      780

Glu  Asp  Glu  Gln  Gly  Glu  Ser  Tyr  Thr  Pro  Arg  Phe  Ser  Gln  His  Val
785                      790                      795                      800

Ser  Gly  Asn  Arg  Ala  Gln  Lys  Leu  Leu  Arg  Pro  Asn  Ser  Leu  Arg  Leu
               805                      810                      815

Ala  Ser  Asp  Ser  Asp  Ala  Glu  Ser  Asp  Ser  Arg  Ala  Ser  Ser  Pro  Asn
               820                      825                      830

Ser  Thr  Val  Ser  Asn  Thr  Ser  Thr  Glu  Gly  Phe  Gly  Gly  Ile  Met  Ser
          835                      840                      845

Phe  Ala  Ser  Ser  Leu  Tyr  Arg  Asn  His  Ser  Thr  Ser  Phe  Ser  Leu  Ser
     850                      855                      860

Asn  Leu  Thr  Leu  Pro  Thr  Lys  Gly  Ala  Arg  Glu  Lys  Ala  Thr  Pro  Phe
865                      870                      875                      880

Pro  Ser  Leu  Lys  Gly  Asn  Arg  Arg  Ala  Leu  Val  Asp  Gln  Lys  Ser  Ser
                    885                      890                      895

Val  Ile  Lys  His  Ser  Pro  Thr  Val  Lys  Arg  Glu  Pro  Pro  Ser  Pro  Gln
               900                      905                      910

Gly  Arg  Ser  Ser  Asn  Ser  Ser  Glu  Asn  Gln  Gln  Phe  Leu  Lys  Glu  Val
          915                      920                      925
```

Val His Ser Val Leu Asp Gly Gln Gly Val Gly Trp Leu Asn Met Lys
930                     935                     940

Lys Val Arg Arg Leu Leu Glu Ser Glu Gln Leu Arg Val Phe Val Leu
945                     950                     955                     960

Ser Lys Leu Asn Arg Met Val Gln Ser Glu Asp Ala Arg Gln Asp
            965                     970                     975

Ile Ile Pro Asp Val Glu Ile Ser Arg Lys Val Tyr Lys Gly Met Leu
            980                     985                     990

Asp Leu Leu Lys Cys Thr Val Leu Ser Leu Glu Gln Ser Tyr Ala His
            995                     1000                    1005

Ala Gly Leu Gly Gly Met Ala Ser Ile Phe Gly Leu Leu Glu Ile Ala
            1010                    1015                    1020

Gln Thr His Tyr Tyr Ser Lys Glu Pro Asp Lys Arg Lys Arg Ser Pro
1025                    1030                    1035                    1040

Thr Glu Ser Val Asn Thr Pro Val Gly Lys Asp Pro Gly Leu Ala Gly
                1045                    1050                    1055

Arg Gly Asp Pro Lys Ala Met Ala Gln Leu Arg Val Pro Gln Leu Gly
                1060                    1065                    1070

Pro Arg Ala Pro Ser Ala Thr Gly Lys Gly Pro Lys Glu Leu Asp Thr
                1075                    1080                    1085

Arg Ser Leu Lys Glu Glu Asn Phe Ile Ala Ser Ile Gly Pro Glu Val
            1090                    1095                    1100

Ile Lys Pro Val Phe Asp Leu Gly Glu Thr Glu Glu Lys Lys Ser Gln
1105                    1110                    1115                    1120

Ile Ser Ala Asp Ser Gly Val Ser Leu Thr Ser Ser Ser Gln Arg Thr
                1125                    1130                    1135

Asp Gln Asp Ser Val Ile Gly Val Ser Pro Ala Val Met Ile Arg Ser
                1140                    1145                    1150

Ser Ser Gln Asp Ser Glu Val Ser Thr Val Val Ser Asn Ser Ser Gly
                1155                    1160                    1165

Glu Thr Leu Gly Ala Asp Ser Asp Leu Ser Ser Asn Ala Gly Asp Gly
    1170                    1175                    1180

Pro Gly Gly Glu Gly Ser Val His Leu Ala Ser Ser Arg Gly Thr Leu
1185                    1190                    1195                    1200

Ser Asp Ser Glu Ile Glu Thr Asn Ser Ala Thr Ser Thr Ile Phe Gly
                1205                    1210                    1215

Lys Ala His Ser Leu Lys Pro Ser Ile Lys Glu Lys Leu Ala Gly Ser
                1220                    1225                    1230

Pro Ile Arg Thr Ser Glu Asp Val Ser Gln Arg Val Tyr Leu Tyr Glu
            1235                    1240                    1245

Gly Leu Leu Gly Lys Glu Arg Ser Thr Leu Trp Asp Gln Met Gln Phe
    1250                    1255                    1260

Trp Glu Asp Ala Phe Leu Asp Ala Val Met Leu Glu Arg Glu Gly Met
1265                    1270                    1275                    1280

Gly Met Asp Gln Gly Pro Gln Glu Met Ile Asp Arg Tyr Leu Ser Leu
            1285                    1290                    1295

Gly Glu His Asp Arg Lys Arg Leu Glu Asp Asp Glu Asp Arg Leu Leu
            1300                    1305                    1310

Ala Thr Leu Leu His Asn Leu Ile Ser Tyr Met Leu Leu Met Lys Val
            1315                    1320                    1325

Asn Lys Asn Asp Ile Arg Lys Lys Val Arg Arg Leu Met Gly Lys Ser
    1330                    1335                    1340

```
His  Ile  Gly  Leu  Val  Tyr  Ser  Gln  Gln  Ile  Asn  Glu  Val  Leu  Asp  Gln
1345                     1350                     1355                     1360

Leu  Ala  Asn  Leu  Asn  Gly  Arg  Asp  Leu  Ser  Ile  Trp  Ser  Ser  Gly  Ser
                    1365                     1370                     1375

Arg  His  Met  Lys  Lys  Gln  Thr  Phe  Val  Val  His  Ala  Gly  Thr  Asp  Thr
               1380                     1385                     1390

Asn  Gly  Asp  Ile  Phe  Phe  Met  Glu  Val  Cys  Asp  Asp  Cys  Val  Val  Leu
          1395                     1400                     1405

Arg  Ser  Asn  Ile  Gly  Thr  Val  Tyr  Glu  Arg  Trp  Trp  Tyr  Glu  Lys  Leu
     1410                     1415                     1420

Ile  Asn  Met  Thr  Tyr  Cys  Pro  Lys  Thr  Lys  Val  Leu  Cys  Leu  Trp  Arg
1425                     1430                     1435                     1440

Arg  Asn  Gly  Ser  Glu  Thr  Gln  Leu  Asn  Lys  Phe  Tyr  Thr  Lys  Lys  Cys
                    1445                     1450                     1455

Arg  Glu  Leu  Tyr  Tyr  Cys  Val  Lys  Asp  Ser  Met  Glu  Arg  Ala  Ala  Ala
               1460                     1465                     1470

Arg  Gln  Gln  Ser  Ile  Lys  Pro  Gly  Pro  Glu  Leu  Gly  Gly  Glu  Phe  Pro
               1475                     1480                     1485

Val  Gln  Asp  Leu  Lys  Thr  Gly  Glu  Gly  Gly  Leu  Leu  Gln  Val  Thr  Leu
     1490                     1495                     1500

Glu  Gly  Ile  Asn  Leu  Lys  Phe  Met  His  Asn  Gln  Val  Phe  Ile  Glu  Leu
1505                     1510                     1515                     1520

Asn  His  Ile  Lys  Lys  Cys  Asn  Thr  Val  Arg  Gly  Val  Phe  Val  Leu  Glu
               1525                     1530                     1535

Glu  Phe  Val  Pro  Glu  Ile  Lys  Glu  Val  Val  Ser  His  Lys  Tyr  Lys  Thr
               1540                     1545                     1550

Pro  Met  Ala  His  Glu  Ile  Cys  Tyr  Ser  Val  Leu  Cys  Leu  Phe  Ser  Tyr
               1555                     1560                     1565

Val  Ala  Ala  Val  His  Ser  Ser  Glu  Glu  Asp  Leu  Arg  Thr  Pro  Pro  Arg
     1570                     1575                     1580

Pro  Val  Ser  Ser    *
1585
```